US006680321B1

(12) United States Patent
Roberts et al.

(10) Patent No.: US 6,680,321 B1
(45) Date of Patent: *Jan. 20, 2004

(54) COMPOUNDS WITH ANALGESIC EFFECT

(75) Inventors: Edward Roberts, St Lazare de Vaudreuil (CA); Niklas Plobeck, Ville St Laurent (CA); Claes Wahlestedt, Montreal (CA)

(73) Assignee: AstraZeneca Canada, Inc., Mississauga (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/631,116

(22) Filed: Aug. 2, 2000

Related U.S. Application Data

(63) Continuation of application No. 08/836,830, filed as application No. PCT/SE96/01635 on Dec. 11, 1996, now Pat. No. 6,130,222.

(30) Foreign Application Priority Data

Dec. 22, 1995 (SE) .............................. 9504661

(51) Int. Cl.[7] .................. A61K 31/495; C07D 295/155
(52) U.S. Cl. ........................ 514/255.04; 514/253.01; 514/252.13; 514/254.01; 514/254.1; 544/360; 544/372; 544/379; 544/393; 544/396
(58) Field of Search ................ 544/396, 393, 544/360, 372, 379; 514/255.04, 253.01, 252.13, 254.01, 254.1

(56) References Cited

U.S. PATENT DOCUMENTS

| | | | |
|---|---|---|---|
| 3,940,386 A | 2/1976 | Szabo et al. | |
| 5,574,159 A | 11/1996 | Chang et al. | 544/396 |
| 5,681,830 A | 10/1997 | Chang et al. | 514/85 |
| 5,807,858 A | 9/1998 | Chang et al. | 514/255 |
| 6,130,222 A | * 10/2000 | Roberts et al. | 514/255.04 |

FOREIGN PATENT DOCUMENTS

| | | | |
|---|---|---|---|
| DE | 24 31 178 | 6/1974 | C07D/295/04 |
| DE | 29 00 810 | 1/1979 | C07D/295/04 |
| EP | 133 323 | 2/1985 | C07D/295/04 |
| EP | 166 302 | 1/1986 | C07D/243/08 |
| EP | 283 310 | 9/1988 | C07D/295/04 |
| EP | 289 227 | 11/1988 | C07D/233/64 |
| FR | 92 12163 | 10/1992 | C07D/401/06 |
| GB | 2 076 403 | 12/1981 | C07D/241/04 |
| GB | 2 210 366 | 6/1989 | C07D/295/04 |
| JP | 7-138230 | 5/1995 | |
| WO | WO 86/04584 | 8/1986 | |
| WO | WO 91/07967 | 6/1991 | |
| WO | WO 93/15062 | 8/1993 | C07D/241/04 |
| WO | WO 95/04051 | 2/1995 | C07D/295/155 |
| WO | WO 97/23466 | 7/1997 | |
| WO | WO 98/28270 | 7/1998 | |
| WO | WO 98/28275 | 7/1998 | |
| WO | WO 99/33806 | 7/1999 | |

OTHER PUBLICATIONS

Chang, et al., "A Novel, Potent and Selective Nonpeptidic Delta Opioid Receptor Agonist BW373U86," *J. Pharmacol. and Exper. Ther.* 267:852–857 (1993).

Takemori, et al., "Selective Naatrexone–Derived Opioid Receptor Antagonists," *Annu. Rev. Pharmacol. Toxicol.* 32–51:239–269 (1992).

English language abstract of document AO2, WPI accession No. 74–81010V/197447, Dialog file 351.

English language abstract of document AP2, WPI accession No. 80–53516C/198031, Dialog file 351.

English language abstract of document AL3, WPI accession No. 94–146424/199418, Dialog file 351.

Dialog abstract for Reference AJ1 above. (JP 7–138230).

Abstract No. 8843b for Reference AJ1 above, *Chemical Abstracts* 124:938 (1996).

Bilsky, et al., "Characterization of Enantiomers of (±)BW373U86 and Related Compounds: Highly Selective Non–Peptidic Delta Opioid Agonists," *Reg. Peptides* 54:25–26 (1994).

Bilsky, et al., "SNC 80, A Selective, Nonpeptidic and Systemically Active Opioid *Delta* Agonist," *J. Pharmacol. Exper. Therap.*273:359–366 (1995).

Calderon, et al., "Probes for Narcotic Receptor Mediated Phenomena. 19. Synthesis of (+)–4–[($\alpha$R)–$\alpha$–((2S, 5R)–4–Allyl–2, 5–Dimethyl–l–Piperazinyl)–3–Methoxybenzyl]–*N,N*–Diethylbenzamide (SNC 80): A Highly Selective, Nonpeptide $\delta$ Opioid Receptor Agonist," *J. Med. Chem.* 37:2125–2128 (1994).

(List continued on next page.)

*Primary Examiner*—Emily Bernhardt
(74) *Attorney, Agent, or Firm*—Michael A. Sanzo; Fitch, Even, Tabin & Flannery

(57) ABSTRACT

Compounds of the formula (I)

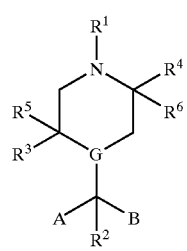

as well as their pharmaceutically acceptable salts, and pharmaceutical compositions comprising the novel compounds. The novel compounds of the formula (I) are useful in the management of pain.

7 Claims, No Drawings

OTHER PUBLICATIONS

Calderon, et al., "Probes for Narcotic Receptor Mediated Phenomena. 23. Synthesis, Opioid Receptor Binding, and Bioassay of the Highly Selective δ Agonist (+)–4–[(αR)–α–((2S,5R)–4–Allyl–2,5–Dimethyl–1–Piperazinyl)–3–Methoxybenzyl]–N,N–Diethylbenzamide (SNC 80) and Related Novel Nonpeptide Δ Opioid Receptor Ligands," *J. Med. Chem.* 40:695–704 (1997).

Katrizky, et al., "Benzotriazole–Mediated Arylalkylation and Heteroarylalkylation," *Chem. Soc. Rev.* 23:363–442 (1994).

Kingsbury, et al., "Synthesis of Structural Analogs of Leukotriene $B_4$ and Their Receptor Binding Activity," *J. Med. Chem.* 36:3308–3320 (1993).

Lopez, et al., "Exploring the Structure–Activity Relationships of [1–(4–*tert*–Butyl–3'–Hydroxy)Benzhydryl–4–Benzylpiperazine] (SL–3111), a High–Affinity and Selective δ–Opioid Receptor Nonpeptide Agonist Ligand," *J. Med. Chem.* 42:5359–5368 (1999).

Plobeck, et al., "New Diarylmethylpiperazines as Potent and Selective Nonpeptidic δ Opioid Receptor Agonists with Increased In Vitro Metabolic Stability," *J. Med. Chem.* 43:3878–3894 (2000).

Suggs, et al., "Facile Synthesis of 8–Substituted Quinolines," *J. Org. Chem.* 45:1514–1515 (1980).

Zhang et al., Probes for Narcotic Receptor Mediated Phenomena. 26. Synthesis and Biological Evaluation of Diarylmethylpiperazines and Diarylmethylpiperidines as Novel, Nonpeptidic δ Opioid Receptor Ligands, *J. Med. Chem.* 42:5455–5463 (1999).

Abstract for HU 217619. A corresponding English language PCT application is cited above as Reference AF1.

Abstract for HU 215847, A corresponding English language PCT application is cited above as Reference AG1.

Burkey, et al., "The Efficacy of Delta–Opioid Receptor–Selective Drugs," Medline Abstract for *Life Sci.* 62:1531–1536 (1998).

Nagase, et al., "The Pharmacological Profile of Delta Opioid Receptor Ligands, (+) and (−) TAN–67 on Pain Modulation," Medline Abstract for *Life Sci.* 68:2227–2231 (2001).

Greene, "Protective Groups in Organic Synthesis," pp. 267–268 and 331 (1981).

* cited by examiner

COMPOUNDS WITH ANALGESIC EFFECT

CROSS REFERENCE TO RELATED APPLICATIONS

The present application is a continuation of U.S. Ser. No. 08/836,830, filed on Apr. 24, 1997 (now U.S. Pat. No. 6,130,222) and claims the benefit thereof. The '830 application represents U.S. national stage of international application PCT/SE96/01635, with an international filing date of Dec. 11, 1996 and which was published in English under Article 21 (2) of the PCT on Jul. 3, 1997. The international application claims priority to Swedish application 9504661-1, filed on Dec. 22, 1995.

FIELD OF THE INVENTION

The present invention is related to novel compounds, to a process for their preparation, their use and pharmaceutical compositions comprising the novel compounds. The novel compounds are used in therapy, and in particular for the treatment of pain.

BACKGROUND AND PRIOR ART

The δ receptor has been identified as having a role in many bodily functions such as circulatory and pain systems. Ligands for the δ receptor may therefore find potential use as analgesics, and/or as antihypertensive agents. Ligands for the δ receptor have also been shown to posess immunomodulatory activities.

The identification of at least three different populations of opioid receptors ($\mu$, $\delta$ and $\kappa$) is now well established and all three are apparent in both central and peripheral nervous systems of many species including man. Analgesia has been observed in various animal models when one or more of these receptors has been activated.

With few exceptions, currently available selective opioid δ ligands are peptidic in nature and are unsuitable for administration by systemic routes. Some non-peptidic δ antagonists have been available for some time (see Takemori and Portoghese, 1992, Ann. Rev. Pharmacol. Tox., 32: 239–269. for review). These compounds, e.g. naltrindole, suffer from rather poor (i.e., <10-fold) selectivity for the δ receptor vs $\mu'$ receptor binding and exhibit no analgesic activity, a fact which underscores the need for the development of highly selective non-peptidic δ agonists.

Recently, a non-peptidic δ agonist, BW 373U86, was described by Chang et al., 1993, J. Pharmacol. Exp. Ther., 267: 852–857., as the first δ-selective non-peptide with analgesic activity, however, it shows significant affinity for the $\mu$ receptor.

Thus, the problem underlying the present invention was to fund new analgesics having excellent analgesic effects, but also with an improved side-effect profile over current $\mu$ agonists and potential oral efficacy.

Analgesics that have been identified and are existing in the prior art have many disadvantages in that they suffer from poor pharmacokinetics and are not analgesic when administered by systemic routes. Also, it has been documented that preferred compounds, described within the prior art, show significant convulsive effects when administered systemically.

In WO 93/15062 and WO 95/045051, some diarylmethylpiperazine and diarylmethylpiperidine compounds, including BW 373U86, are disclosed, but these prior art compounds are structurally distinct from the compounds according to the present invention.

The problem mentioned above has been solved by developing novel piperazine and piperidine compounds, as will be described below.

OUTLINE OF THE INVENTION

The novel compounds according to the present invention are defined by the formula (I)

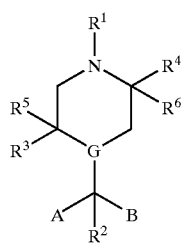

(I)

wherein

G is a carbon atom or a nitrogen atom;

A is selected from
(i) phenyl substituted by any of —COOH, —CONH$_2$, COOCH$_3$, —CN, NH$_2$ or —COCH$_3$;
(ii) naphtyl, benzofuranyl, and quinolinyl; and (iii)

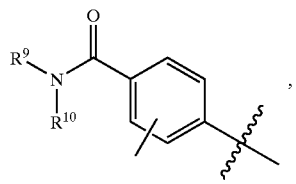

,

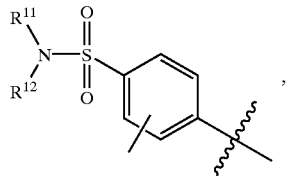

,

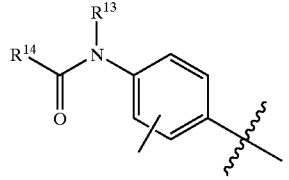

,

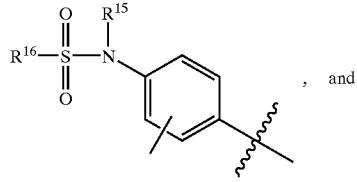

, and

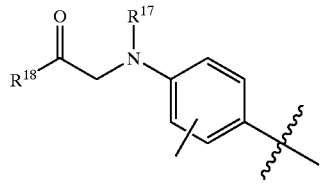

wherein the phenyl ring of each A substituent may be optionally and independently substituted by 1 or 2 substituents selected from hydrogen, CH$_3$, (CH$_2$)$_o$CF$_3$, halogen, CONR$^7$R$^8$, CO$_2$R$^7$, COR$^7$, (CH$_2$)$_o$NR$^7$R$^8$, ( $CH_2)_oCH_3(CH_2)_oSOR^7$, $(CH2)_oSO_2R^7$ and $(CH_2)_o$ $SO_2NR^7R^8$ wherein o is 0, 1, or 2, and $R^7$ and $R^8$ are as defined below;

$R^1$ is selected from hydrogen; a branched or straight $C_1$–$C_6$ alkyl, $C_1$–$C_6$ alkenyl, —CO($C_1$–$C_6$ allyl); ($C_1$–$C_6$ alkyl)-B wherein B is as defined below; $C_3$–$C_8$ cycloallyl, $C_4$–$C_8$ (alkyl-cycloalcyl) wherein alkyl is $C_1$–$C_2$ alkyl and cycloalkyl is $C_3$–$C_6$ cycloalkyl; $C_6$–$C_{10}$ aryl; and heteroaryl having from 5–10 atoms selected from any of C, S, N and O; and whereby the $C_6$–$C_{10}$ aryl and the heteroaryl may optionally be substituted by 1 or 2 substituents selected from hydrogen, $CH_3$, $(CH_2)_oCF_3$, halogen, $CONR^7R^8$, $CO_2R^7$, $COR^7$, $(CH_2)_oNR^7R^8$, $(CH_2)_oCH_3(CH_2)_o$ $SOR^7$, $(CH_2)_oSO_2R^7$ and $(CH_2)_oSO_2NR^7R^8$;
wherein o is 0, 1, or 2, and $R^7$ and $R^8$ are as defined below:

$R^7$ and $R^8$ is each and independently as defined for $R^1$ above;

$R^2$ is selected from hydrogen, $CH_3$, $OR^1$, $CO_2R^1$, and $CH_2CO_2R^1$ wherein $R^1$ is as defined above;

$R^9$, $R^{10}$, $R^{11}$, $R^{12}$, $R^{13}$, $R^{14}$, $R^{15}$, $R^{16}$, $R^{17}$, and $R^{18}$, is each and independently as defined for $R^1$ above;

B is a substituted or unsubstituted aromatic; an optionally substituted $C_5$–$C_{10}$ hydroaromatic; a heteroaromatic or a heterohydroaromatic moiety, each having from 5 to 10 atoms selected from any of C, S, N and O, and each being optionally and independently substituted by 1 or 2 substituents independently selected from hydrogen, $CH_3$, $CF_3$, halogen, $(CH_2)_pCONR^7R^8$, $(CH_2)_pNR^7R^8$, $(CH_2)_pCOR^7$, $(CH_2)_pCO_2R^7$, $OR^7$, $(CH_2)_pSOR^7$, $(CH_2)_pSO_2R^7$, and $(CH_2)_pSO_2NR^7R^8$;
wherein p is 0, 1, 2 or 3 and wherein $R^7$ and $R^8$ are as defined above;

$R^3$, $R^4$, $R^5$ and $R^6$ is each and independently selected from $R^7$, $(CH_2)_pCONR^7R^8$, $(CH_2)_pNR^7R^8$, $(CH_2)_p$ $CONR^7R^8$, $(CH_2)_pCO_2R^7$, $(CH_2)_pPh$, $(CH_2)_p$(p-OH Ph), $(CH_2)_p$-3-indolyl, $(CH_2)_pSR^7$, and $(CH_2)_pOR^7$;
wherein p is 0, 1, 2, 3, or 4, and $R^7$ and $R^8$ are as defined above;

with the proviso that when A is a phenyl ring substituted by a —CN group or by a —$NH_2$ group, B may not be

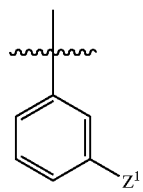

wherein
$Z^1$ is hydroxy, and esters thereof;
hydroxymethyl, and esters thereof; or
amino, and carboxamides and sulfonamides.

Within the scope of the invention are also pharmaceutically acceptable salts of the compounds of the formula (I), as well as isomers, hydrates, isoforms and prodrugs thereof.

Preferred compounds according to the invention are compounds of the formula (I) wherein G is a carbon atom or a nitrogen atom;
A is selected from
(i) phenyl substituted by any of —COOH, —$CONH_2$, $COOCH_3$, —CN, $NH_2$ or —$COCH_3$;
(ii) naphtyl, benzofuanyl, and quinolinyl; and (iii)

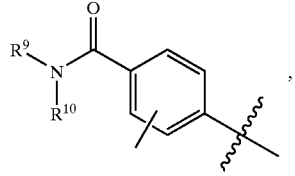

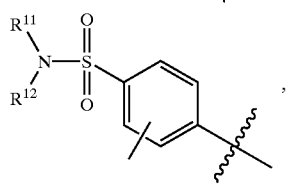

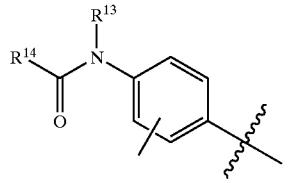

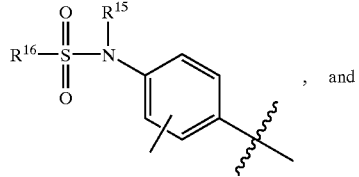

, and

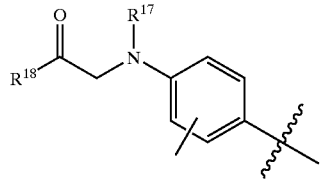

wherein the phenyl ring of each A substituent may be optionally and independently substituted by 1 or 2 substituents selected from hydrogen, $CH_3$, $(CH_2)_oCF_3$, halogen, $CONR^7R^8$, $CO_2R^7$, $COR^7$, $(CH_2)_oNR^7R^8$, $(CH_2)_oCH_3(CH_2)_oSOR^7$, $(CH_2)_oSO_2R^7$ and $(CH_2)_o$ $SO_2NR^7R^8$, wherein o is 0, 1, or 2, and $R^7$ and $R^8$ are as defined below;

$R^1$, $R^7$ and $R^8$ is each and independently selected from hydrogen; a branched or straight $C_1$–$C_4$ alkyl, allyl, —CO—($C_1$–$C_6$ alkyl); ($C_1$–$C_6$ alkyl)-B wherein B is as defined below; $C_3$–$C_5$ cycloalkyl, $C_4$–$C_8$ (alkyl-cycloalkyl) wherein alkyl is $C_1$–$C_2$ alkyl and cycloalkyl is $C_3$–$C_6$ cycloalkyl; and phenyl;

$R^2$ is hydrogen, methyl, or $OR^1$ wherein $R^1$ is as defined above;

$R^9$, $R^{10}$, $R^{11}$, $R^{12}$, $R^{13}$, $R^{14}$, $R^{15}$, $R^{16}$, $R^{17}$, and $R^{18}$, is each and independently as defined for $R^1$ above;

B is selected from phenyl, naphthyl, indolyl, benzofuranyl, dihydrobenzofuranyl, benzothiophenyl, pyrryl, furanyl, quinolinyl, isoquinolinyl, cyclohexyl, cyclohexenyl, cyclopentyl, cyclopentenyl, indanyl, indenyl, tetrahydronaphthyl, tetrahydroquinyl, tetrahydroisoquinolinyl, tetrahydrofuranyl, pyrrolidinyl, indazolinyl, and

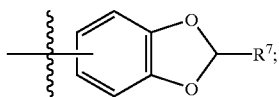

each B group being optionally substituted by 1–2 substituents independently selected from hydrogen, $CH_3$, $CF_3$, halogen, $(CH_2)_p CONR^7R^8$, $(CH_2)_p NR^7R^8$, $(CH_2)_p COR^7$, $(CH_2)_p CO_2R^7$, and $OR^7$;
wherein p is 0 or 1, and wherein $R^7$ and $R^8$ are as defined above; and $R^3$, $R^4$, $R^5$ and $R^6$ is each and independently selected from hydrogen, $CH_3$, $CH(Me)_2$, $CH_2CH(Me)_2$, $CH(Me)CH_2CH_3$ $(CH_2)_p CONR^7R^8$, $(CH_2)_p NR^7R^8$, $(CH_2)_p CONR^7R^8$, $(CH_2)_p CO_2R^7$, $(CH_2)_p Ph$, $(CH_2)_p (p\text{-}OH\ Ph)$, $(CH_2)_p\text{-}3\text{-indolyl}$, $(CH_2)_p SR^7$, and $(CH_2)_p OR^7$,
wherein p is 0, 1, 2, or 3, and wherein $R^7$ and $R^8$ are as defined above;

with the proviso that when A is a phenyl ring substituted by a —CN group or by a —$NH_2$ group, B may not be

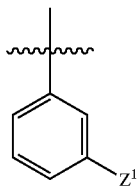

wherein $Z^1$ is hydroxy, and esters thereof;
hydroxymethyl, and esters thereof; or
amino, and carboxamides and sulfonamides.

Especially preferred compounds according to the invention are compounds of the formula (I) wherein G is a nitrogen atom;
A is selected from

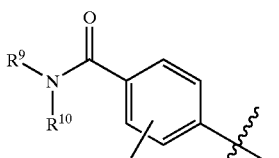

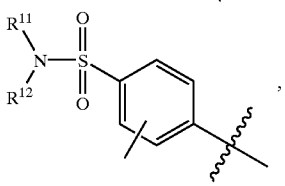

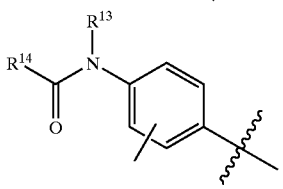

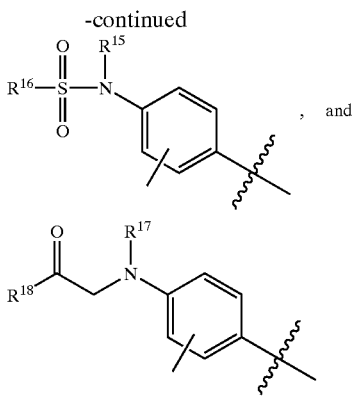

wherein
$R^9$, $R^{10}$, $R^{11}$, $R^{12}$, $R^{13}$, $R^{14}$, $R^{15}$, $R^{16}$, $R^{17}$, and $R^{18}$ is each an ethyl group;
$R^1$ is selected from hydrogen, mnethyl, ethyl, allyl, or $CH_2$-cyclopropyl;
$R^2$ is H, methyl, or $OR^1$, wherein R1 is as defined above;
B is selected from phenyl, naphthyl, indolyl, benzofuranyl, dihydrobenzofuranyl, benzothiophenyl, furanyl, quinolinyl, isoquinolinyl, cyclohexyl, cyclohexenyl, cyclopentyl, cyclopentenyl, indanyl, indenyl, tetrahydronaphthyl, tetrahydroquinyl, tetrahydroisoquinolinyl, tetrahydrofuranyl, indazolinyl, and

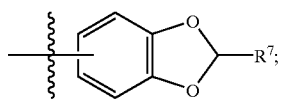

each B group being optionally substituted by 1–2 substituents independently selected from hydrogen, methyl, $CF_3$, halogen, $(CH_2)_p CONR^7R^8$, $(CH_2)_p NR^7R^8$, $(CH_2)_p COR^7$, $(CH_2)_p CO_2R^7$, and $OR^7$,
wherein p is 0, 1, or 2, and wherein $R^7$ and $R^8$ are as defined for $R^1$ above;

$R^3$, $R^4$, $R^5$ and $R^6$ is each and independently selected from H, $CH_3$, $CH(Me)_2$, $CH_2CH(Me)_2$, $CH(Me)CH_2CH_3$ $(CH_2)_p CONR^7R^8$, $(CH_2)_p NR^7R^8$, $(CH_2)_p CONR^7R^8$, $(CH_2)_p CO_2R^7$, $(CH_2)_p Ph$, $(CH_2)_p (p\text{-}OH\ Ph)$, $(CH_2)_p\text{-}3\text{-indolyl}$, $(CH_2)_p SR^7$, and $(CH_2)_p OR^7$
wherein p is 0, 1 or 2, and wherein $R^7$ and $R^8$ are as defined above;

The substituents A and B respectively, may optionally be substituted at any position of the ring.

By "halogen" we mean chloro, fluoro, bromo and iodo.

By "aryl" we mean an aromatic ring having from 6–10 carbon atoms, such as phenyl and naphtyl.

By "heteroaryl" we mean an aromatic ring in which one or more of the 5–10 atoms in the ring are elements other than carbon, such as N, S and O.

By "hydroaromatic" we mean a partly or fully saturated aromatic ring structure having 5–10 carbon atoms in the ring.

By "heterohydroaromatic" we mean a partly or fully saturated aromatic ring structure in which one or more of the 5–10 atoms in the ring are elements other than carbon, such as N, S and O.

By "isomers" we mean compounds of the formula (I), which differ by the position of their functional group and/or orientation. By "orientation" we mean stereoisomers, diastereoisomers, regioisomers and enantiomers.

By "isoforms" we mean compounds of the formula (I) which differ by their crystal lattice, such as crystalline compound and amorphous compounds.

By "prodrug" we mean pharmacologically acceptable derivatives, e.g. esters and amides, such the resulting biotransformation product of the derivative is the active drug. The reference by Goodman and Gilmans, The Pharmacological basis of Therapeutics, 8th ed., McGraw-Hill, Int. Ed. 1992, "Biotransformation of Drugs, p. 13–15, describing prodrugs generally, is hereby incorporated.

The novel compounds of the present invention are useful in therapy, especially for the treatment of pain.

The compounds are also useful for modulating the analgesic effects acting at the $\mu$ opioid receptor subtype, the modulation of side effects seen with agents acting at the $\mu$ opioid receptor subtype such as morphine, especially respiratory depression, gut motility and abuse liability.

Compounds of the invention are also useful as immunomodulators, especially for autoimmune diseases, such as arthritis, for skin grafts, organ transplants and similar surgical needs, for collagen diseases, various allergies, for use as anti tumour agents and anti viral agents.

Compounds of the invention are useful in disease states where degeneration or dysfunction of opioid receptors is present or implicated in that paradigm. This may involve the use of isotopically labeled versions of the compounds of the invention in diagnostic techniques and imaging applications such as positron emission tomography (PET).

Compounds of the invention are useful for the treatment of diarrhea, depression, urinary incontinence, various mental illnesses, cough, lung oedema, various gastro-intestinal disorders, spinal injury and drug addiction, including the treatment of alcohol, nicotine, opioid and other drug abuse and for disorders of the sympathetic nervous system for example hypertension.

The best mode of performing the present invention known at present, is to use the compounds according to Example 21 (compound 33), Example 22 (compound 34), Example 23 (compound 37), Example 24 (compound 38), Example 25 (compound 41), Example 26 (compound 42), Example 27 (compound 45), Example 29 (compound 51), Example 30 (compound 54), Example 35 (compound 64), Example 36 (compound 65), Example 50, and Example 51. The numbering of the compounds is in accordance with the Examples below, as well as in accordance with the numbering in the Schemes presented in the following.

Methods of Preparation

Generalized Method A

An aldehyde or ketone is treated with a nucleophile such as a Grignard or organolithium species to produce the corresponding alcohol. This alcohol may then be converted into a suitable leaving group (X) such as an ester, sulphonate or halide which may in turn be displaced with a nucleophilic species such as a substituted or unsubstituted piperazine. N-(4)-unsubstituted piperazine derivatives may then be suitably substituted with a variety of groups via their organo halide or equivalent species, or acylated with a number of different acylating compounds. This sequence of events will give rise to compounds according to general formula I.

Generalized Method B

An N-protected amino acid, as its activated ester, may be reacted with a second amino acid ester. On treatment with an acid this species may then cyclize to form a piperazinedione. This dione may be reduced via a number of standard methods to the corresponding piperazine (e.g. a reducing agent such as lithium aluminium hydride, by conversion to the thioamide and subsequent desulphurization, hydrogenation in the presence of $POCl_3$ etc.) This piperazine may then be alkylated or acylated on one or more of the nitrogens and/or may be used subsequently in generalized method A.

Deprotection of functional groups or further modifications may then be necessary, these are described for each individual case. Specific examples for the above transformations are given in the experimental.

All transformations contemplated use reagents (including salts) and solvents known to the art of chemistry and to biotransformations carried out in a suitable biological medium to bring about these transformations and includes all reaction enhancing agents (e.g. HMPA), and chiral resolutions using chiral salt formation and chiral biological resolutions.

DETAILED DESCRIPTION OF THE INVENTION

The invention will now be described in more detail by the following examples, which are not to be construed as limiting the invention.

Scheme 1

(±)-3-(αR*/S*)-α-(2S*,5R*)-4-Allyl-2,5-dimethyl-1-piperazinyl)-1-naphthyl)anisole (4 & 5).

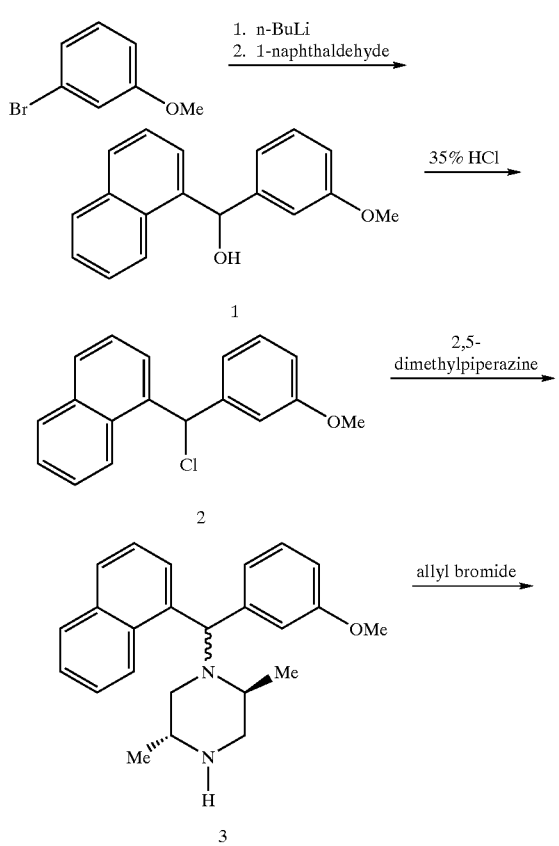

-continued

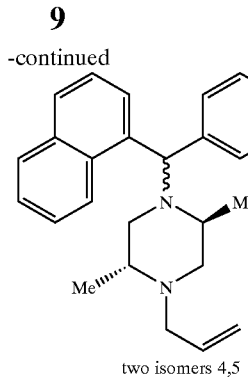

two isomers 4,5

EXAMPLES

The compounds according to Examples 1–3 were synthesized as shown in Scheme 1 above.

A.

I. Preparation of 3-methoxy-α-(1-naphthyl)benzyl alcohol (Compound 1)

To a solution of 3-bromoanisole (5.61 g, 30.0 mmol) in dry THF (80 mL) was dropwise added n-butyl lithium-hexane solution (1.6 M, 37.5 mL, 60 mmol) under nitrogen at −78° C. The reaction mixture was allowed to warm to r.t. in 2 h and cooled down again to −78° C. prior to addition of 1-naphthaldehyde (4.69 g, 30.0 mmol, in 10 mL THF). The mixture was warmed to r.t. in 3 h, and then quenched with aqueous $NH_4Cl$ solution, extracted with ethyl acetate (3×50 mL). The combined organic phases were washed with brine, dried over $MgSO_4$. Removal of solvents in vacuo provided 3-methoxy-α-(1-naphthyl)benzyl alcohol (4.25 g, 54%). GC-MS ($R_t$=10.41 min) 264 ($M^+$), 245, 231, 215, 202, 155, 135, 128, 109.

II. Preparation of 3-methoxy-α-(1-naphthyl)benzyl chloride (Compound 2)

To a solution of 3-methoxy-α-(1-naphthyl)benzyl alcohol (2.5 g, 9.5 mmol) in diethyl ether (5 mL) was added 35% hydrochloric acid (10 mL) at 0° C. The reaction mixture was warmed to r.t. in 1 h, and then extracted with ethyl acetate (3×50 mL). The combined organic layers were washed with aqueous $NH_4Cl$ solution and brine, dried over $MgSO_4$. Evaporation of solvents gave 3-methoxy-α-(1-naphthyl) benzyl chloride (1.94 g, 72%). GC-MS ($R_t$=10.30 min) 282 ($M^+$), 247, 232,215, 202, 189, 163, 151, 139, 123, 101.

Example 1

Preparation of (±)-trans-1-(3-methoxy-α-(1-naphthyl)benzyl)-2,5-dimethylpiperazine (Compound 3)

A mixture of trans-2,5-dimethylpiperazine (456 mg, 4.0 mmol), 3-methoxy-α-(1-naphthyl)benzyl chloride (430 mg, 1.5 mmol) and triethylamine (2 mL) in dry DMF (10 mL) was refluxed for 2 h under nitrogen after cooling down to r.t., the reaction mixture was quenched with 1 N aqueous $NH_4OH$ solution, and extracted with ethyl acetate (3×50 mL). The combined organic layers were washed with 0.5 N aqueous NaOH solution, saturated aqueous $NH_4Cl$ and brine, dried over $MgSO_4$. Removal of solvents gave (±)-trans-1-(3-methoxy-α-(1'-naphthyl)benzyl)-2,5-dimethylpiperazine, which was used directly in the next step: GC-MS (two isomers: $R_t$=12.98 & 13.10 min) 360 ($M^+$), 301, 276, 247, 232, 215, 189, 165, 131, 113.

Example 2 and 3

Preparation of (±)-3-((αR*/S*)-α-((2S*,5R*)-4-Allyl-2,5-dimethyl-1-piperazinyl)-1-naphthyl)anisole (Compounds 4 & 5)

A mixture of above (±)-trans-1-(3-methoxy-α-(1-naphthyl)benzyl)2,5-dimethylpiperazine, $K_2CO_3$ (276 mg, 2.0 mmol) and allyl bromide (242 mg, 2.0 mmol) in DMF (5 mL)/THF (10 mL) was stirred for 3 h at r.t. The reaction mixture was quenched with 1 N $NH_4OH$ and extracted with ethyl acetate (3×50 mL). The combined organic layers were washed with saturated aqueous $NH_4Cl$ and brine, dried over $MgSO_4$. Evaporation of solvents provided crude (±)-3-((αR*/S*)-α-((2S *,5R*)-4-Allyl-2,5-dimethyl-1-piperazinyl)-1-naphthyl)anisole, which were purified by silica gel column eluting with AcOEt-Hexane(2:98→100:0) to yield the two isomers (totally 267 mg, 45% from 2):

The first isomer, compound 4: GC-MS ($R_t$=14.84 min) 401.15 ($M^+$+1, 0.3%), 400.15 ($M^+$, 0.9), 359.15 (0.6), 330.15 (0.4), 302.15 (3.2), 274.15 (8.0), 247.05 (23.0), 215.10 (12.7), 202.05 (7.8),153.15 (100), 126.15 (10.1); $\delta_H$ (400 MHz, $CDCl_3$) 1.02 (d, J=6.4 Hz, 6H), 2.15 (dd, J=11.2, 6.4 Hz, 1H), 2.31 (dd, J=11.2, 6.4 Hz, 1H), 2.60 (m, 1H), 2.74 (dd, J=11.2, 3.2 Hz, 1H), 2.80 (dd, J=11.2, 3.2 Hz, 1H), 2.94 (dd, J=13.6, 7.2 Hz, 1H), 3.03 (dt, J=6.4, 3.2 Hz, 1H), 3.20 (dd, J=13.6, 5.6 Hz, 1H), 3.73 (s, 3H), 5.12 (m, 2H), 5.73 (brs, 1H), 5.83 (m, 1H), 6.68 (dd, J=8.0, 2.4 Hz, 1H), 7.00 (d, J=8.0 Hz, 1H), 7.12 (m, 2H), 7.42 (m, 3H), 7.62 (d, J=7.2 Hz, 1H), 7.71 (d, J=8.0 Hz, 1H), 7.80 (d, J=8.0 Hz, 1H), 8.28 (brs, 1H); $\delta_{C-13}$ (100 MHz, $CDCl_3$) 13.2, 14.2, 35.6, 52.1, 53.0, 55.1, 55.2, 57.2, 63.8, 111.6, 114.4, 117.2, 121.1, 123.8, 125.2, 125.7, 125.8, 127.2, 127.5, 127.8, 128.9, 132.1, 134.0, 135.5, 137.4, 145.5, 159.5

Its HCl salt: m.p. 124–135° C. (Ether); $v_{max}$ (KBr) $cm^{-1}$ 3483, 1601, 1264; Anal.Calcd.for $C_{27}H_{32}N_2O.2HCl.1.0H_2O$: C, 65.98; H, 7.38; N, 5.70. Found: C, 66.12; H, 7.25; N, 5.42.

The second isomer, compound 5: GC-MS ($R_t$=14.65 min) 401.25 ($M^+$+1, 0.2%), 400.25 ($M^+$, 0.8), 359.15 (0.4), 330.15 (0.4), 302.15 (3.1), 274.15 (8.0), 247.05 (21.7) 215.10 (13.0), 202.05 (7.0),153.15 (100), 126.15 (9.7); $\delta_H$ (400 MHz, $CDCl_3$) 0.93 (d, J=6.4 Hz, 3H), 1.15 (d, J=6.4 Hz, 3H), 2.14 (m, 2H), 2.37 (m, 1H), 2.60 (dd, J=11.6, 2.8 Hz, 1H), 2.84 (m, 2H), 2.96 (m, 1H), 3.35 (dd, J=13.2, 5.2 Hz, 1H), 5.13 (m, 2H), 5.81 (s, 1H), 5.86 (m, 1H), 6.73 (dd, J=8.0, 2.8 Hz, 1H), 6.81 (s, 1H), 6.84 (d, J=8.0 Hz, 1H), 7.16 (m, 1H), 7.40 (m, 3H), 7.70 (m, 2H), 7.80 (d, J=8.0 Hz, 1H), 8.15 (d, J=8.0 Hz, 1H); $\delta_{C-13}$ (100 MHz, $CDCl_3$ 15.7, 16.3, 38.8, 53.6, 55.0, 55.6, 56.8, 59.3, 63.6, 111.5, 115.6, 117.4, 121.9, 124.6, 125.0, 125.1, 125.4, 126.2, 127.4, 128.5, 128.9, 131.6, 133.9, 135.0, 138.3, 142.2, 159.4.

Its HCl salt: m.p. 150.5–153° C. (Ether); $v_{max}$ (KBr) $cm^{-1}$ 3483, 1600, 1262; Anal.Calcd.for $C_{27}H_{32}N_2O.2HCl.0.75H_2O$: C, 66.59; H, 7.35; N, 5.75. Found: C, 66.41; H, 7.03; N, 5.48.

Scheme 2

(±)-3-((αR*/S*)-α-((2S*,5R*)-4-Allyl-2,5-dimethyl-1-piperazinyl)-2-naphthyl)anisole (9 & 10).

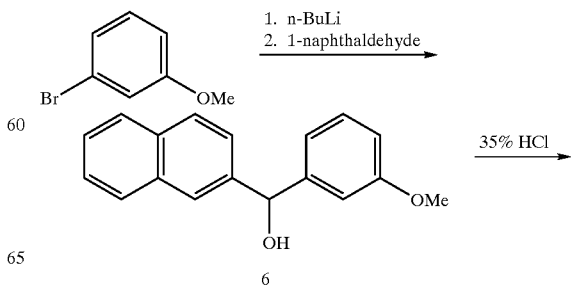

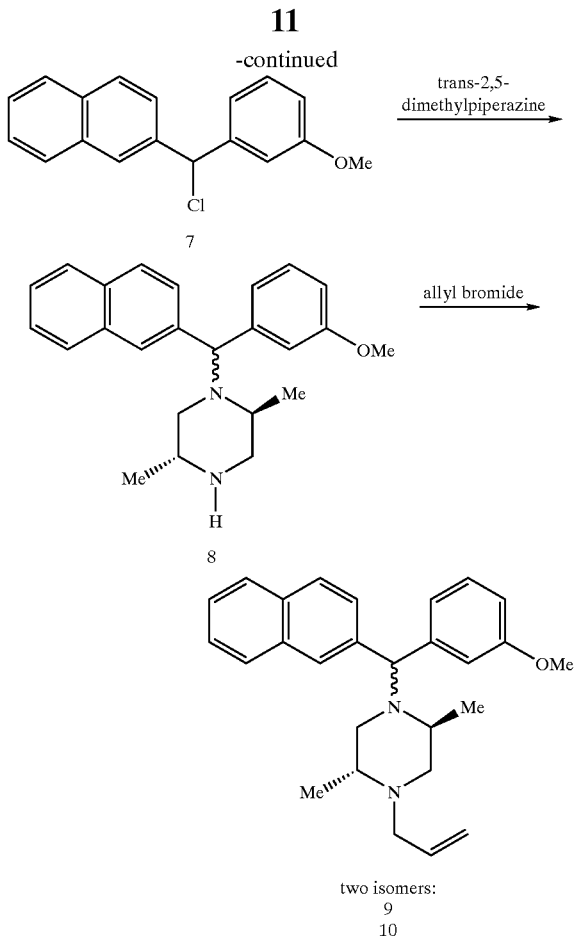

The compounds according to Examples 4–6 were synthesized as shown in Scheme 2 above.

B.

I. Preparation of 3-methoxy-α-(2-naphthyl)benzyl alcohol (Compound 6)

The compound 6 was prepared by following the synthesis procedure as described for compound 1, but substituting 1-naphtaldehyde for 2-naphtaldehyde.

GC-MS ($R_t$=10.68 min) 264 (M$^+$), 247, 231, 215, 202, 155, 135, 128, 109; $\delta_H$ (400 MHz, CDCl$_3$) 3.15 (brs, 1H), 3.59 (s, 3H), 5.71 (s, 1H), 6.69 (dd, J=8.4, 2.8 Hz, 1H), 6.87 (m, 2H), 7.11 (t, J=8.0 Hz, 1H), 7.29 (dd, J=8.4, 1.2 Hz, 1H), 7.35 (m, 2H), 7.63 (d, J=8.4 Hz, 1H), 7.70 (m, 3H); $\delta_{C\text{-}13}$ (100 MHz, CDCl3) 55.0, 75.9, 112.1, 112.8, 118.9, 124.6, 124.9, 125.7, 125.9, 127.5, 127.9, 128.1, 129.3, 132.7, 133.1, 141.0, 145.2, 159.5.

II. Preparation of 3-methoxy-α-(2-naphthyl)benzyl chloride (Compound 7)

The compound 7 was prepared by following the synthesis procedure as described for compound 2, but substituting compound 1 for compound 6.

GC-MS ($R_t$=10.58 min) 282 (M$^+$), 247, 231, 215, 202, 189, 151, 123, 101.

Example 4

Preparation of (±)-trans-1-(3-methoxy-α-(2-naphtbyl)benzyl)-2,5-dimethylpiperazine (Compound 8)

The compound 8 was prepared by following the synthesis procedure as described for compound 3, but substituting compound 2 for compound 7.

Used directly in the next step: GC-MS ($R_t$=14.03 min) 360 (M$^+$), 331, 301, 276, 247, 219, 169, 131, 113.

Example 5 and 6

Preparation of (±)-3-((αR*/S*)-α-((2S*,5R*)-4-Allyl-2,5-dimethyl-1-piperazinyl)-2-naphthyl) anisole (Compounds 9 & 10)

The compounds of these Examples were prepared by following the synthesis procedure as described for Examples 2 and 3, but substituting compound 3 for compound 8.

Compound 9 (one pure isomer): GC-MS ($R_t$=16.05 min) 401.25 (0.2%), 400.25 (0.8), 359.15 (0.4), 330.15 (0.4), 302.15 (3.1), 274.15 (8.0), 247.05 (21.7), 215.10 (13.0) 202.05 (7.0),153.15 (100), 126.15 (9.7); $\delta_H$ (400 MHz, CDCl$_3$) 1.36 (d, J=6.4 Hz, 3H), 1.41 (d, J=6.4 Hz, 3H), 3.16 (dd, J=13.2, 2.4 Hz, 1H), 3.26 (d, J=13.2 Hz, 1H), 3.46 (m, 1H), 3.86 (s, 3H), 3.94 (dd, J=11.2, 2.8 Hz, 1H), 4.10 (m, 2H), 4.46 (m, 2H), 5.58 (m, 2H), 5.78 (s, 1H), 6.05 (m, 1H), 6.96 (dd, J=8.0, 2.0 Hz, 1H), 7.18 (s, 1H), 7.33 (m, 1H), 7.44 (m, 1H), 7.50 (m, 2H), 7.83 (m, 3H), 8.04 (d, J=8.0 Hz, 1H), 8.13 (s, 1H), 13.6 (brs, 2H).

Its HCl salt: m.p. 129–138° C. (Ether); $\nu_{max}$ (KBr) cm$^{-1}$ 3426, 1600, 1262; Anal.Calcd.for C$_{27}$H$_{32}$N$_2$O.2HCl. 0.75H$_2$O: C, 66.59; H, 7.35; N, 5.75. Found: C, 66.80; H, 7.11; N, 5.42.

Compound 10 (a mixture of two isomers) Its HCl salt: m.p. 160–162.5° C. (Ether); $\nu_{max}$ (KBr) cm$^{-1}$ 3380, 1600, 1261; Anal.Calcd.for C$_{27}$H$_{32}$N$_2$O.2HCl. 0.50H$_2$O: C, 67.21; H, 7.31; N, 5.81. Found: C, 67.13; H, 6.97; N, 5.47.

Scheme 3

(±)-3-((αR*/S*)-α-((2S*,5R*)-4-Alkyl-2,5-dimethyl-1-piperazinyl)-2-benzofuranyl)anisole (14, 15, 16 & 17).

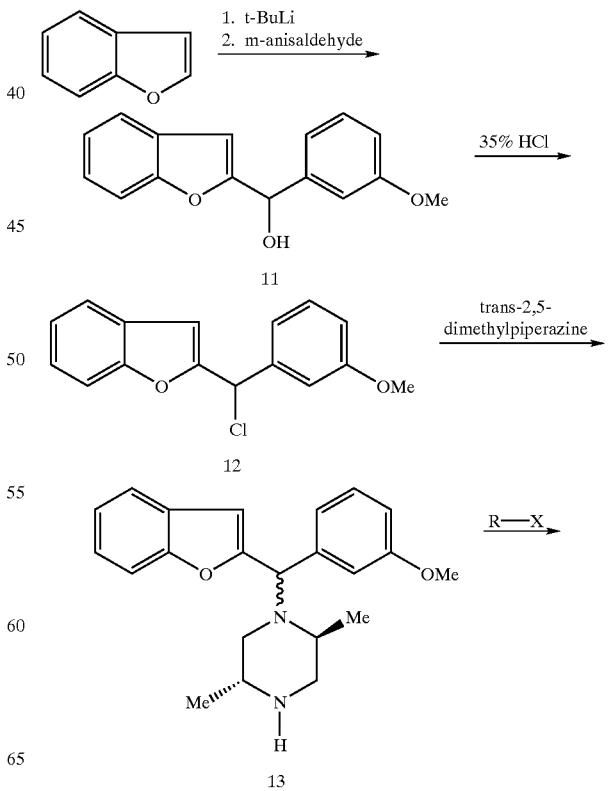

-continued

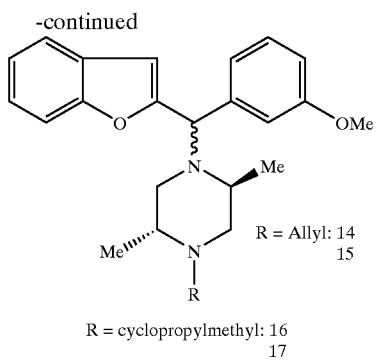

R = Allyl: 14
15

R = cyclopropylmethyl: 16
17

The compounds according to Examples 7–11 were synthesized as shown in Scheme 3 above.

C.
I. Preparation of 3-methoxy-α-(2-benzofuranyl)benzyl alcohol (Compound 11)

The compound of this Example was prepared by following the synthesis procedure as described for Example 1.

GC-MS ($R_t$=9.54 min) 254.15 (M$^+$, 100%), 237.10 (73.8), 221.05 (19.6), 194.10 (17.8), 165.10 (30.3), 147.05 (76.7), 135.10 (69.2), 118.10 (35.4), 108.10 (26.5), 91.10 (47.1); $\delta_H$ (400 MHz, CDCl$_3$) 3.21 (brs, 1H), 3.72 (s, 3H), 5.82 (s, 1H), 6.47 (s, 1H), 6.80–7.50 (m, 8H).

II. Preparation of 3-methoxy-α-(2-benzofuranyl)benzyl chloride (Compound 12)

The compound 12 was prepared by following the synthesis procedure as described for compound 2, but substituting compound 1 for compound 11.

GC-MS ($R_t$=9.08 min) 272.05 (M$^+$, 4.1%), 237.10 (100), 221.05 (4.5), 194.10 (14.7), 165.10 (23.1); $\delta_H$ (400 MHz, CDCl$_3$) 3.78 (s, 3H), 6.11 (s, 1H), 6.56 (s, 1H), 6.85–7.50 (m, 8H).

Example 7

Preparation of (±)-trans-1-(3-methoxy-α-(2'-benzofuranyl)benzyl)-2,5-dimethylpiperazine (Compound 13)

The compound 13 was prepared by following the synthesis procedure as described for compound 3, but substituting compound 2 for compound 12.

GC-MS ($R_t$=11.87 min & $R_t$=12.09 min) 351.15 (M$^+$+1, 2.2%), 350.15 (M$^+$, 8.6), 321.20 (0.4), 308.15 (0.2), 294.20 (18.3), 266.10 (58.6), 237.10 (100), 221.05 (3.0), 194.10 (10.0), 178.05 (4.1), 165.10 (13.0), 131.05 (2.9), 113.10 (43.8); $\delta_H$ (400 MHz, CDCl$_3$) (isomer at $R_t$=11.87 min) 0.92 (d, J=6.4 Hz, 3H), 1.20 (d, J=6.4 Hz, 3H), 1.92 (dd, J=11.2, 10.8 Hz, 1H), 2.44 (m, 1H), 2.69 (dd, J=11.2, 10.8 Hz, 1H), 2.83 (m, 2H), 2.90 (m, 1H), 3.78 (s, 3H), 5.56 (s, 1H), 6.61 (s, 1H), 6.80 (d, J=8.0 Hz, 1H), 7.00 (d, J=8.0 Hz, 1H), 7.10 (s, 1H), 7.24 (m, 3H), 7.46 (d, J=8.0 Hz, 1H), 7.56 (d, J=8.0 Hz, 1H); (isomer at $R_t$=12.09 min) 0.96 (d, J=6.4 Hz, 3H), 1.22 (d, J=6.4 Hz, 3H), 1.83 (dd, J=11.2, 10.8 Hz, 1H), 2.40 (m, 1H), 2.65 (m, 1H), 2.90 (m, 3H), 3.80 (s, 3H), 5.47 (s, 1H), 6.63 (s, 1H), 6.84 (m, 2H), 7.21 (m, 2H), 7.24 (m, 2H), 7.46 (d, J=8.0 Hz, 1H), 7.51 (d, J=8.0 Hz, 1H).

Its HCl salt: m.p. 115–125° C. (Ether); $v_{max}$ (KBr) cm$^{-1}$ 3373, 1595, 1257; Anal.Calcd.for $C_{22}H_{26}N_2O_2$.1.70HCl. 0.20H$_2$O: C, 63.51; H, 6.81; N, 6.73. Found: C, 63.60; H, 6.80; N, 6.70.

Example 8 and 9

Preparation of (±)-3-((αR*/S*)-α-((2S*5R*)-4-Allyl-2,5-dimethyl-1-piperazinyl)-2-benzofuranyl)anisole (Compounds 14 & 15)

The compounds of these Examples were prepared by following the synthesis procedure as described for Examples 2 and 3, but substituting compound 3 for compound 13.

The first isomer, compound 14: GC-MS ($R_t$=13.03 min) 390.20 (M$^+$, 1.5%), 349.15 (0.4), 320.10 (0.3), 292.10 (1.7), 264.10 (4.2), 237.10 (25.1), 221.05 (1.4), 194.10 (5.2), 165.10 (5.5), 153.15 (100), 126.15 (4.8), 98.05 (8.7), 84.10 (17.8); $\delta_H$ (400 MHz, CDCl$_3$) 0.97 (d, J=6.4 Hz, 3H), 1.21 (d, J=6.4 Hz, 3H), 2.12 (m, 2H), 2.35 (m, 1H), 2.65 (m, 1H), 2.75 (dd, J=11.6, 2.4 Hz, 1H), 2.81 (m, 3H), 3.42 (dd, J=13.6, 5.2 Hz, 1H), 3.78 (s, 3H), 5.14 (m, 2H), 5.51 (s, 1H), 5.85 (m, 1H), 6.61 (s, 1H), 6.81 (dd, J=8.0, 2.4 Hz, 1H), 7.01 (d, J=8.0 Hz, 1H), 7.11 (s, 1H), 7.24 (m, 3H), 7.44 (d, J=8.0 Hz, 1H), 7.54 (d, J=8.0 Hz, 1H); $\delta_{C-13}$ (100 MHz, CDCl$_3$) 17.2, 17.5, 53.1, 54.4, 55.2, 56.0, 56.6, 59.2, 60.4, 106.8, 111.3, 112.1, 114.2, 117.8, 120.6, 120.7, 122.6, 123.8, 128.1, 129.0, 134.8, 141.4, 154.9, 155.2, 159.6.

Its HCl salt: m.p. 122–128° C. (Ether); $v_{max}$ (KBr) cm$^{-1}$ 3490, 1602, 1253; Anal.Calcd.for $C_{25}H_{30}N_2O_2$.2HCl. 0.25H$_2$O: C, 64.17; H, 7.00; N, 5.99. Found: C, 64.27; H, 6.92; N, 5.92.

The second isomer, compound 15: GC-MS ($R_t$=13.23 min) 390.20 (M$^+$, 3.1%), 349.15 (0.5), 292.10 (2.2), 264.10 (5.5), 237.10 (33.2), 221.05 (1.8), 194.10 (7.1), 165.10 (7.7), 153.15 (100), 126.15 (7.1), 98.15 (18.4), 84.10 (25.0); $\delta_H$ (400 MHz, CDCl$_3$) 1.00 (d, J=6.4 Hz, 3H), 1.21 (d, J=6.4 Hz, 3H), 2.12 (m, 2H), 2.48 (m, 1H), 2.61 (m, 1H), 2.78 (dd, J=11.6, 2.4 Hz, 1H), 2.83 (m, 3H), 3.42 (dd, J=13.6, 5.6 Hz, 1H), 3.79 (s, 3H), 5.15 (m, 2H), 5.40 (s, 1H), 5.85 (m, 1H), 6.64 (s, 1H), 6.86(m, 3H), 7.20 (m, 3H), 7.44 (d, J=8.0 Hz, 1H), 7.50 (d, J=8.0 Hz, 1H).

Its HCl salt: m.p. 97–104° C. (Ether); $v_{max}$ (KBr) cm$^{-1}$ 3438, 1601 (s), 1260; Anal.Calcd.for $C_{25}H_{30}N_2O_2$.2HCl. 0.50H$_2$O: C, 63.56; H, 7.04; N, 5.93. Found: C, 63.70; H, 6.68; N, 5.83.

Example 10 and 11

Preparation of (±)-3-((αR*/S*)-α-((2S*,5R*)-4-Cyclopropylmethyl-2,5-dimethyl-1-piperazinyl)-2-benzofuranyl)anisole (Compounds 16 & 17)

The compounds of these Examples were prepared by following the synthesis procedure as described for Examples 2 and 3, except using cyclopropyl methyl iodide and substituting compound 3 for compound 13.

The first isomer, compound 16: GC-MS ($R_t$=14.87 min) 405.25 (M$^+$+1, 2.3%), 404.25 (M$^+$, 8.2), 362.20 (0.5), 349.15 (0.4), 320.20 (0.8), 292.20 (4.1), 291.10 (3.4), 265.10 (16.5), 237.10 (65.9), 194.10 (11.5), 167.20 (100), 140.20 (3.9), 124.15 (4.6), 98.15 (44.0); $\delta_H$ (400 MHz, CDCl$_3$) 0.05 (m, 2H), 0.46 (m, 2H), 0.80 (m, 1H), 0.92 (d, J=6.0 Hz, 3H), 1.21 (d, J=6.0 Hz, 3H), 2.01 (dd, J=12.8, 7.2 Hz, 1H), 2.17 (m, 2H), 2.35 (m, 1H), 2.64 (dd, J=13.2, 6.4 Hz, 1H), 2.66 (m, 1H), 2.72 (dd, J=12.0, 2.4 Hz, 1H), 3.04 (dd, J=11.2, 3.2 Hz, 1H), 3.75 (s, 3H), 5.50 (s, 1H), 6.58 (s, 1H), 6.79 (dd, J=8.0, 2.4 Hz, 1H 7.01 (d, J=8.0 Hz, 1H), 7.09 (s, 1H), 7.20 (m, 3H), 7.41 (d, J=8.0 Hz, 1H), 7.51 (m, 1H): $\delta_{C-13}$ (100 MHz, CDCl$_3$) 3.2, 4.7, 7.4, 17.4, 17.7, 53.1, 54.5, 55.2, 56.0, 58.3, 59.2, 60.8, 106.8, 111.3, 112.0, 114.2, 120.6, 120.7, 122.6, 123.7, 128.0, 129.0, 141.4, 154.8, 155.2, 159.6.

Its HCl salt: m.p. 162–164° C. (Ether): $v_{max}$ (KBr) cm$^{-1}$ 3414, 1599, 1255; Anal.Calcd.for $C_{26}H_{32}N_2O_2$.2HCl. 0.5H$_2$O: C, 64.19; H, 7.25; N, 5.76. Found: C, 64.43; H, 7.30; N, 5.78.

The second isomer, compound 17: GC-MS (R$_t$=15.17 min) 405.25 (M$^+$+1, 2.2%), 404.25 (M$^+$, 8.9), 362.10 (0.6), 349.15 (0.4), 320.10 (0.8), 292.10 (5.0), 291.10 (3.9), 265.10 (19.4), 237.10 (72.2), 194.10 (12.8), 167.20 (100), 140.10 (3.9), 124.15 (4.8), 98.15 (45.5); δ$_H$ (400 MHz, CDCl$_3$) 0.08 (m, 2H), 0.48 (m, 2H), 0.82 (m, 1H), 0.97 (d, J=6.4 Hz, 3H), 1.25 (d, J=6.4 Hz, 3H), 2.10 (m, 2H), 2.28 (dd, J=11.2, 10.0 Hz, 1H) 2.49 (m, 1H), 2.62 (dd, J=13.2, 6.0 Hz, 1H), 2.63 (m, 1H), 2.83 (dd, J=11.2, 2.8 Hz, 1H), 3.02 (dd, J=11.2, 3.2 Hz, 1H), 3.78 (s, 3H), 5.43 (s, 1H), 6.64 (s, 1H), 6.87 (m, 3H), 7.21 (m, 3H), 7.45 (dd, J=7.6, 1.2 Hz, 1H), 7.50 (m, 1H); δ$_{C-13}$ (100 MHz, CDCl$_3$) 3.3, 4.6, 7.4, 17.0, 17.6, 52.6, 55.2, 55.4, 55.6, 58.3, 60.3, 61.6, 105.7, 111.3, 112.5, 115.9, 120.5, 122.1, 112.5, 123.5, 128.4, 128.9, 137.3, 155.0, 158.3, 159.3.

Its HCl salt: m.p. 92–105° C. (Ether); ν$_{max}$ (KBr) cm$^{-1}$ 3398, 1599, 1257; Anal.Calcd.for C$_{26}$H$_{32}$N$_2$O$_2$·0.2HCl·0.5H$_2$O: C, 64.19; H, 7.25; N, 5.76. Found: C, 64.38; H, 7.14; N, 5.73.

Scheme 4

(±)-3-((αR*/S*)-α-((2S*,5R*)-4-Alkyl-2,5-dimethyl-1-piperazinyl)-6-quinolinyl)anisole (22, 23, 24 & 25).

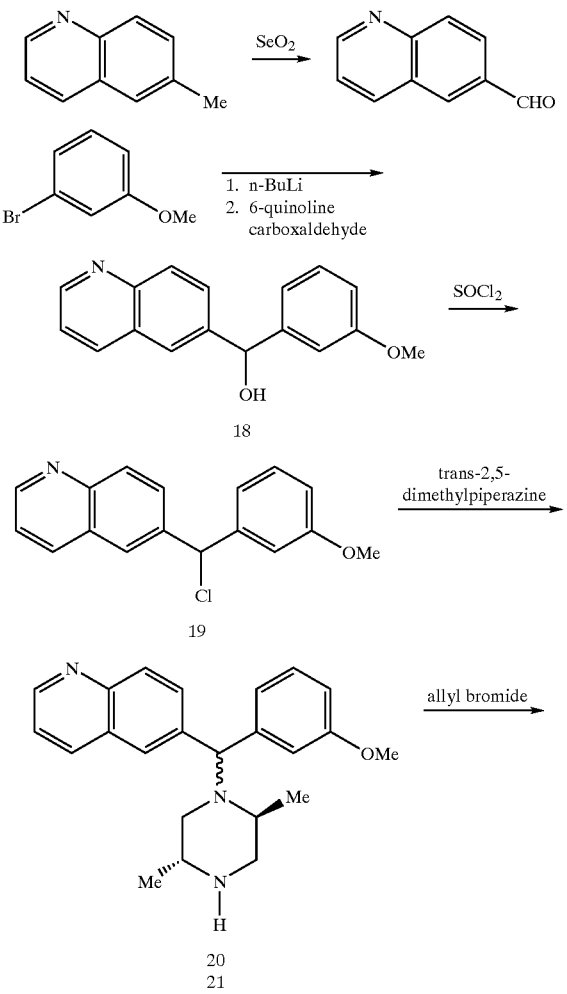

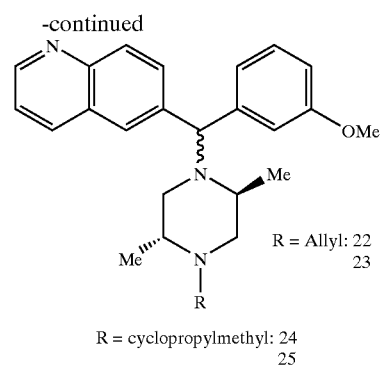

R = cyclopropylmethyl: 24
25

D.
I. Preparation of 6-Quinolinecarboxaldehyde

A mixture of 6-methylquinoline (5.72 g, 40.0 mmol) and selenium oxide (4.44 g, 40.0 mmol) was heated to 220° C. for 1 h. After cooling down the residue was dissolved in ethyl acetate (100 mL). The organic solution was washed with brine, dried over MgSO$_4$. Evaporation of solvents provided a solid, which was recrystalized from ether-hexane (1:1) mixture to give 6-quinolinecarboxaldehyde (3.45 g, 55%).

GC-MS (R$_t$=5.29 min) 157.15 (M$^+$, 100%), 156.15 (92.2), 128.15 (62.9), 101.15 (16.0) δ$_H$ (400 MHz, CDCl$_3$) 7.53 (m, 1H), 8.21 (m, 2H), 8.33 (m, 2H), 9.06 (m, 1H), 10.21 (s, 1H); 67 $_{C-13}$ (100 MHz, CDCl$_3$) 122.1, 126.6, 127.6, 130.7, 133.5, 134.2, 137.3, 150.8, 153.0, 191.3.

The compounds according to Examples 12–17 were synthesized as shown in Scheme 4 above.

II. Preparation of 3-methoxy-α-(6-quinolinyl)benzyl alcohol (Compound 18)

The compound 18 was prepared by following the synthesis procedure as described for compound 1, but substituting 1-naphtaldehyde for 6-quinolinecarboxaldehyde.

GC-MS (R$_t$=11.13 min) 265.10 (M$^+$, 49.0%), 248.05 (2.3), 204.05 (9.7), 156.05 (37.6), 135.00 (100), 109.00 (43.5); δ$_H$ (400 MHz, CDCl$_3$) 3.73 (s, 3H), 5.94 (s, 1H), 6.78 (d, J=8.4 Hz, 1H), 6.95 (m, 2H), 7.22 (m, 1H), 7.31 (m, 1H), 7.61 (d, J=8.4 Hz, 1H), 7.83 (s, 1H), 7.95 (d, J=8.4 Hz, 1H), 8.07 (d, J=8.0 Hz, 1H), 8.73 (m, 1H); δ$_{C-13}$ (100 MHz, CDCl$_3$) 55.2, 75.7, 112.3, 113.1, 119.1, 121.2, 124.6, 128.5, 129.4, 129.6, 136.3, 142.1, 145.2, 147.6, 150.1, 159.8.

III. Preparation of 3-methoxy-α-(6-quinolinyl)benzyl chloride (Compound 19)

The compound 19 was prepared by following the synthesis procedure as described for compound 2, but substituting compound 1 for compound 18.

Used directly in the next step: δ$_H$ (400 MHz, CDCl$_3$) 3.73 (s, 3H), 5.98 (s, 1H), 6.8–8.2 (m, 9H), 8.80 (s, 1H).

Example 12 and 13

Preparation of (±)-trans-1-(3-methoxy-α-(6'-quinolinyl)benzyl)-2,5-dimethylpiperazine (Compounds 20 & 21)

The compounds of these Examples were prepared by following the synthesis procedure as described for compound 3, but substituting compound 2 for compound 19.

GC-MS (R$_Y$=14.91 min) 361.20 (M$^+$, 0.8%), 332.15 (0.3), 306.15 (0.6), 302.15 (14.4), 277.15 (52.5), 248.05 (100), 233.00 (10.6), 204.05 (17.1), 176.05 (2.7), 151.05 (1.4), 142.10 (1.8), 113.10 (19.9).

The first isomer, compound 20: δ$_H$ (400 MHz, CDCl$_3$) 1.06 (d, J=6.4 Hz, 3H), 1.24 (d, J=6.4 Hz, 3H), 1.84 (dd, J=11.6, 9.2 Hz, 1H), 2.60 (m, 2H), 2.77 (m, 2H), 3.06 (m, 2H), 3.80 (s, 3H), 5.44 (s, 1H), 6.77 (s, 1H), 6.83 (d, J=8.0 Hz, 1H), 6.88 (dd, J=8.0, 2.4 Hz, 1H), 7.31 (m, 1H), 7.37 (m, 1H), 7.82 (s, 1H), 7.84 (m, 1H), 8.03 (d, J=8.8 Hz, 1H), 8.09 (d, J=8.8 Hz, 1H), 8.87 (m, 1H).

Compound 21 (a mixture of two isomers, ~25% compound 20): $\delta_H$ (400 MHz, CDCl$_3$) 1.20 (m, 6H), 2.05 (m, 1H), 2.73 (m, 2H), 2.87 (m, 1H), 3.13 (m, 2H), 3.73 & 3.76 (s, 3H), 5.38 (s, 1H), 6.38 (brs, NH), 6.70–8.15 (m, 9H), 8.84 (m, 1H).

Example 14

Preparation of (±)-3-((αR*/S*)-α-((2S*,5R*)-4-Allyl-2,5-dimethyl-1-piperazinyl)-6-quinolinyl) anisole (Compound 22)

The compound of this Example was prepared by following the synthesis procedure as described for Examples 2 and 3, but substituting compound 3 for compound 20.

GC-MS (R$_t$=17.22 min) 401.25 (M$^+$, 0.3%), 360.20 (0.3), 331.10 (0.2), 303.20 (1.7), 276.10 (4.5), 248.10 (17.2), 233.10 (4.5), 204.10 (8.0), 176.10 (1.3), 153.20 (100), 126.20 (5.4); $\delta_H$ (400 MHz, CDCl$_3$) 1.0 (d, J=6.4 Hz, 3H), 1.21 (d, J=6.4 Hz, 3H), 1.99 (m, 1H), 2.20 (m, 1H), 2.56 (m, 1H), 2.66 (m, 1H), 2.71 (m, 1H), 2.85 (m, 1H), 2.90 (m, 1H), 3.37 (dd, J=13.2, 4.0 Hz, 1H), 3.78 (s, 3H), 5.17 (m, 2H), 5.35 (s, 1H), 5.87 (m, 1H), 6.82 (m, 3H), 7.26 (t, J=7.6 Hz, 1H), 7.36 (m, 1H), 7.81 (s, 1H), 7.88 (d, J=8.8 Hz, 1H), 8.03 (d, J=8.8 Hz, 1H), 8.09 (d, J=7.6 Hz, 1H), 8.87 (m, 1H); $\delta_{C-13}$ (100 MHz, CDCl$_3$) 15.7, 16.4, 52.0, 53.7, 55.2, 55.5, 56.8, 58.9, 65.9, 112.1, 116.3, 117.8, 120.9, 122.5, 126.5, 127.9, 128.9, 129.0, 130.2, 134.8, 136.0, 139.2, 141.1, 147.6, 150.0, 159.5.

Its HCl salt: m.p. 128–140° C. (Ether); $\nu_{max}$ (KBr) cm$^{-1}$ 3376, 1596, 1263; Anal.Calcd.for C$_{26}$H$_{31}$N$_3$O.2.30HCl. 0.1H$_2$O: C, 64.10; H, 6.93; N, 8.62. Found: C, 64.08; H, 6.92; N, 8.35.

Example 15

Preparation of (±)-3-((αR*/S*)-α-((2S*,5R*)-4-Allyl-2,5-dimethyl-1-piperazinyl)-6-quinolinyl) anisole (Compound 23)

The compound of this Example was prepared by following the synthesis procedure as described for Examples 2 and 3, but substituting compound 3 for compound 21.

GC-MS (R$_t$=17.21 min) 401.35 (M$^+$, 0.4%), 360.30 (0.2), 331.20 (0.2), 303.20 (1.6), 276.10 (4.8), 248.10 (17.3), 233.10 (4.4), 204.10 (8.1), 176.10 (1.3), 153.20 (100), 126.20 (5.6); $\delta_H$ (400 MHz, CDCl$_3$) 1.01 (d, J=6.0 Hz, 3H), 1.21 (d, J=6.0 Hz, 3H), 1.95 (m, 1H), 2.16 (m, 1H), 2.56 (m, 1H), 2.66 (m, 1H), 2.74 (m, 1H), 2.80 (m, 1H), 2.87 (m, 1H), 3.30 (dd, J=13.6, 5.6 Hz, 1H), 3.77 (s, 3H), 5.13 (m, 2H), 5.34 (s, 1H), 5.82 (m, 1H), 6.77 (dd, J=8.0, 2.4 Hz, 1H), 6.99 (d, J=7.6 Hz, 1H), 7.11 (s, 1H), 7.21 (d, J=8.0 Hz, 1H), 7.38 (dd, J=8.4, 4.0 Hz, 1H), 7.59 (d, J=8.4 Hz, 1H), 7.66 (s, 1H), 8.03 (d, J=8.8 Hz, 1H), 8.11 (d, J=8.4 Hz, 1H), 8.88 (m, 1H); $\delta_{C-13}$ (100 MHz, CDCl$_3$) 15.3, 16.2, 51.9, 53.4, 55.2, 55.3, 56.8, 58.5, 66.1, 111.8, 114.0, 117.6, 120.6, 121.1, 127.9, 128.3, 128.9, 129.1, 131.4, 134.9, 136.0, 137.1, 144.1, 147.7, 150.2, 159.6.

Its HCl salt: m.p. 177–182° C. (Ether); $\nu_{max}$ (KBr) cm$^{-1}$ 3405, 1597, 1260; Anal.Calcd.for C$_{26}$H$_{31}$N$_3$O.2.80HCl: C, 62.01; H, 6.76; N, 8.34. Found: C, 61.98; H, 6.77; N, 8.03

Example 16 and 17

Preparation of (±)-3-((αR*/S*)-α-((2S*,5R*)-4-Cyclopropylmethyl-2,5-dimethyl-1-piperazinyl)-6-quinolinyl)anisole (Compounds 24 & 25)

The compounds of these Examples were prepared by following the synthesis procedure as described for Examples 2 and 3, but substituting allylbromide for cyclopropylmethylioidide.

The first isomer, compound 24: GC-MS (R$_t$=20.77 min) 415.25 (M$^+$, 3.8%), 344.15 (2.4), 302.10 (9.5), 276.10 (58.8), 248.15 (79.1), 233.10 (17.2), 204.10 (29.4), 176.10 (4.2), 167.15 (100), 138.15 (14.2), 112.15 (47.0); $\delta_H$ (400 MHz, CDCl$_3$) 0.10 (m, 2H), 0.51 (m, 2H), 0.86 (m, 1H), 0.97 (d, J=6.4 Hz, 3H), 1.25 (d, J=6.4 Hz, 3H), 1.98 (dd, J=11.2, 8.8 Hz, 1H), 2.14 (dd, J=13.2, 6.4 Hz, 1H), 2.32 (dd, J=10.8, 5.6 Hz, 1H), 2.58 (m, 2H), 2.66 (dd, J=11.6, 2.8 Hz, 1H), 2.73 (m, 1H), 3.07 (dd, J=11.2, 3.2 Hz, 1H), 3.78 (s, 3H), 5.39 (s, 1H), 6.79 (s, 1H), 6.84 (m 2H), 7.26 (t, J=8.0 Hz, 1H), 7.35 (dd, J=8.4, 4.0 Hz, 1H), 7.83 (s, 1H), 7.89 (d, J=8.8 Hz, 1H), 8.03 (d, J=9.2 Hz, 1H), 8.09 (d, J=8.0 Hz, 1H), 8.86 (dd, J=4.0, 2.0 Hz, 1H); $\delta_{C-13}$ (100 MHz, CDCl$_3$) 3.4, 4.4, 7.6, 16.2, 16.9, 52.1, 53.8, 55.2, 55.6, 58.5, 59.7, 65.6, 112.0, 116.3, 120.9, 122.6, 126.5, 127.9, 128.8, 129.0, 130.2, 136.0, 139.1, 141.1, 147.6, 149.9, 159.4.

Its HCl salt: m.p. 127–157° C. (Ether); $\nu_{max}$ (KBr) cm$^{-1}$ 3402, 1596, 1262; Anal.Calcd.for C$_{27}$H$_{33}$N$_3$O.3HCl. 0.75H$_2$O: C, 60.23; H, 7.02; N, 7.80. Found: C, 60.49; H, 7.00; N, 7.73.

The second isomer, compound 25: GC-MS R$_t$=20.73 min) 415.25 (M$^+$, 3.2%), 344.05 (2.3), 302.10 (7.7), 276.10 (48.5), 248.15 (69.6), 233.10(15.7), 204.10 (25.8), 176.10 (3.7), 167.15 (100), 138.15 (12.2), 112.15 (46.8); $\delta_H$ (400 MHz, CDCl$_3$) 0.17 (m, 2H), 0.56 (m, 2H), 0.97 (m, 1H), 1.11 (brs, 3H), 1.27 (brs, 3H), 2.24 (m, 1H), 2.38 (m, 1), 2.51 (m, 1H), 2.61 (m, 1H), 2.87 (m, 3H), 3.13 (m, 1H), 3.77 (s, 3H), 5.34 (s, 1H), 6.78 (d, J=8.0 Hz, 1H), 6.98 (d, J=8.0 Hz, 1H), 7.08 (s, 1H), 7.22 (t, J=8.0 Hz, 1H), 7.39 (dd, J=8.4, 4.4 Hz, 1H), 7.60 (d, J=8.4 Hz, 1H), 7.73 (s, 1H), 8.04 (d, J=8.8 Hz, 1H), 8.16 (d, J=8.4 Hz, 1H), 8.89 (d, J=4.0 Hz, 1H); $\delta_{C-13}$ (100 MHz, CDCl$_3$) 4.07, 4.37, 6.9, 14.8, 15.1, 51.4, 55.2, 56.2, 58.2, 60.3, 66.4, 111.8, 114.2, 120.6, 121.2, 128.0, 128.1, 129.2, 131.0, 136.0, 137.0, 143.8, 147.7, 150.3, 159.6.

Its HCl salt: m.p. 92–105° C. (Ether); $\nu_{max}$ (KBr) cm$^{-1}$ 3345, 1596, 1259.

Scheme 5

(±)-3-((αR*/S*)-α-((2S*,5R*)-4-Alkyl-2,5-dimethyl-1-piperazinyl)-4-quinolinyl)anisole (29 & 30).

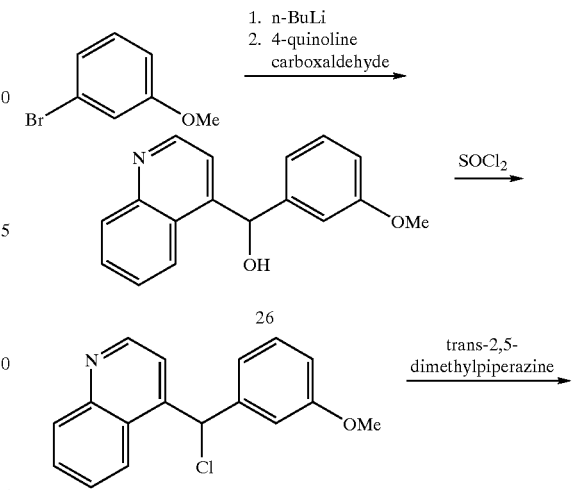

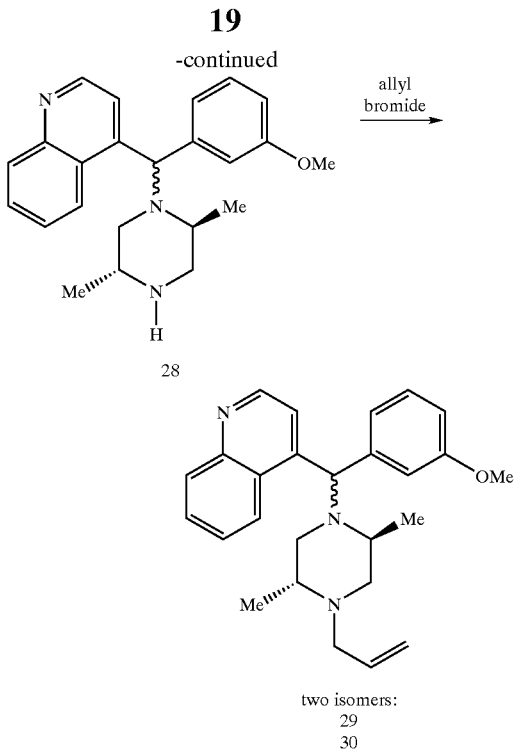

28 two isomers:
29
30

The compounds according to Examples 18–20 were synthesized as shown in Scheme 5 above.

E.

I. Preparation of 3-methoxy-α-(4-quinolinyl)benzyl alcohol (Compound 26)

The compound 26 was prepared by following the synthesis procedure as described for compound 1, but substituting 1-naphtaldehyde for 4-quinolinecarboxaldehyde.

GC-MS ($R_t$=10.81 min) 266.10 (M$^+$+1, 11.8%), 265.10 (M$^+$, 61.0), 248.05 (6.1), 232.00 (6.2), 216.05 (4.7), 204.00 (10.5), 191.05 (2.0), 176.00 (3.8), 156.00 (13.9), 135.10 (100), 129.10 (86.6), 109.10 (68.2), 102.10 (25.5); $\delta_H$ (400 MHz, CDCl$_3$) 3.67 (s, 3H), 5.30 (brs, 1H), 6.41 (s, 1H), 6.76 (d, J=7.2 Hz, 1H), 6.90 (m, 2H), 7.18 (t, J=7.6 Hz, 1H), 7.38 (m, 1H), 7.56 (t, J=7.6 Hz, 1H), 7.62 (m, 1H), 7.92 (d, J=8.4 Hz, 1H), 8.00 (d, J=8.4 Hz, 1H), 8.64 (dd, J=4.4, 1.2 Hz, 1H); $\delta_{C-13}$ (100 MHz, CDCl$_3$) 55.1, 72.1, 113.0, 113.2, 118.5, 119.5, 123.9, 125.7, 126.5, 129.0, 129.5, 129.7, 143.8, 147.8, 149.1, 149.9, 159.7.

II. Preparation of 3-methoxy-α-(4-quinolinyl)benzyl chloride (Compound 27)

The compound 27 was prepared by following the synthesis procedure as described for compound 2, but substituting compound 1 for compound 26.

Used directly in the next step: GC-MS ($R_t$=10.54 min) 285.10 (M$^+$+, 2, 11.5%), 283.10 (M$^+$, 33.10), 268.05 (0.2), 248.15 (100), 233.10 (37.0), 217.05 (27.2), 204.10 (45.5), 178.10 (5.9), 176.10 (11.5), 151.10 (5.7), 139.05 (2.1), 108.60 (11.0), 102.10 (17.4).

Example 18

Preparation of (±)-trans-1-(3-methoxy-α-(4-quinolinyl)benzyl)-2,5-dimethylpiperazine (Compound 28)

The compound of this Example was prepared by following the synthesis procedure as described for compound 3, but substituting compound 2 for compound 27.

GC-MS ($R_t$=13.96 min) 362.20 (M$^+$+1, 1.4%), 361.20 (M$^+$, 6.6), 306.10 (2.0), 302.15 (18.3), 277.15 (59.6), 248.15 (100), 233.10 (15.8), 204.10 (20.9), 176.10 (3.8), 151.00 (1.8), 143.15 (1.4), 113.15 (15.8); $\delta_H$ (400 MHz, CDCl$_3$) 0.92 (d, J=6.4 Hz, 3H), 1.12 (d, J=6.4 Hz, 3H), 1.82 (dd, J=11.6, 10.0 Hz, 1H), 2.52 (brs, 1H), 2.62 (dd, J=11.6, 2.8 Hz, 1H), 2.72 (m, 1H), 2.77 (m, 1H), 2.88 (m, 1H), 2.98 (dd, J=11.6, 2.0 Hz, 1H), 3.72 (s, 3H), 5.86 (s, 1H), 6.69 (s, 1H), 6.72 (d, J=8.0 Hz, 1H), 6.78 (dd, J=8.0, 2.4 Hz, 1H), 7.20 (t, J=8.0 Hz, 1H), 7.37 (t, J=8.0 Hz, 1H), 7.60 (t, J=8.0 Hz, 1H), 7.65 (d, J=4.4 Hz, 1H), 7.99 (d, J=8.8 Hz, 1H), 8.09 (d, J=8.0 Hz, 1H), 8.89 (d, J=4.4 Hz, 1H).

Example 19 and 20

Preparation of (±)-3-((αR*/S*)-α-((2S*,5R*)-4-Allyl-2,5-dimethyl-1-piperazinyl)-4-quinolinyl) anisole (Compounds 29 & 30)

The compounds of these Examples were prepared by following the synthesis procedure as described for Examples 2 and 3, but substituting compound 3 for compound 28.

The first isomer, compound 29: GC-MS ($R_t$=15.97 min) 401.15 (M$^+$, 0.8%), 360.20 (0.8), 303.15 (3.3), 27615 (5.7), 248.05 (15.3), 217.05 (6.3), 204.10 (10.4), 176.00 (2.2), 153.20 (100), 126.10 (5.3), 98.10 (13.8); $\delta_H$ (400 MHz, CDCl$_3$) 0.96 (d, J=6.0 Hz, 3H), 1.14 (d, J=6.0 Hz, 3H), 2.01 (m, 1H), 2.16 (t, J=10.0 Hz, 1H), 2.47 (m, 1H), 2.59 (d, J=11.2 Hz, 1H), 2.86 (m, 2H), 2.95 (t, J=6.0 Hz, 1H), 3.36 (dd, J=13.6, 4.4 Hz, 1H), 3.72 (s, 3H), 5.15 (m, 2H), 5.77 (s, 1H), 5.85 (m, 1H), 6.74 (m, 3H), 7.17 (t, J=7.6 Hz, 1H), 7.38 (t, J=8.0 Hz, 1H), 7.60 (dd, J=7.2, 0.8 Hz, 1H), 7.73 (d, J=4.4 Hz, 1H), 8.00 (d, J=8.4 Hz, 1H), 8.08 (d, J=8.8 Hz, 1H), 8.90 (d, J=3.6 Hz, 1H); $\delta_{C-13}$ (100 MHz, CDCl$_3$) 15.9, 16.6, 53.8, 55.1, 55.5, 56.7, 59.4, 63.2, 112.0, 115.7, 117.7, 120.6, 121.9, 124.4, 126.0, 126.8, 128.6, 129.3, 130.1, 134.8, 140.3, 148.5, 148.6, 150.2, 159.5.

Its HCl salt: m.p. 158–166° C. (AcOEt-Ether); $v_{max}$ (KBr) cm$^{-1}$ 3400, 1596, 1263: Anal.Calcd.for C$_{26}$H$_{31}$N$_3$O.3.0HCl.0.9H$_2$O: C, 59.24; H, 6.85; N, 7.97. Found: C, 59.31; H, 6.94; N, 7.80.

The second isomer, compound 30: GC-MS ($R_t$=16.19 min) 401.25 (M$^+$, 0.5%), 386.20 (0.2), 360.20 (0.7), 331.10 (0.3), 303.15 (3.3), 276.15 (4.7), 248.15 (13.7), 233.10 (5.8), 217.05 (4.9), 204.10 (9.8), 176.10 (1.8), 153.20 (100), 126.20 (5.2), 98.10 (13.9); $\delta_H$ (400 MHz, CDCl$_3$); $\delta_{C-13}$ (100 MHz, CDCl$_3$).

Its HCl salt: m.p. 155–165° C. (AcOEt-Ether).

Scheme 6

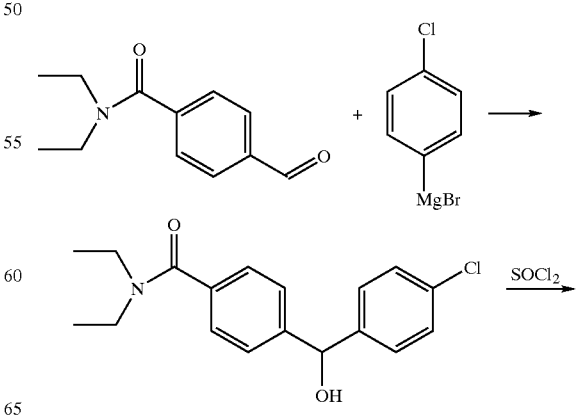

31

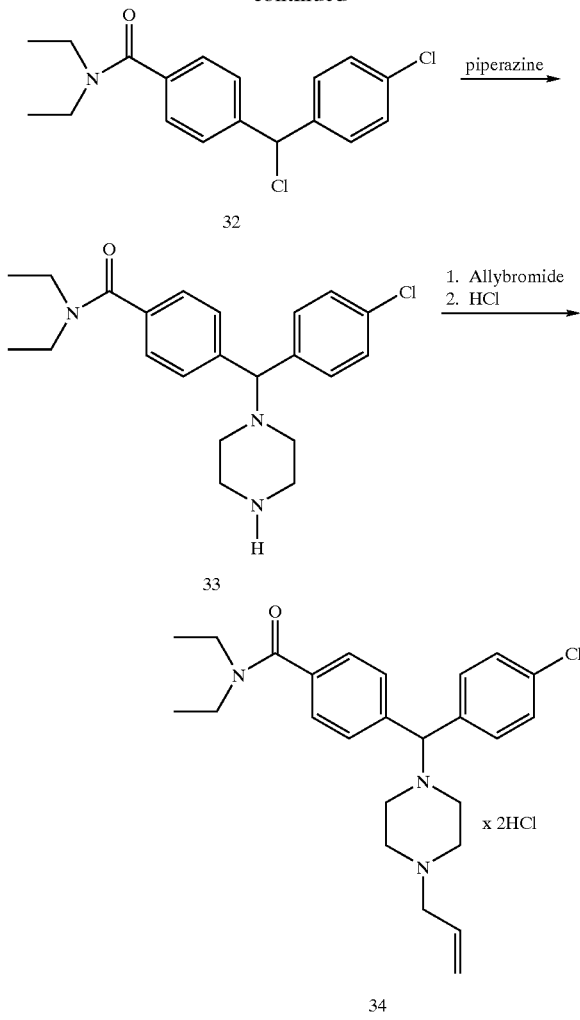

Used for the next step without further purification.

Example 21

Preparation of (±) 4-((α-(1-Piperazinyl))-4chlorobenzyl)-N,N-diethylbenzamide (Compound 33)

The compound of this Example was prepared by following the synthesis procedure as described for compound 3, but substituting compound 2 for compound 32.

m.p. 112–113° C. (from acetonitrile), $v_{max}$ (KBr)/cm$^{-1}$ 3347, 2947, 2809, 1615, 1451, 1318, 1284, 1094, 836; $\delta_H$ (400 MHz, CDCl$_3$) 1.10 (3H, br s), 1.21 (3H, br s), 1.69 (1H, br s), 2.33 (4H, br s), 2.86–2.89 (4H, m), 3.24 (2H, br s), 3.51 (2H, br s), 4.22 (1H, s), 7.23–7.41 (8H, m); $C_{22}H_{28}N_3OCl.0.3\ H_2O$ requires: C, 67.52; H, 7.37; N, 10.74. Found: C, 67.68; H, 7.37; N, 10.73.

Example 22

Preparation of (±) 4-((α-((4-Allyl)-1-piperazinyl))-4-chlorobenzyl)-N,N-diethylbenzamide.2HCl (Compound 34)

The compound of this Example was prepared by following the synthesis procedure as described for Examples 2 and 3, but substituting compound 3 for compound 33.

m.p. 147–163° C. (from ether), $v_{max}$ (KBr)/cm$^{-1}$ 3418, 2974, 2355, 1626, 1435, 1286, 1092, 945, 812; $\delta_H$ (400 MHz, CDCl$_3$) 1.06 (3H, br s), 1.19 (3H, br s), 3.0–3.7 (14H, m), 5.4–5.6 (2H, m), 6.0–6.2 (1H, br m), 7.2–7.8 (9H, m): $C_{25}H_{34}N_3OCl_3$ requires: C, 60.18; H, 6.87; N, 8.42. Found: C, 60.48; H, 6.89; N, 8.31.

The compounds according to Examples 21–22 were synthesized as shown in Scheme 6 above.

E.

I. Preparation of (±) 4-((α-Hydroxy)-4-chlorobenzyl)-N,N-diethylbenzamide (Compound 31)

4-Formyl-N,N-diethylbenzamide (2.088 g, 10.1 mmol) was dissolved in 45 ml of anhydrous THF. The solution was cooled down to −78° C., followed by a dropwise addition of 10.1 ml (10.1 mmol) of a 1.0 M solution of 4-Chlorophenylmagnesium bromide in ether. The mixture was warmed up to room temperature within 3 hours. Then 50 ml of a saturated NH$_4$Cl-solution was added and the mixture was extracted with ethyl acetate (3×30 ml). The combined organic layers were washed with water (2×30 ml) and brine (1×30 ml), dried (Na$_2$SO$_4$), filtered and the solvent was removed in vacua. The residue was chromatographed on silica gel eluting with methanol:dichloromethane (1:125–3:125) to yiled the title compound as a colorless oil.

$v_{max}$ (KBr)/cm$^{-1}$ 3329, 2977, 1595, 1461, 1289, 1094, 1051, 830; $\delta_H$ (400 MHz, CDCl$_3$) 1.09 (3H, br s), 1.21 (3H, br s), 3.22 (2H, br s), 3.33 (1H, d, J 3), 3.50 (2H, br s), 5.74 (1H, d, J 3), 7.22–7.34 (m, 8H);

II. Preparation of (±) 4-((α-Chloro)-4-chlorobenzyl)-N,N-diethylbenzamide (Compound 32)

The compound 32 was prepared by following the synthesis procedure as described for compound 2, but substituting compound 1 for compound 31.

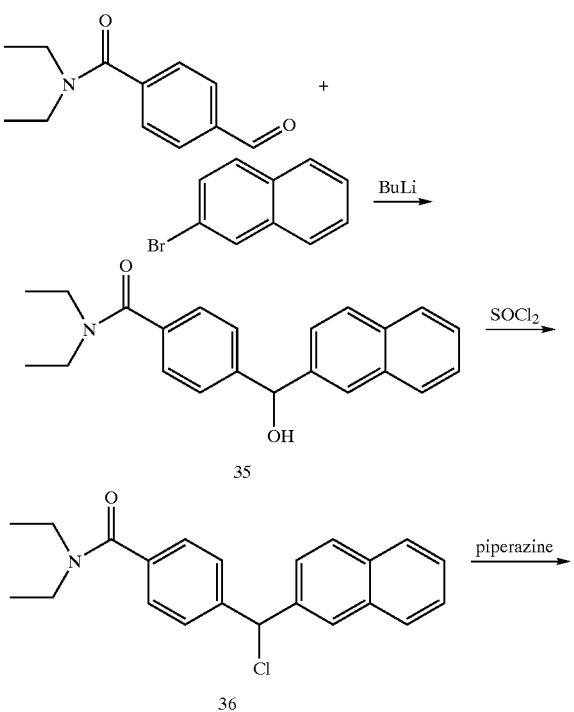

Scheme 7

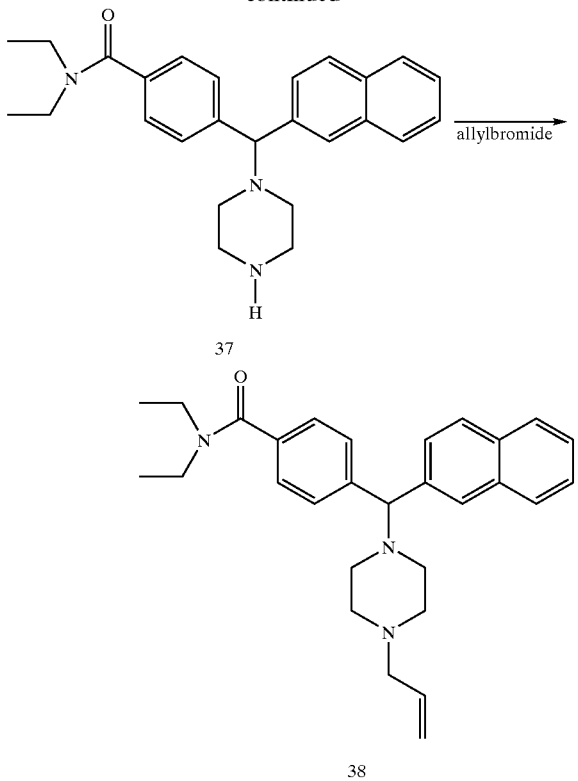

The compounds according to Examples 23–24 were synthesized as shown in Scheme 7 above.

G.
I. Preparation of (±) 4-((α-Hydroxy)-2-naphtylmethyl)N,N-diethylbenzamide (Compound 35)

The compound 35 was prepared by following the synthesis procedure as described for compound 1, but substituting 3-bromoanisole for 2-bromoanisole, and 1-naphtaldehyde for N,N-diethyl-4-carboxybenzamide.

$v_{max}$ (KBr)/cm$^{-1}$ 3302, 2976, 1607, 1430, 1290, 1098, 813; $\delta_H$ (400 MHz, CDCl$_3$) 1.09 (3H, br s), 1.22 (3H, br s), 2.60 (1H, d, J 3), 3.24 (2H, br s), 3.52 (2H, br s), 6.00 (1H, d, J 3), 7.30–7.50 (7H, m), 7.76–7.88 (4H, m);

II. Preparation of (±) 4-((α-Chloro)-2-naphtyl-methyl)-N,N-diethylbenzamide (Compound 36)

The compound 36 was prepared by following the synthesis procedure as described for compound 2, but substituting compound 1 for compound 35.

Used for the next step without further purification.

Example 23

Preparation of (±) 4-((α-(1-Piperazinyl))-2-naphtylmethyl)-N,N-diethylbenzamide (Compound 37)

The compound of this Example was prepared by following the synthesis procedure as described for Example 1, but substituting compound 2 for compound 36.

m.p. 106–108° C. (from acetonitrile), $v_{max}$ (KBr)/cm$^{-1}$ 3324, 3052, 2964, 2810, 2774, 1613, 1465, 1287, 1130, 1098; $\delta_H$ (400 MHz, CDCl$_3$) 1.07 (3H, br s), 1.19 (3H, br s), 1.89 (1H, br s), 2.40 (4H, br s), 2.89–2.92 (4H, m), 3.21 (2H, br s), 3.50 (2H, br s), 4.41 (1H, s), 7.24–7.84 (11H, 3m); C$_{26}$H$_{31}$N$_3$O.0.9 H$_2$O requires: C, 74.75; H, 7.91; N, 10.06 Found: C, 74.68; H, 7.56; N, 10.38.

Example 24

Preparation of (±) 4-((α-((4-Allyl)-1-piperazinyl))-2-naphtylmethyl)-N,N-diethylbenzamide (Compound 38)

The compound of this Example was prepared by following the synthesis procedure as described for Examples 2 and 3, but substituting compound 3 for compound 37.

$v_{max}$ (KBr)/cm$^{-1}$ 3053, 2968, 2805, 1629, 1426, 1288, 1141, 1095, 921, 817; $\delta_H$ (400 MHz, CDCl$_3$) 1.06 (3H, br s), 1.19 (3H, br s), 2.49 (6H, br s), 3.00 (2H, m), 3.20 (2H, br s), 3.49 (2H, br s), 4.41 (1H, s), 5.08–5.22 (2H, m), 5.78–5.92 (1H, m), 7.26–7.84 (11H, m); C$_{25}$H$_{34}$N$_3$OCl$_3$.0.6 H$_2$O requires: C, 76.99; H, 8.07; N, 9.29 Found: C, 77.06; H, 8.09; N, 9.32%.

Scheme 8

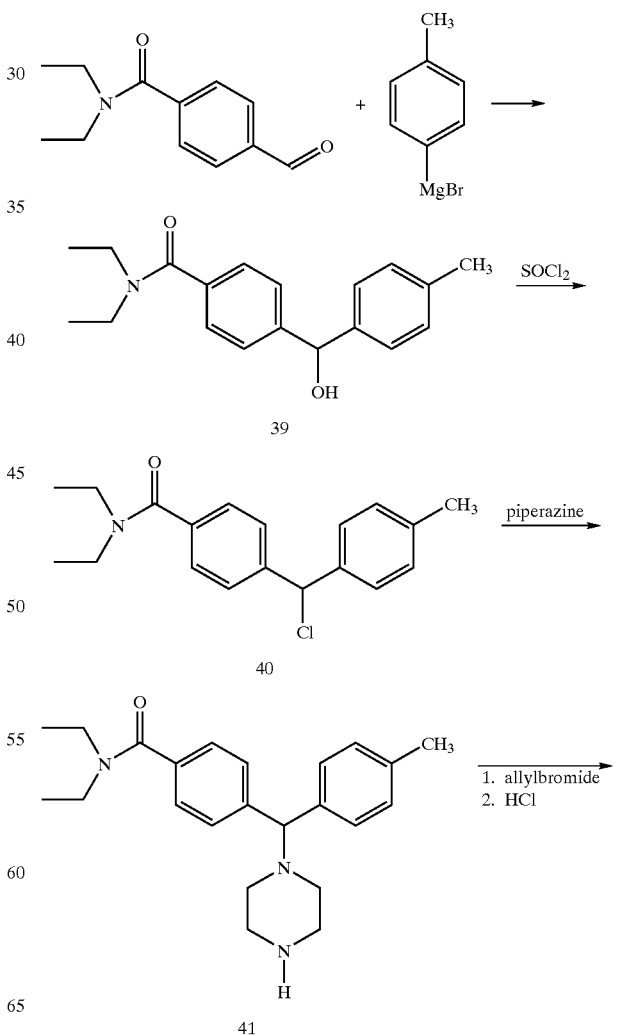

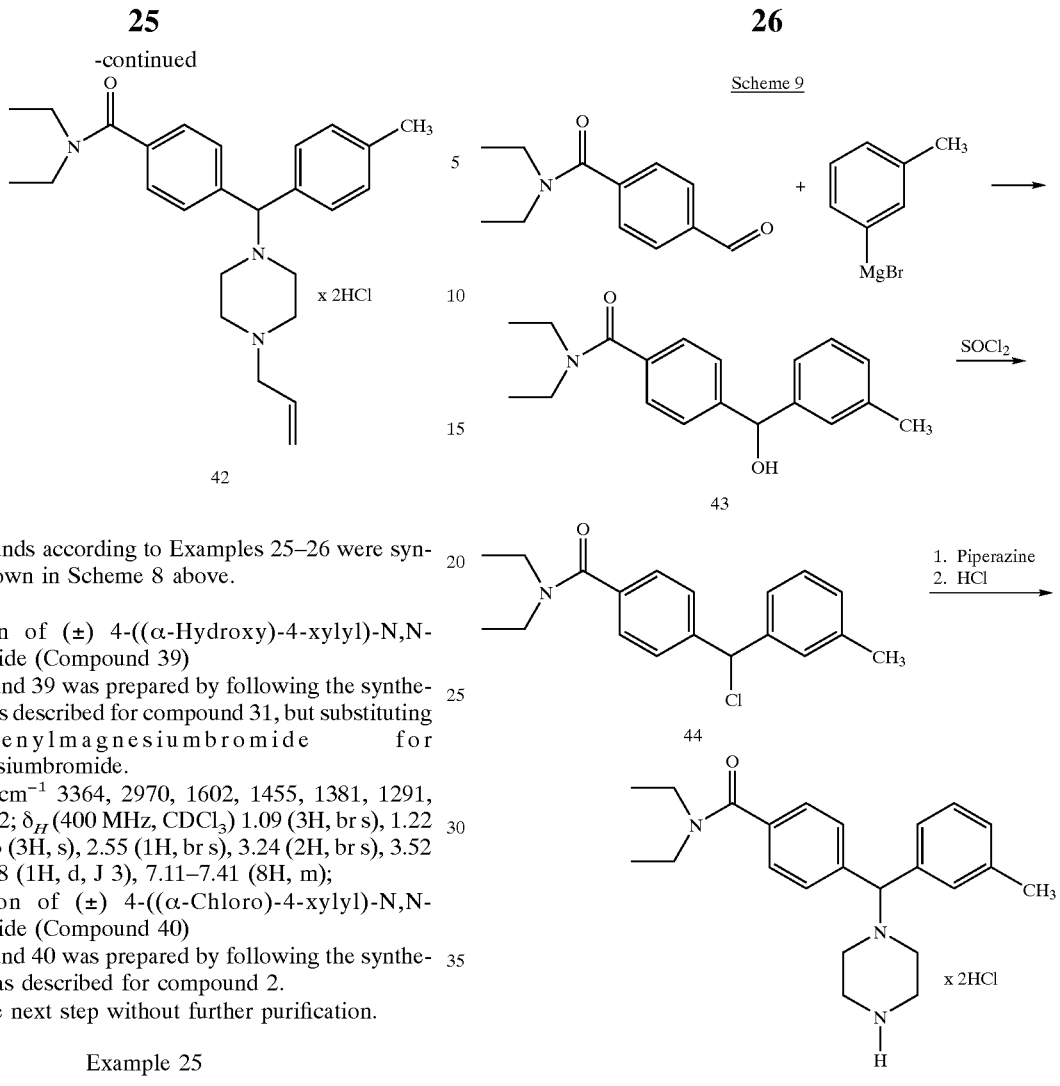

The compounds according to Examples 25–26 were synthesized as shown in Scheme 8 above.

H.

I. Preparation of (±) 4-((α-Hydroxy)-4-xylyl)-N,N-diethylbenzamide (Compound 39)

The compound 39 was prepared by following the synthesis procedure as described for compound 31, but substituting 4-chlorophenylmagnesiumbromide for 4-toluylmagnesiumbromide.

$v_{max}$ (KBr)/cm$^{-1}$ 3364, 2970, 1602, 1455, 1381, 1291, 1101, 1054, 802; $\delta_H$ (400 MHz, CDCl$_3$) 1.09 (3H, br s), 1.22 (3H, br s), 2.33 (3H, s), 2.55 (1H, br s), 3.24 (2H, br s), 3.52 (2H, br s), 5.78 (1H, d, J 3), 7.11–7.41 (8H, m);

II. Preparation of (±) 4-((α-Chloro)-4-xylyl)-N,N-diethylbenzamide (Compound 40)

The compound 40 was prepared by following the synthesis procedure as described for compound 2.

Used for the next step without further purification.

Example 25

Preparation of (±) 4-((α-(1-Piperazinyl))-4-xylyl)-N,N-diethylbenzamide (Compound 41)

The compound of this Example was prepared by following the synthesis procedure as described for compound 3.

m.p. 129–132° C. (from acetonitrile), $v_{max}$ (KBr)/cm$^{-1}$ 3320, 2957, 2811, 1610, 1437, 1285, 1128, 1010, 838; $\delta_H$ (400 MHz, CDCl$_3$) 1.10 (3H, br s), 1.20 (3H, br s), 1.83 (1H, br s), 2.30 (3H, s), 2.34 (4H, br s), 2.86–2.89 (4H, m), 3.24 (2H, br s), 3.51 (2H, br s), 4.20 (1H, s), 7.06–7.46 (8H, 3m); C$_{23}$H$_{31}$N$_3$O requires: C, 75.58; H, 8.55; N, 11.50 Found: C, 75.30; H, 8.54; N, 11.56.

Example 26

Preparation of (±) 4-((α-((4-Allyl)-1-piperazinyl)-4-xylyl)-N,N-diethylbenzamide.2HCl (Compound 42)

The compound of this Example was prepared by following the synthesis procedure as described for Examples 2 and 3.

m.p.>160° C. dec. (from ether); $v_{max}$ (KBr)/cm$^{-1}$ 3437, 2973, 2402, 1625, 1433, 1289, 1097, 944, 809; $\delta_H$ (400 MHz, CDCl$_3$, free base) 1.10 (3H, br s), 1.20 (3H, br s), 2.29 (3H, s), 2.35–2.60 (6H, m), 3.03 (2H, m), 3.24 (2H, br s), 3.52 (2H, br s), 4.22 (1H, s), 5.12–5.23 (2H, m), 5.81–5.93 (1H, m), 7.05–7.45 (8H, 3m);

The compounds according to Examples 27 were synthesized as shown in Scheme 9 above.

I.

I. Preparation of (±) 4-((α-Hydroxy)-3-xylyl)-N,N-diethylbenzamide (Compound 43)

The compound 43 was prepared by following the synthesis procedure as described for compound 31, but substituting 4-chlorophenylmagnesiumbromide for m-toluylmagnesiumbromide.

$v_{max}$ (KBr)/cm$^{-1}$ 3406, 2972, 1613, 1429, 1360, 1287, 1097, 1053, 789; $\delta_H$ (400 MHz, CDCl$_3$) 1.10 (3H, br s), 1.22 (3H, br s), 2.34 (3H, s), 2.55 (1H, d, J 3.5), 3.25 (2H, br s), 3.52 (2H, br s), 5.80 (1H, d, J 3), 7.12–7.42 (8H, m);

II. Preparation of (±) 4-((α-Chloro)-3-xylyl)-N,N-diethylbenzamide (Compound 44)

The compound 44 was prepared by following the synthesis procedure as described for compound 2.

Used for the next step without further purification.

Example 27

Preparation of (±) 4-((α-(1-Piperazinyl))-4-xylyl)-N,N-diethylbenzamide.2HCl (Compound 45)

The compound of this Example was prepared by following the synthesis procedure as described for compound 3.

m.p.>130° C. dec. (from ether), $v_{max}$ (Kbr)/cm$^{-1}$ 2971, 2805, 2715, 1624, 1434, 1289, 1096, 783; $δ_H$ (400 MHz, CDCl$_3$, free base) 1.10 (3H, br s), 1.20 (3H, br s), 2.31 (3H, s), 2.35–2.45 (5H, m), 2.89–2.92 (4H, m), 3.25 (2H, br s), 3.51 (2H, br s), 4.19 (1H, s,), 6.98–7.46 (8H, 4m);

m.p. 113–116° C. (from acetonitrile), $v_{max}$ (KBr)/cm$^{-1}$ 3330, 2936, 2845, 1623, 1431, 1286, 1096, 823; $δ_H$ (400 MHz, CDCl$_3$) 0.64–2.02 (18H, m), 2.18–2.40 (4H, m), 2.75–2.87 (4H, m), 3.06 (1H, d, J 8.8), 3.27 (2H, br s), 3.52 (2H, br s), 7.11 (2H, d, J 8.4), 7.29 (2H, d,J, 8.4);

Scheme 10

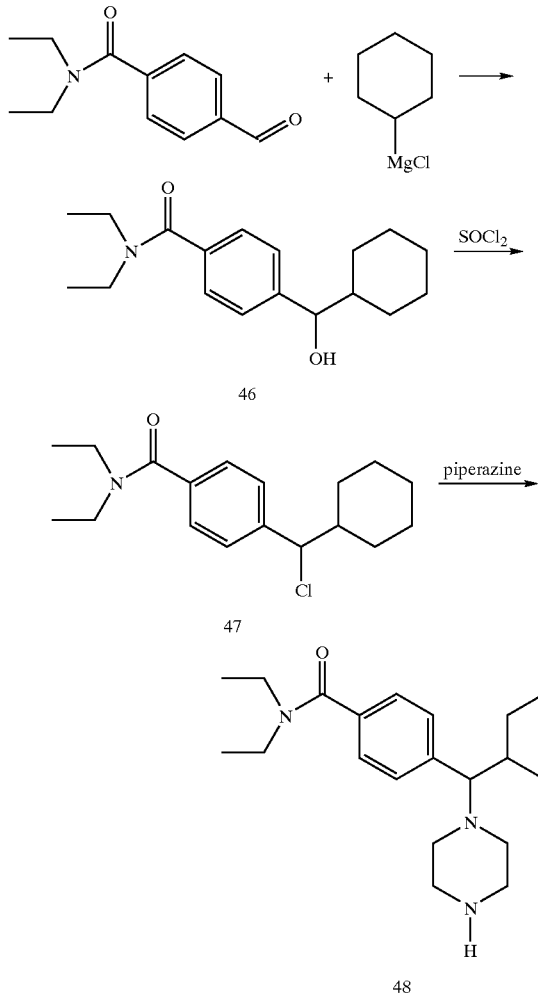

Scheme 11

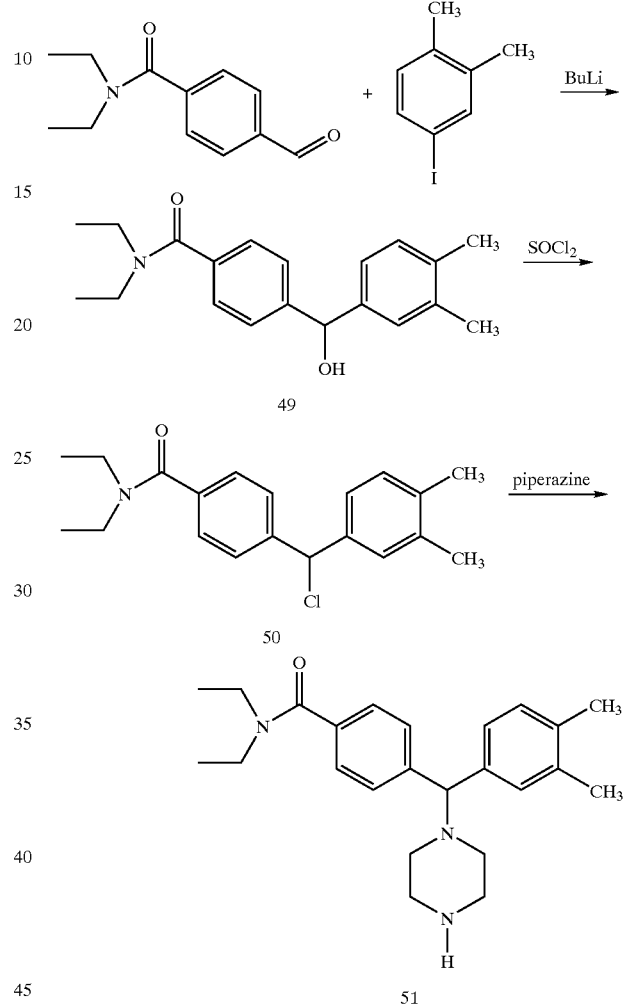

The compounds according to Example 28 were synthesized as shown in Scheme 10 above.

J.
I. Preparation of (±) 4-((α-Hydroxy)-cyclohexylmethyl)-N,N-diethylbenzamide (Compound 46)

The compound 46 was prepared by following the synthesis procedure as described for compound 31.

$δ_H$ (400 MHz, CDCl$_3$) 0.85–2.0 (18H, m), 3.26 (2H, br s), 3.53 (2H, br s), 4.35–4.43 (1H, m), 7.28–7.36 (4H, m);

II. Preparation of (±) 4-((α-Chloro)-cyclohexylmethyl)-N,N-diethylbenzamide (Compound 47)

The compound 47 was prepared by following the synthesis procedure as described for compound 2.

Used for the next step without further purification.

Example 28

Preparation of (±) 4-((α-(1-Piperazinyl))-cyclohexylmethyl)-N,N-diethylbenzamide (Compound 48)

The compound of this Example was prepared by following the synthesis procedure as described for compound 3.

The compounds according to Examples 29 were synthesized as shown in Scheme 11 above.

K.
I. Preparation of (±) 4-((α-Hydroxy)-3,4-dimethylbenzyl)-N,N-diethylbenzamide (Compound 49)

The compound 49 was prepared by following the synthesis procedure as described for compound 1.

$δ_H$ (400 MHz, CDCl$_3$) 1.09 (3H, br s), 2.23 (6H, s), 2.85 (1H, d, J 3), 3.24 (2H, br s), 3.51 (2H, br s), 5.73 (1H, d, J 2), 7.03–7.12 (m, 3H), 7.26–7.39 (m, 4H);

II. Preoaration of (±) 4-((α-Chloro)-3,4-dimethylbenzyl)-N,N-diethylbenzamide (Compound 50)

The compound 50 was prepared by following the synthesis procedure as described for compound 2.

Used for the next step without further purification.

Example 29

Preparation of (±) 4-((α-(1-Piperazinyl))-3,4-dimethylbenzyl)-N,N-diethylbenzamide (Comoound 51)

The compound of this Example was prepared by following the synthesis procedure as described for compound 3.

$v_{max}$ (KBr)/cm$^{-1}$ 3304, 2939, 2810, 1626, 1429, 1286, 1096, 846; $\delta_H$ (400 MHz, CDCl$_3$) 1.11 (3H, br s), 1.20 (3H, br s), 1.87 (1H, br s), 2.20 (3H, s), 2.22 (3H, s), 2.34 (4H, br s), 2.86–2.89 (4H, m), 3.25 (2H, br s), 3.51 (2H, br s), 4.15 (1H, s), 7.02–7.15 (3H, m), 7.26–7.30 (2H, m), 7.42–7.46 (2H, m);

Scheme 12

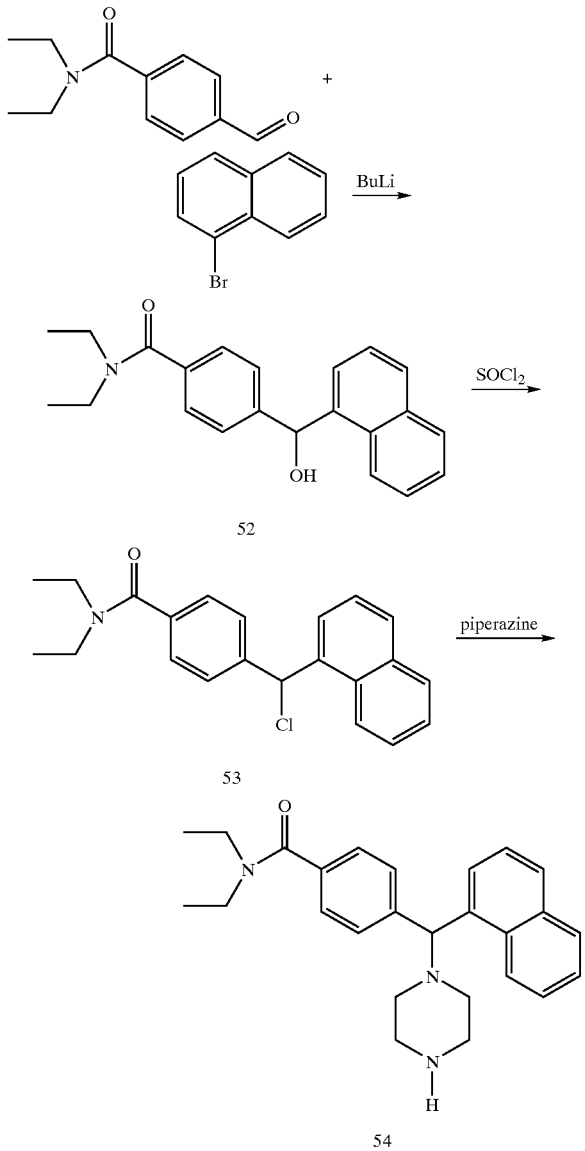

The compounds according to Examples 30 were synthesized as shown in Scheme 12 above.

L.

I. Preparation of (±) 4-((α-Hydroxy)-1-naphtylmethyl)-N,N-diethylbenzaniide (Compound 52)

The compound 52 was prepared by following the synthesis procedure as described for compound 1.

$\delta_H$ (400 MHz, CDCl$_3$) 1.06 (3H, br s), 1.20 (3H, br s), 3.01 (1H, d, J 4), 3.21 (2H, br s), 3.49 (2H, br s), 6.47 (1H, d, J 4), 7.24–7.48 (7H, m), 7.55–7.58 (1H, m), 7.78–7.87 (2H, m), 7.98–8.01 (1H, m);

II. Preparation of (±) 4-((α-Chloro)-1-naphtylmethyl)-N,N-diethylbenzamide (Compound 53)

The compound 53 was prepared by following the synthesis procedure as described for compound 2.

Used for the next step without further purification.

Example 30

Preparation of (±) 4-((α-(1-Piperazinyl))-1-naphtylmethyl)-N,N-diethylbenzamide (Compound 54)

The compound of this Example was prepared by following the synthesis procedure as described for compound 3.

$v_{max}$ (KBr)/cm$^{-1}$ 3307, 3050, 2966, 2814, 1625, 1431, 1287, 1098, 843, 797; $\delta_H$ (400 MHz, CDCl$_3$) 1.04 (3H, br s), 1.17 (3H, br s), 2.14 (1H, br s), 2.40 (2H, br s), 2.46 (2H, br s), 2.83–2.95 (4H, m), 3.17 (2H, br s), 3.48 (2H, br s), 5.05 (1H, s), 7.22–7.28 (2H, m), 7.40–7.54 (5H, m), 7.70–7.94 (3H, m), 8.40–8.43 (1H, m);

Piperazine Ring Modifications: General Experimental and Examples

The compounds according to Examples 31–42 were synthesized as shown in Scheme 13 below.

M.

I. Preparation of 2-Dimethyl-5-metbyl-piperazine-3,5-dione (Compound 55)

N-t-Butoxycarbonyl-2-aminoisobutyric acid (5.0 g, 25 mmol) and D,L-alanine methylester hydrochloride (3.5 g, 25 mmol) was dissolved in dry dichloromethane (50 mL) and cooled to 0° C. Triethylaniine (3.5 mL, 25 mmol) and then 1-(3-dimethylaminopropyl)-3-ethyl-carbodiimide hydrochloride (4.8 g, 25 mmol) was added and the mixture was stirred at 0° C. until lumps dissolved. The reaction mixture was then left in the freezer 4 d at –20° C. The organic solution was washed with water, 1M citric acid (aq.), water, dried (Na$_2$SO$_4$) and evaporated in vacuo to give 6.0 g (83%) of coupling product. Most of the coupling product (5 g) was dissolved in fonnic acid (50 mL) and stirred 12 h at 25° C. The acid was removed in vacuo and the residue dissolved in 2-butanol and heated at reflux for 4 h. The solution was cooled to 0° C. and the crystals filtered off and dried in vacuo at 100° C. Yield 2.6 g of pure compound 55 (82%) which could be recrystallized from methanol, mp: >300° C. IR (Kbr) (cm–1): 3000 (br), 1680 (s) (C=O). $^1$H NMR (D$_2$O): δ=4.75 (s, 2H, NH), 4.21 (q, 1H, CHMe), 1.50–1.42 (m, 9H, 3Me). C$_7$H$_{12}$N$_2$O$_2$ requires C, 53.83; H, 7.74; N, 17.94. Found C, 53.89; H, 7.90; N, 17.79.

II. Preparation of 2-Dimetbyl-5-methyl-piperazine dihydrochloride (Compound 56)

Compound 55 (2.2 g, 14 mmol) was dissolved on dry THF (120 mL). Lithium aluminum hydride (42 mL, 1M in THF) was added in small portions. When addition complete, the solution was heated at reflux over night. The solution was allowed to cool, then excess hydride was destroyed by dropwise addition of water (1.6 mL), NaOH (1.6 mL, 15% solution) and water (4.8 mL). The granular precipitate was filtered off and solvent evaporated in vacua. The residue was dissolved in dichloromethane, dried (K$_2$CO$_3$) and evaporation of solvent in vacuo gave 1.5 g (84%). Treatment with excess HCl in ether gave the dihydrochloride compound 56 which could be recrystallized from methanol/ether mp: >300° C. IR (cm–1), KBr: 2760, 1570 (R$_2$NH$_2$+). MS (amine): 128, 113, 84, 71, 58. $^1$H NMR (D$_2$O+DSS): δ=2.70–2.50 (m, 5H, CH$_2$—N, CH—N), 1.14 (s, 3H, 1 Me), 1.00–0.94 (s+d, 6H, 2 Me). C$_7$H$_{16}$N$_2$×2HCl requires C, 41.80; H, 9.02; N, 13.93. Found C, 42.03; H,9.24; N, 14.00.

Example 31

Preparation of 4-(4-(2-Dimethyl-5-methyl-piperazinyl)-3-methoxybenzyl)-N,N-diethylbenzamide dihdrochloride (Compound 57)

4-(Chloro-(3-methoxyphenyl)methyl)-N,N-diethylbenzamide (0.61 g, 2.0 mmol) and compound 56

(0.50 g, 3.9 mmol) was dissolved in dry acetonitrile (5 mL). Potassium carbonate (0.26 g, 2.0 mmol) was added and the mixture heated at reflux for 2 d. The solvent was removed in vacuo and the residue purified by flash chromatography on silica ($CH_2Cl_2$/MeOH/$NH_3$(aq.)), 98:1:1 to 95:5:1 to yield 0.65 g (79%). Treatment with excess of HCl in ether, filtering and drying crystals in vacuo over KOH gave the dihydrochloride compound 57, mp: 134–36° C. IR (HCl salt, KBr) (cm-1): 3400 (br, OH), 2900 (br, $R_2NH_2$+), 1600 (s, C=O or $R_2NH_2$+), 1283, 1038 (C—O). MS (amine) 3 peaks: 423, 353, 325, 296, 127. $^1$H NMR: (amine, $CDCl_3$): δ=7.40–6.60 (m, 8H, Ar—H), 5.26, 5.25, 4.61 (3s, 1H, CHAr$_2$), 3.70 (s, 3H, MeO), 3.4, 3.2 (2 br. s, 4H, MeCH$_2$), 3.1–2.0 (m, 5H, piperazine-H), 1.3–0.9 (m, 15H, 5Me). $C_{26}H_{37}N_3O_2\times 2HCl$ requires C, 62.89; H, 7.92; N, 8.46. Found C, 63.41; H, 8.38; N, 8.56.

Example 32

Preparation of 4(4-(1-Allyl-2-dimethyl-5-methyl-piperazinyl-3-methoxybenzyl)-N,N-diethylbenzamide dihydrochloride (Compound 58)

Compound 57 (0.39 g, 0.92 mmol) was dissolved in dry acetonitrile (5 mL). Potassium carbonate (0.13 g, 0.92 mmol) and allyl bromide (90 μL 1.02 mmol) was added. After 3 h at 25° C. the solvent was evaporated and the residue purified by flash chromatography on silica $CH_2Cl_2$/MeOH), 98:2 to 95:5 to give a total of 0.39 g (92%). Treatment with excess of HCl in ether, filtering and drying crystals in vacuo over KOH gave the dihydrochloride, compound 58, mp: 105–21° C. IR (HCl salt, Kbr) (cm-1): 3400 (br, OH), 2500 (br, $R_2NH_2$+), 16200 (s) (C=O or $R_2NH_2$+), 1285, 1043 (C—O). $^1$H NMR: (amine, $CDCl_3$): δ=7.50–6.60 (m, 8H, Ar—H), 5.70 (m, 1H, allyl-H), 5.00 (m, 2H, allyl-H), 4.70 (s, 1H, CHAr$_2$), 3.70 (s, 3H, MeO), 3.5+3.3 (2 br. s, 4H, MeCH$_2$), 3.0–1.9 (m, 7H, piperazine-H), 1.2–0.8 (m, 15H, 5Me). $C_{29}H_{41}N_3O_2\times 2HCl$ requires C, 64.91; H, 8.08; N, 7.83. Found C, 65.70; H, 8.60; N, 8.29. N.

I. Preparation of 4-Allyl-2-dimethyl-5-methyl-piperazine (Compound 59)

Compound 56 (0.14 g, 0.91 mmol) was dissolved in acetonitrile and allyl bromide (80 μL, 0.91 mmol) was added at 0° C. After 1 h another portion of allyl bromide was added. After 2 h the solvent was evaporated and the residue purified by flash chromatography on silica ($CH_2Cl_2$/MeOH), 95:5 to 80:20 to give the monoallyl compound 59, 116 mg (69%).

Examnple 33

Preparation of 4-(1-(4-Allyl-2-dimethyl-5-methyl-piperazinyl)-3-methoxybenzyl)-N,N-dietbylbenzamide dihydrochloride (Compound 60)

The compound of this Example was prepared by following the synthesis procedure as described for Example 3.

Mp: 125–30° C. IR (2HCl, KBr) (cm-1): 3430(br), 2978, 2480(br.), 1607, 1436, 1285. MS(free amidne): 366, 296, 167. $^1$H NMR: ($D_2O$+DSS): δ=7.60–6.90 (m, 9H, Ar—H), 6.0–5.5 (m, 4H, allyl-H+Ar$_2$CH), 3.80 (2s, 3H, MeO), 4.0–3.7 (m, 11H, allyl-H, piperazine-H, amide-CH$_2$), 1.3–1.0 (m, 15H, piperazine-Me, amide-Me). Anal. calc. for $C_{29}H_{41}N_3O_2\times 2HCl\times 2.9$ $H_2O$: C,59.15; H, 8.35; N, 7.14. Found: C, 59.05; H,8.00; N, 7.22.

Example 34

Preparation of 4-(1-(2-dimethyl-5-methyl-piperazinyl)-3 methoxybenzyl)-N,N-diethylbenzamide dihydrochloride (Compound 61)

56 (42 mg, 0.33 mmol) and potassium carbonate (46 mg, 0.33 mmol) was dissolved in water (2 mL) and di-t-butyl dicarbonate (79 mg, 0.36 mmol) was added. After stirring 1 h the solvent was evaporated in vacuo and the residue purified by chromatography on silica ($CH_2Cl_2$/MeOH), 90:10 to give 43 mg of the mono-N-Boc protected 55 which was dissolved in dry acetonitrile together with potassium carbonate (26 mg, 0.19 mmol) and 4-(Chloro-(3-methoxyphenyl)methyl)-N,N-diethylbenzamide (63 mg, 0.19 mmol). After heating 4 days at reflux, the solvent was removed in vacuo and residue purified by chromatography on silica ($CH_2Cl_2$/MeOH), 100:0, 95:5. Treatment with formic acid (5 mL) for 3 h, evaporation of solvent in vacuo and extraction of the residue with $CH_2Cl_2$/1M NaOH, drying of the organic phase ($K_2CO_3$) and evaporation of solvent in vacuo gave 27 mg (33%) of the free amine. Treatment with excess HCl in ether gave the dihydrochloride which was dissolved in water and freezedried, mp: 145–50° C. IR (2HCl, KBr) (cm-1): 3500–3400(br), 1601, 1442, 1285. MS(free amine): 423, 296, 325, 127. $^1$H NMR: ($CDCl_3$): δ=7.4–6.6 (m, 8H, Ar—H), 5.39, 5.36 (2s, 1H, Ar$_2$CH), 3.75 (s, 3H, MeO), 3.5, 3.25 (2 br. s, 4H, amide-Me), 2.80, 2.50, 2.05 (3m, 5H, piperazine-H), 1.5 (br.s, 1H, N—H), 1.25–1.0 (br. m, 6H, amide-Me), 1.15 (s, 3H, Me), 0.90 (d, 3H, Me), 0.85 (s, 3H, Me). Calc. for $C_{26}H_{37}N_3O_2\times 2HCl\times 7.4$ $H_2O$: C, 49.58; H, 8.61; N, 6.67. Found: C, 49.61; H, 7.73; N, 6.56. O.

I. Preparation of 4-(Phenyl-hydroxymethyl)-N,N-diethylbenzamide (Compound 62)

The compound 62 was prepared by following the synthesis procedure as described for compound 1.

MS: 282, 211, 165, 105. $^1$H NMR: ($CDCl_3$): δ=7.38–7.20 (m, 9H), 5.80 (d, J=3.5 Hz, 1H), 3.5, 3.2 (2br.s, 4H), 1.2, 1.05 (2br. s, 6H).

II. Preparation of 4-(Chloro-phenyl-methyl)-N,N-diethylbenzamide (Compound 63)

The compound 63 was prepared by following the synthesis procedure as described for compound 2.

GC-MS (2 peaks): 296, 225, 165, 121, and 300, 266, 229, 195, 165. H NMR: ($CDCl_3$): δ=7.45–7.20 (m, 9H), 6.09 (s, 1H), 3.4 (br. m, 4H), 1.1 (br. m, 6H).

Example 35

Preparation of 4((1-piperazinyl)-benzyl)-N,N-diethylbenzamide dihydrochloride (Compound 64)

The compound of this Example was prepared by following the synthesis procedure as described for compound 3.

Mp: 157–69° C. IR (amine, $CDCl_3$ in KBr cell) (cm-1): 3690, 3630, 1613, 1435, 1265. MS (free amine): 351, 306, 295, 266, 194, 165. $^1$H NMR: (free amine, $CDCl_3$): δ=7.46–7.16 (m, 9H, Ar—H), 4.24 (s, 1H, CHAr$_2$), 3.5+3.2 (2 br. s, 4H, MeCH$_2$), 2.89 (m, 4H, piperazine-H), 2.36 (br. s, 4H, piperazine-H), 1.94 (br s, 1H, NH), 1.2+1.1 (2 br. s, 6H, 2Me). Anal. calc. for $C_{22}H_{29}N_3O\times 2HCl\times 1.90$ $H_2O$, C, 57.61; H, 7.65; N: 9.16. Found C, 57.59; H, 7.66; N, 8.92.

Example 36

Preparation of 4-((4-Allyl-1-piperazinyl)-benzyl)-N,N-diethylbenzamide dihydrochloride (Compound 65)

The compound of this Example was prepared by following the synthesis procedure as described for Examples 2 and 3.

Mp: 175–205° C. IR (amine, $CDCl_3$ in KBr cell) (cm-1): 3689, 1613, 1455, 1434, 1290, 1143. MS (free amnine): 391, 165, 125. $^1$H NMR: (free amine, $CDCl_3$): δ=7.42–7.12 (m, 9H, Ar—H), 5.81 (m, 1H, allyl-H), 5.10 (m, 2H, allyl-H), 4.23 (s, 1H, CHAr$_2$), 3.5+3.2 (2 br. s, 4H, MeCH$_2$), 3.00 (m, 2H, allyl-H), 2.6–2.4 (br. s, 8H, piperazine-H), 1.1 (2 br. s, 6H, 2Me). Anal. calc. for C$_{25}$H$_{35}$N$_3$O×2HCl×1.0 H$_2$O, C, 62.23; H, 7.73; N, 8.71. C, 62.22; H, 7.49; N, 8.42.

P.
I. Preparation of 2-Hydroxymethyl-5-methyl-1-piperazine-3,5-dione (Compoumd 66)

(D,L)-N-t-Butoxycarbonyl-alanine (5.0 g, 26 mmol) was dissolved in methylene chloride (50 mL) with triethyl amine (8.1 mL), dried with 4A molecular sieves and transfered to dry flask under nitrogen. i-Butyl chlorofornate (3.8 mL, 29 mmol) was added at −10° C. The Solution was stirred 15 min, then D,L-serine methylester hydrochloride (4.1 g, 26 mmol) was added and the solution was allowed to reach 25° C. and strired 12 h. Washing the solution with brine, drying (MgSO$_4$) and evaporating solvent in vacuo gave a solid which was treated with formic acid for 1 h. The acid was removed in vacuo and the residue dissolved in anhydrous 2-butanol (5 mL) and heated at reflux 2 days. The solvent was removed and the residue crystallized when treated with acetone to give 1 g of compound 66 (24%).

II. Preparation of 2-Hydroxymetbyl-5-methyl-piperazine (Compound 67)

The compound 67 was prepared by following the synthesis procedure as described for compound 55.

II. Preparation of 2-(t-Butyldiphenylsilyloxy)methyl-5-methyl-piperazine (Compound 68)

Compound 67 (0.41 g, 3.1 mmol) was dissolved in dry DMF (5 mL). Chloro-t-butyldiphenylsilane (0.95 g, 3.4 mmol) and immidazole (0.47 g, 6.9 mmol) was added and stirring was continued 12 h. The product was extracted by adding ethyl acetate, brine and 1M NaOH and shaking. The organic phase was dried and evaporated in vacuo. Chromatography of the residue on silica (CH$_2$Cl$_2$/MeOH, 100:0, 95:5, 90:10 and 80:20) gave 0.39 g (34%) pure compound 68.

Example 37

Preparation of 4-(4-(2-Hydroxymethyl-5-methyl) piperazinyl-benzyl)-N,N-diethrl-benzamide dihydrochloride (Compound 69)

The compound of this Example was prepared by following the synthesis procedure as described for compound 3.

Mp: 145–50° C. IR (2HCl, KBr) (cm−1): 3300(br), 2700 (br), 1612, 1446, 1382, 1296, 1080. MS(free amine): 381, 218, 181, 91. $^1$H NMR: (free amine, CDCl$_3$): δ=7.44–7.18 (m, 9H, Ar—H), 5.17, 5.14 (2s, 1H,ArCH$_2$), 3.75–2.60 (m, 12H, piperazine-H, amide-CH$_2$), 2.02 (m, 1H, piperazine-H), 1.30–1.05 (m, 9H, piperazine-Me+amide-Me). Anal. calc. for C$_{24}$H$_{33}$N$_3$O$_2$×2HCl×1.8 H$_2$O: C, 57.55; H, 7.77; N, 8.39. Found: C, 57.05; H, 7.67; N, 8.19.

Example 38

Preparation of 4-((4-(2-Hydroxymethyl-5-methyl) piperazinyl)-3-methoxybenzl)-N,N-diethylbenzamide dihydrochloride (Compound 70)

The compound of this Example was prepared by following the synthesis procedure as described for compound 3.

Mp: 185–90° C. IR (2HCl, KBr) (cm−1): 3500–2500(br), 1596, 1440, 1045. $^1$H NMR: (free amine, CDCl$_3$): δ=7.40–6.60 (m, 8H, Ar—H), 5.05, 5.10 (2s, 1H, Ar$_2$CH), 3.70 (s, 3H, MeO), 3.8–2.5 (m, 12H, piperazine, amide CH$_2$) 1.2–1.0 (br. s, 9H, amide-Me, piperazine-Me).

Example 39

Preparation of 4-((4-(1-Allyl-2-hydroxymethyl-5-methyl)piperazinyl)-3-methoxybenzyl)-N,N-diethylbenzamide dihydrochloride (Compound 71)

The compound of this Example was prepared by following the synthesis procedure as described for Examples 2 and 3.

Mp: 125–30° C. IR (2HCl, KBr) (cm−1): 3400(br), 1603, 1445, 1285. MS(free amine): two peaks: 310, 239, 135 and 312, 241, 135. $^1$H NMR: (free amine, CDCl$_3$): δ=7.50–6.70 (m, 8H, Ar—H), 5.80, 5.20, 5.00 (3m, 3H, allyl-H), 4.0–2.3 (m, 14H, piperazine-H,allyl-H, amide-CH$_2$) 3.80 (s, 3H, MeO), 1.2 (br. s, 6H, amide-Me). Anal. calc. for C$_{25}$H$_{35}$N$_3$O$_3$×2HCl×3.7 H$_2$O: C,55.57; H, 8.06; N, 6.94. Found: C, 55.53; H, 7.82; N, 7.16.

O.
I. Preparation of Methyl 3-(hydroxy-(2-naphtyl)methyl) phenyl ether (Compound 72)

The compound 72 was prepared by following the synthesis procedure as described for compound 1.

MS: 264, 155, 135, 128, 109, 101. $^1$H NMR: (CDCl$_3$): δ=7.90–6.78 (m, 11H, Ar—H), 5.98 (d, J=3.5 Hz, 1H, Ar$_2$H), 3.78 (s, 3H, MeO), 2.32 (d, J=3.5 Hz, 1H, OH).

II. Preparation of Methyl 3-(chloro-(2-naphtyl)methyl) phenyl ether (Compound 73)

The compound 73 was prepared by following the synthesis procedure as described for compound 2.

GC-MS (2 peaks): 278, 247, 215, 171, 155, 135 and 282, 248, 247, 231, 215. $^1$H NMR: (CDCl$_3$): δ=7.86–6.81 (m, 11H, Ar—H), 6.25 (s, 1H, Ar$_2$H), 3.76 (s, 3H, MeO).

III. Preparation of 4-Allyl-2-methylpiperazine (Compound 74)

2-Methylpiperazine (0.4 g, 4 mmol) was dissolved in acetonitrile (5 mL) and allyl bromide (86 μL, 1 mmol) was added at 0° C. Stirring was continued at 0° C. for 1 h, then at 25° C. for 6 h. Evaporation of solvent in vacuo and chromatography on silica (CH$_2$Cl$_2$/MeOH, 80:20) gave 80 mg (57%) pure compound 74.

Example 40

Preparation of Methyl 3-((2-naphtyl)-(3-methyl-piperazinyl)methyl)phenyl ether dihydrochloride (Compound 75)

The compound of this Example was prepared by following the synthesis procedure as described for compound 3.

Mp: 170–74° C. IR (KBr) (cm−1): 3461, 2458, 1600, 1439, 1263, 1043. MS (amine): 386, 247, 215, 139, 112. $^1$H NMR: (amine, CDCl$_3$): δ=7.84–6.66 (m, 11H, Ar—H), 4.33 (s, 1H, CHAr$_2$), 3.74, 3.73 (2s, 3H, MeO), 3.00–2.70 (m, 6H, piperazine-H), 1.95, 1.65 (2m, 2H, piperazine-H), 0.98–0.92 (2d, J=6.4 Hz, 3H, piperazine-Me). Anal. calc. for C$_{23}$H$_{26}$N$_2$O×2HCl×1.8 H$_2$O, C, 61.14; H, 7.05; N, 6.20. Found, C, 61.05; H, 6.48; N, 6.07.

Example 41

Preparation of Methyl 3-((2-naphtyl)-(4-allyl-2-methyl-piperazinyl)methyl)phenyl ether dihydrochloride (Compound 76)

The compound of this Example was prepared by following the synthesis procedure as described for Example 3.

Mp: 173–82° C. IR (KBr) (cm−1): 3430, 2500, 2355, 1601, 1436, 1265, 1047. MS (amine): 386, 274, 247, 215, 139, 125. $^1$H NMR: (amine, CDCl$_3$): δ=7.86–6.66 (m, 11H, Ar—H), 5.82 (m, 1H, allyl-H), 5.12 (m, 2H, allyl-H), 4.95 (br. s, 1H, CHAr$_2$), 3.76, 3.75 (2s, 3H, MeO), 3.04–2.32 (m, 9H, piperazine-H), 1.15–1.11 (2d, 3H, Me). Anal. calc. for C$_{26}$H$_{32}$N$_2$O×2HCl×0.4 H$_2$O, C, 66.92; H, 7.08; N, 6.00. Found C, 67.03; H, 7.09; N, 5.88.

Example 42

Preparation of 4-((4-Acetyl-1-Piperazinyl)-benzyl)-N,N-diethylbenzamide hydrochloride (Compound 77)

The free amine of compound 64 (100 mg, 0.28 mmol) was dissolved in methylene chloride (5 ml), cooled to 0° C. Triethyl amine (43 μl, 0.31 mmol) was added and then acetyl chloride (22 μl, 0.31 mmol) was added dropwise. After 10 min, the solution was washed with potassium carbonate (10%), dried (K$_2$CO$_3$) and evaporated in vacuo. The residue was purified by chromatography on silica (CH$_2$Cl$_2$/MeOH/NH$_3$, 95:5:0.5) to give 116 mg of compound 77 (~100%).

Mp: 140–50° C. IR (KBr) (cm–1): 3480(br), 2987, 2500 (br), 1623, 1429, 1285, 1245. MS (free amine): 393, 267, 165, 127, $^1$H NMR: (free amine, CDCl$_3$): δ=7.46–7.18 (m, 9H, Ar—H), 4.25 (s, 1H, CHAr$_2$), 3.70–3.15 (m, 8H, amide-CH$_2$, piperazine-H), 2.36 (m, 4H, piperazine-H), 2.05 (s, 3H, MeCO), 1.15 (br. m, 6H, amide-Me). Anal. calc. for C$_{24}$H$_{31}$N$_3$O$_2$×1HCl×0.80 H$_2$O, C, 64.87; H, 7.62; N, 9.46. Found C, 65.01; H, 7.776; N, 9.42.

Scheme 13

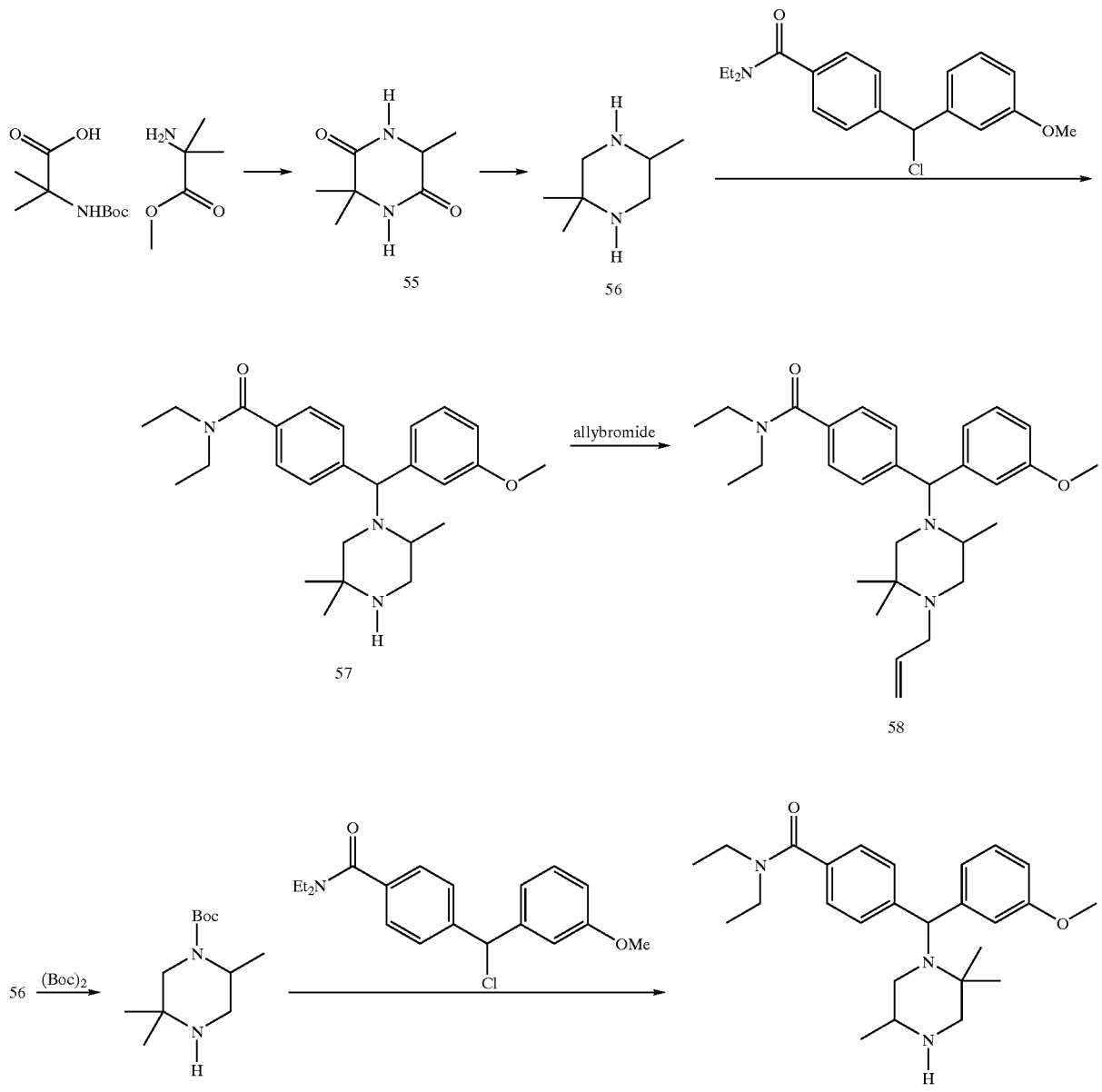

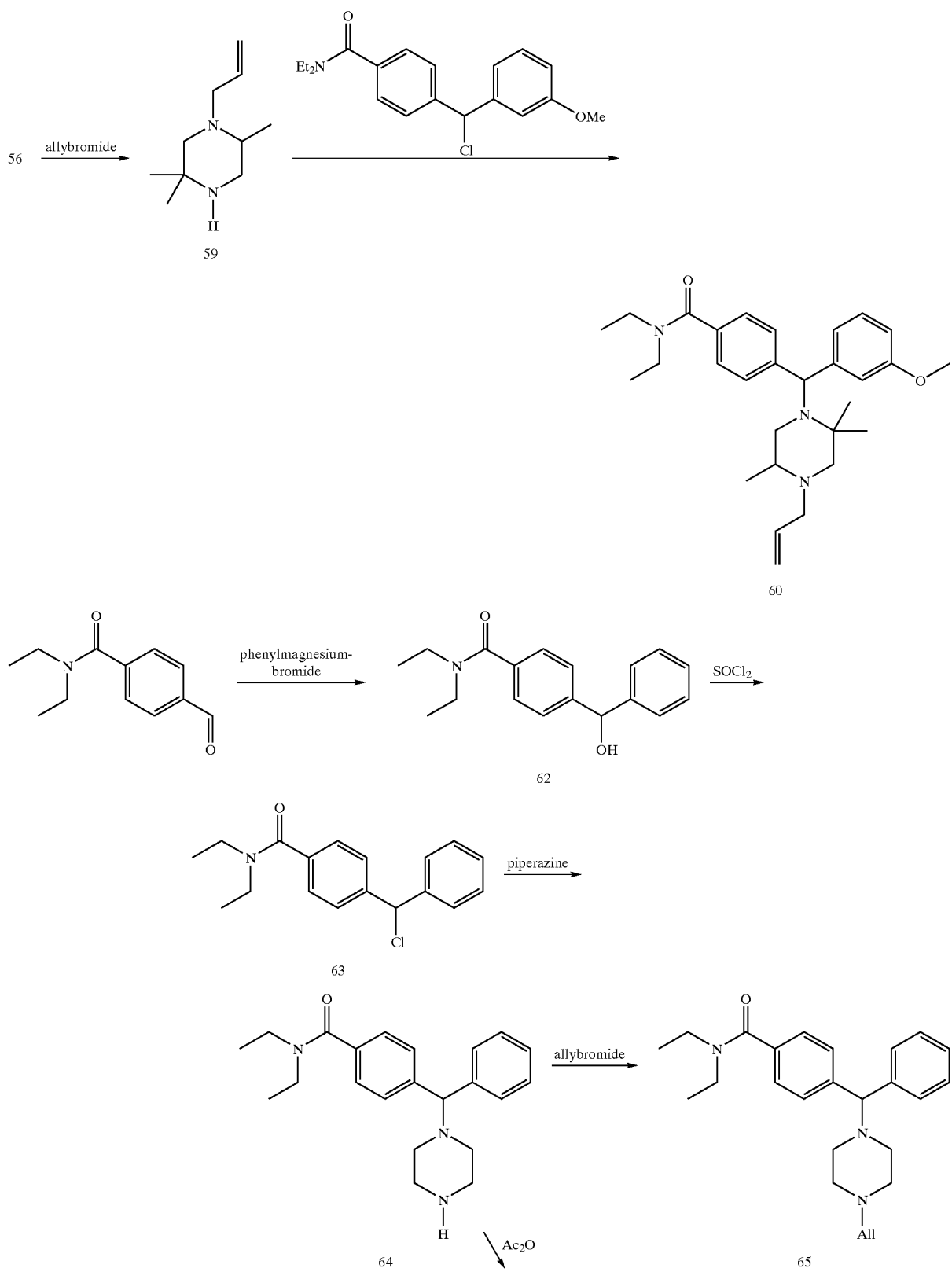

-continued
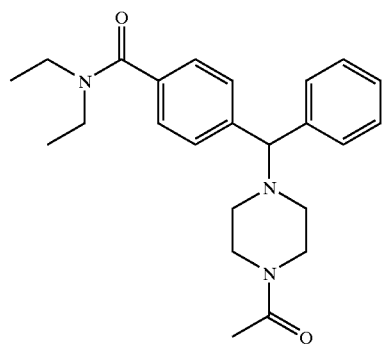
77
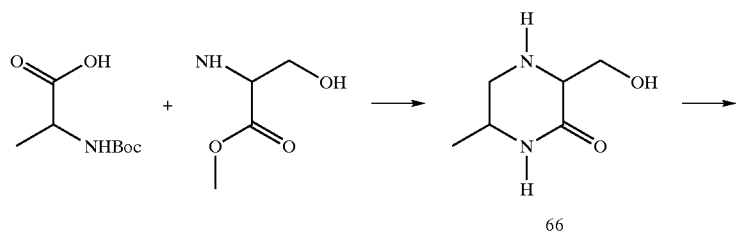
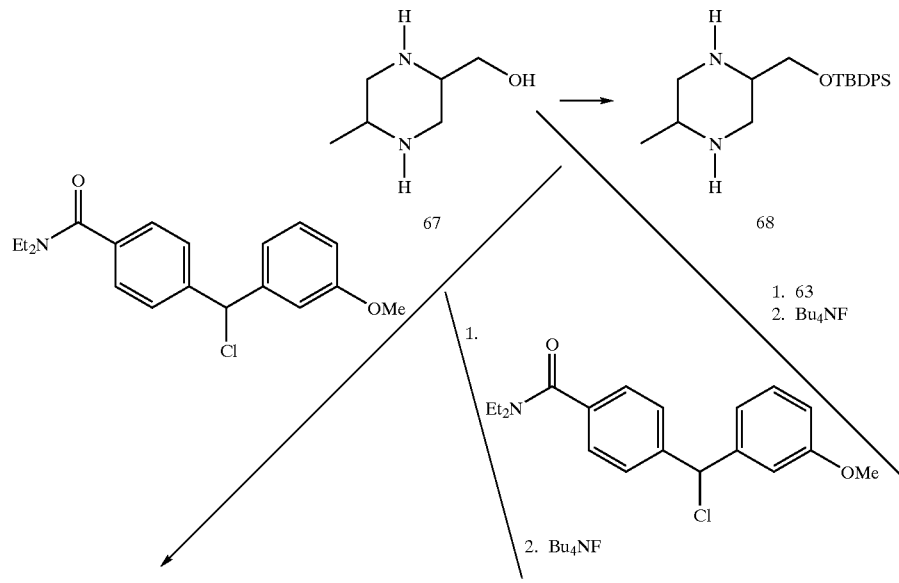

41
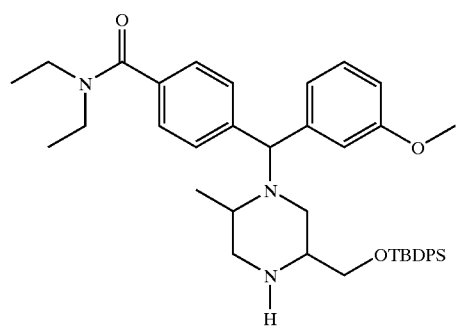
1. allybromide
2.
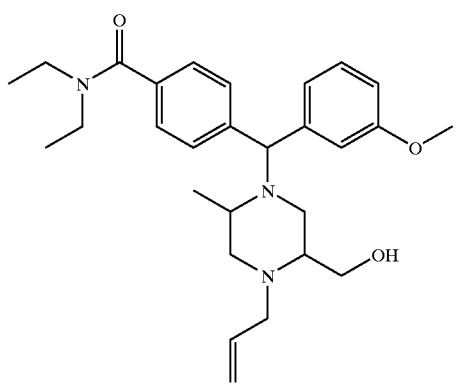
71
42
-continued
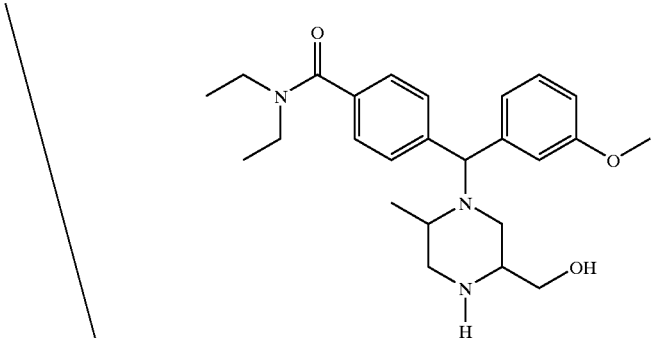
69
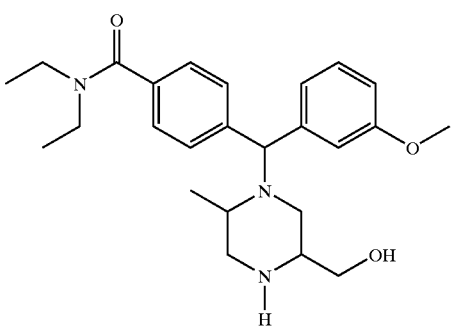
70
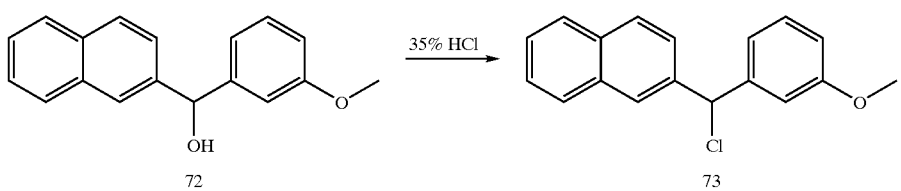
72  35% HCl  73
 allybromide 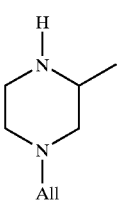
74
(7)  (7)
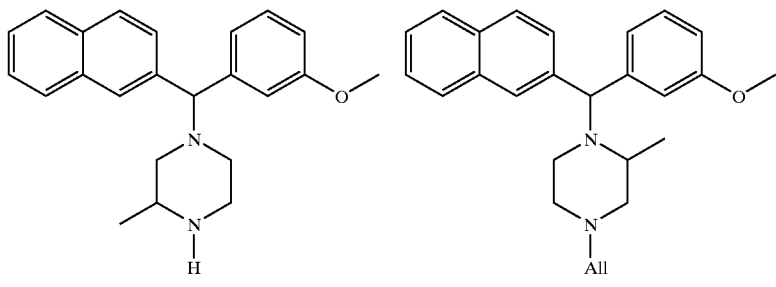
75  76

Diethylbenzamide Replacements etc.

The compounds according to Examples 43–48 were prepared as shown in Scheme 14 below.

R.

I. Preparation of 4-((4-t-Butoxycarbonyl-1-piperazinyl)-benzyl)-benzoic acid (Compound 78)

Compound 64 (6.0 g, 17 mmol) was dissolved in 6N hydrochloric acid and heated at 120° C. for 3 days. The solution was then neutralized with aquous NaOH (~12 g). The solution was concentrated to 100 mL, mixed with THF (100 mL) and di-t-butyl dicarbonate (3.7 g, 17 mmol) added dissolved in THF (50 mL). After stirring 1 h at 25° C., the aquous phase was acidified with 1M citric acid and extracted two times with ethyl acetate. The organic phase was dried ($K_2CO_3$) and evaporated, and the residue purified by chromatography on silica (EtOAc/heptane/AcOH, 10:90:0 to 66:33:1) to give a total of 3.85 g (57%) of compound 78.

Example 43

Preparation of 4-((1-piperazinyl)-benzyl)-benzoic acid dihydrochloride (Compound 79)

Compound 78 (150 mg, 0.38 mmol) was treated with excess HCl in acetic acid 1 h. Acid removed in vacuo and residue dissolved in methanol and precipitated by addition of ether. The precipitate was dried in vacuum at 100° C. Mp: 172–80° C. IR (KBr) (cm−1): 3000(br), 1700, 1606, 1454. $^1$H NMR: (DMSO-d6): δ=12.85 (s, 1H, $CO_2$H), 8.95 (s, 2H, NH), 7.92–7.20 (m, 9H, Ar—H), 4.56 (s, 1H, $Ar_2$CH), 3.33 (s, 8H, piperazne-H). Anal. calc. for $C_{18}H_{20}N_2O_2 \times 2HCl$, C,58.54; H, 6.00; N, 7.59. Found: C, 59.9; H, 6.47; N, 7.88.

Example 44 and 45

Preparation of Methyl 4-((4-t-butoxycarbonyl-piperazinyl)-benzyl)benzoate (Compound 80) and Methyl 4-((1-piperazinyl)-benzyl)benzoate dihydrochloride (Compound 81)

Compound 78 (0.15 g, 0.38 mmol) and cesium carbonate (0.25 g, 0.76 mmol) was mixed in DMF (2 mL) and methyl iodide (72 μL, 1.1 mmol) was added. After 2 h at 25° C., potassium carbonate (10%, aq.) and the solution was extracted with ethyl acetate. After evaporation of solvent in vacuo, the residue was purified by chromatography on silica (EtOAc/heptane, 30:70) to yield 0.13 g (87%) of the methyl ester, compound 80. Boc-deprotection was acheived by treatment with excess HCl in methanol at 50° C. The solvent was removed and the residue was purified again on silica. The dihydrochloride, compound 81 (35 mg), was prepared according to previous methodology. Mp: 185–95° C. IR (KBr) (cm−1): 3400(br), 2700(br), 1720, 1612, 1430, 1285, 1190, 1112. MS (EI, free amine): 310, 265, 225, 206, 165. $^1$H NMR: ($D_2O/CD_3OD$+DSS): δ=8.20–7.34 (m, 9H, Ar—H), 5.03 (s, 1H, $CHAr_2$), 3.89 (s, 3H, MeO), 3.42 (m, 4H, piperazine-H), 3.08 (m, 4H, piperazine-H). Anal. calc. for $C_{19}H_{22}N_2O_2 \times 2HCl \times 1H_2O$. C, 56.86; H, 6.53; N, 6.98. Found C: 56.82, H: 6.54; N, 7.00.

S.

I. Preparation of 4-((1-piperazinyl)-benzyl)-benzamide dihydrochloride (Compound 82)

Compound 78 (0.11 g, 0.28 mmol) was dissolved in dry methylene chloride/THF, 1:1 (5 mL) and cooled to −20° C. Triethylamine (78 μL, 0.56 mmol) was added and then i-butyl chloroformate (37 μL, 028 mmol). After 10 min, ammonia in methylene chloride (0.5 mL, 1.1M, 0.56 mmol) was added and the temperature was allowed to rise slowly to 25° C. After 3 h, the solvent was removed in vacuo and the residue was purified by chromatography on silica ($CH_2Cl_2$/MeOH/$NH_3$, 95:5:1 and 90:10:1) to give 70 mg (62%). Treatment with HCl in methanol 3 h at 50° C., removal of solvent in vacuo and chromatograpy on silica ($CH_2Cl_2$MeOH/$NH_3$, 90:10:1 and 80:20:1) gave the free amine which was converted to the dihydrochloride salt 82. Mp: 192–200° C. IR (KBr) (cm−1): 3939(br), 3184(br), 2700(br), 1665, 1610, 1565, 1426. MS (amine): 295, 250, 210, 165, 152. $^1$H NMR: (amine, $CD_3OD$): δ=7.96–7.22 (m, 9H, Ar—H), 4.93 (s, 2H, NH), 4.40 (s, 1H, $Ar_2CH$), 2.94+2.46 (2m, 8H, piperazine-H). Anal. calc. for $C_{18}H_{21}N_3O \times 2HCl \times 1.1H_2O$, C, 55.70; H,6.54; N, 10.83. Found C, 55.83; H, 6.76; N, 10.75.

Example 46

Preparation of 4-((1-piperazinyl)-benzyl)-N-ethylbenzamide hydrochloride (Compound 83)

The compound of this Example was prepared by following the synthesis procedure as described for compound 82, but substituting ammonia for ethylamine.

Mp: 180–85° C. IR (KBr) (cm−1): 3331(br), 2700(br), 1640, 1545, 1440, 1308. MS: (EI, amine) 323, 278, 267, 238, 195, 165. $^1$H NMR: (amine, $CD_3OD$): δ=7.84–7.14 (m, 9H, Ar—H), 4.9 (br. s, NH), 4.45 (s, 1H, $Ar_2CH$), 3.40 (m, 2H, ethyl-$CH_2$), 3.25, 2.65 (2m, 8H, piperazine-H), 1.20 (m, 3H, ethyl-Me).

Example 47

Preparation of 4-(1-piperazinyl-benzyl)-benzonitril dihydrochloride (Compound 84)

Compound 82 (45 mg, 0.11 mmol) was dissolved in dry THF (2 mL) and cooled to 0° C. Pyridine (36 μL, 0.44 mg) and trifluoroacetic anhydride (31 μL, 0.22 mmol) was added and stirring was continued for 1 h at 25° C. Water was added and the solution was extracted with ethyl acetate. The organic phase was washed with dilute $NaHCO_3$ (aq), dried ($K_2CO_3$) and evaporated in vacuo. The residue was treated with HCl in methanol 3 h at 50° C. Removal of solvent in vacuo and chromatograpy on silica ($CH_2Cl_2$/MeOH/$NH_3$, 90:10:1) of residue gave 15 mg (49%). Treatment with excess HCl in ether/methanol gave the dihydrochloride compound 84 which was precipitated, dissolved in water and freezedried. Mp: 141–45° C. IR (KBr) (cm−1): 3400 (br), 2700(br), 2230, 1434. MS (free amine): 277, 232, 192, 165. $^1$H NMR: (free amine, $CDCl_3$): δ=7.58–7.18 (m, 9H, Ar—H), 4.27 (s, 1H, $CHAr_2$) 2.89, 2.35 (2m, 8H, piperazine-H), 1.70 (s, NH). Anal. calc. for $C_{18}H_{19}N_3 \times 2HCl \times 1H_2O$, C, 58.70; H, 6.29; N, 11.41. Found C, 58.88; H, 6.46; N, 11.24.

Example 48

Preparation of 4-(1-piperazinyl-benzyl)-acetophenone dihydrochloride (Compound 85)

Compound 78 (0.20 g, 0.50 mmol) was dissolved in dry THF (5 mL) and cooled to 0° C. under nitrogen. Methyl lithium (3.1 mL, 0.8M in ether, 2.5 mmol) was added during 1 min and stirring was continued for 2 h. Chlorotrimethylsilane (0.63 mL, 5.0 mmol) was added and the temperature was allowed to reach 25° C., then ammonium chloride (aq) was added. The organic phase was decanted off, evaporated and the residue purified by chromatography on silica ($CH_2Cl_2$/MeOH/$NH_3$, 95:5:1) to give 0.11 g (75%) of ketone without Boc-group. The dihydrochloride salt, compound 85 was prepared by treatment with excess HCl in ether. Mp: 175–85° C. IR (KBr) (cm−1): 3400(br), 2700(br), 1680, 1607, 1424, 1269. MS (EI, free amine): 294, 249, 209, 165. ¹H NMR: (free amine, CDCl₃): δ=7.77–7.04 (m, 9H, Ar—H), 4.22 (s, 1H, CHAr₂), 2.92 (m, 4H, piperazine-H), 2.43 (s, 3H, MeCO), 2.40 (m, 4H, piperazine-H).
Anal. calc. for $C_{19}H_{22}N_2O \times 2HCl \times 1.6\ H_2O$, C, 57.61; H, 6.92; N, 7.07. Found C, 57.54; H, 6.75; N, 6.91.
Scheme 14
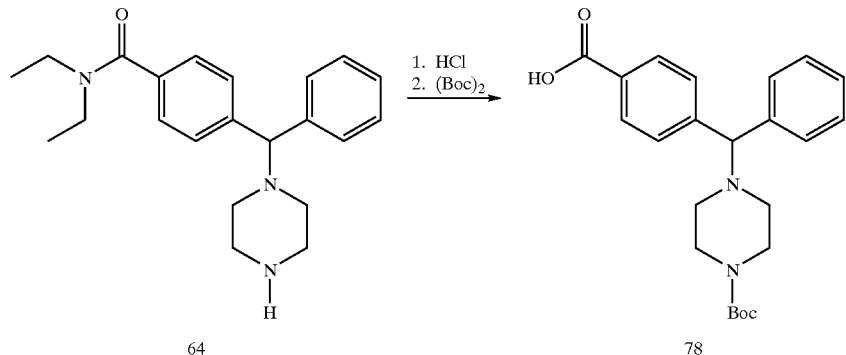
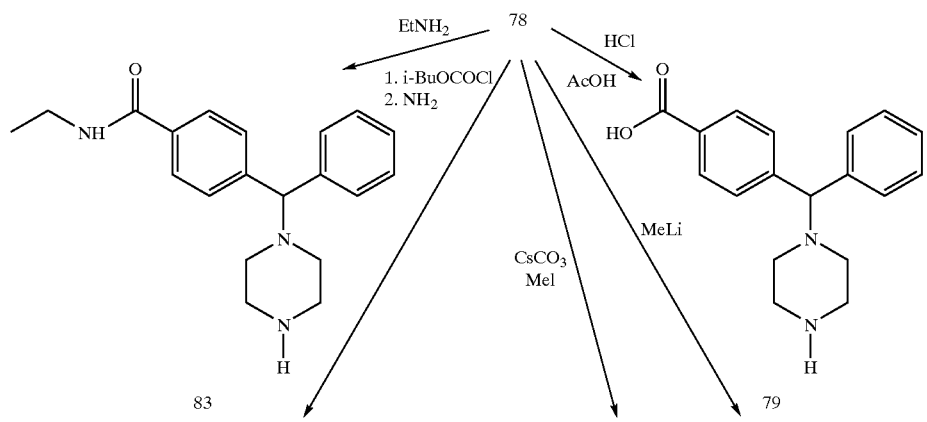
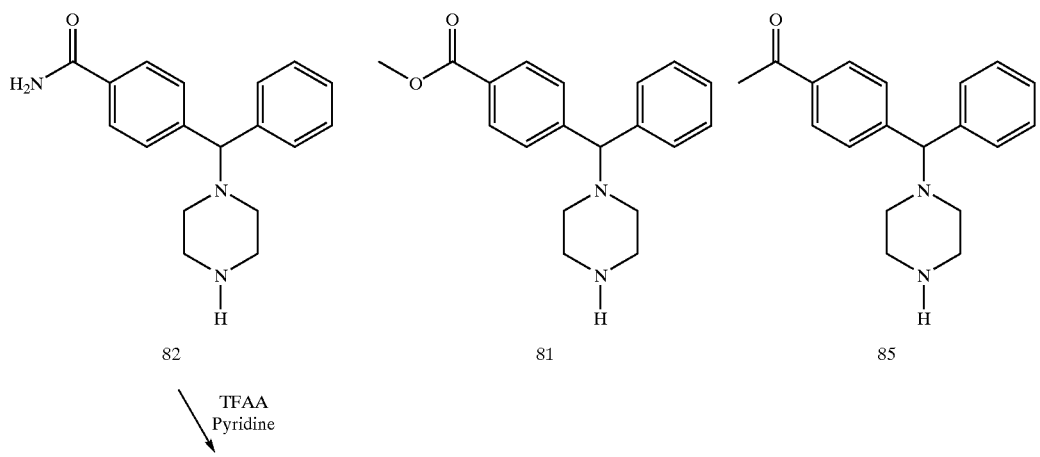

-continued

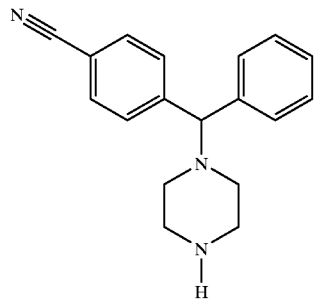
84

Scheme 15

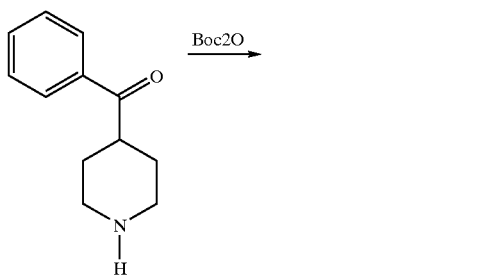

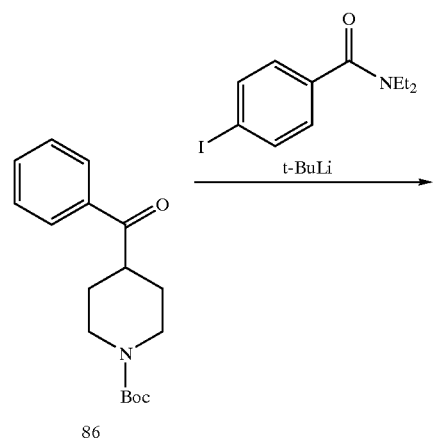
86

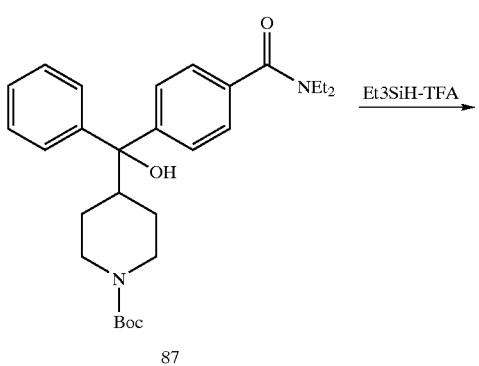
87

-continued

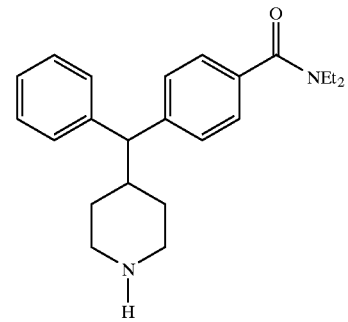
88

The compounds according to Example 49 were synthesized as shown in Scheme 15 above.

T.

I. Preparation of 4-benzoyl-N-t-butoxylcarbonylpiperidine (Compound 86)

A mixture of 4-benzoylpiperidine hydrochloride (6.77 g, 30.0 mmol), di-tert-butyldicarbonate (7.2 g, 33.0 mmol) and KHCO$_3$ (6.0 g, 60 mmol) in H$_2$O THF (50/20 mL) was refluxed for 1 h. The reaction mixture was extracted with ethyl acetate (2×100 mL). The combined organic layers were washed with brine, dried over MgSO$_4$. Removal of solvents gave 4-benzoyl-N-t-butoxylcarbonyl-piperidine (8.54 g, 98%); $\delta_H$ (400 MHz, CDCl$_3$) 1.47 (s, 9H), 1.70 (m, 2H), 1.83 (m, 2H), 2.91 (m, 2H), 3.42 (m, 2H), 4.18 (brs, 2H), 7.46 (m, 2H), 7.56 (m, 1H), 7.93 (m, 2H).

II. Preparation 4(α-Hydroxy-α-(4-N-t-butoxycarbonyliperidinyl)-benzyl)-N,N-diethylbenzamide (Compound 87)

To a solution of 4-iodo-N,N-diethylbenzamide (3.03 g, 10.0 mmol) and TMEDA (1.28 g, 11.0 mmol) in dry THF (30 mL) was added t-butyllithium (10.0 mL, 1.7 M, 17.0 mmol) at −78° C. After 10 min, 4-benzoyl-N-t-butoxylcarbonylpiperidine (2.89 g, 10.0 mmol) in THF (5 mL) was dropwise added. The reaction mixture was warmed to r.t. and then quenched with aqueous NH$_4$Cl solution and extracted with ethyl acetate (2×100 mL). The combined organic layers were washed with brine, dried over MgSO$_4$. Removal of solvents gave a crude product, which was purified by silica gel column eluting with MeOH—CH$_2$Cl$_2$ (0:100→2:98) to provide 4-(α-hydroxy-α-(4-N-t-butoxylcarbonylpiperidinyl)-benzyl)N,N-diethylbenzamide (MTL 0327, 2.60 g, 56%): m.p.: 100–103° C. (CH$_2$Cl$_2$): $v_{max}$ (KBr) cm$^{-1}$ 3426, 2973, 1687, 1618, 1428, 1289, 1168; $\delta_H$ (400 MHz, CDCl$_3$) 1.08 (brs, 3H), 1.20 (brs, 3H), 1.30 (m, 4H), 1.41 (s, 9H), 2.50 (t, J=1.2 Hz. 1H). 2.66 (m, 2OH), 3.22 (brs, 2H), 3.50 (brs, 2H), 4.09 (brs, 2H), 7.18 (m, 1H), 7.26 (m, 4H), 7.45 (m, 4H); $\delta_{C-13}$ (100 MHz, CDCl$_3$) 12.8, 14.1, 26.2, 28.3, 39.1, 43.2, 44.3, 53.3, 79.2, 79.4. 125.75, 125.79, 126.2, 126.6, 128.1, 135.1, 145.3, 146.8, 154.6, 171.0.

Example 49

Preparation 4-((α-4piperidinyl)-benzyl)-N,N-diethylbenzamide (Compound 88)

To a solution of 4-(α-hydroxy-α-(4N-t-butoxylcarbonylpiperidinyl)benzyl)-N,N-diethylbenzamide (466 mg, 1.0 mmol) and triethylsilane (232 mg, 2.0 mmol) in dry dichloromethane (10 mL) was added trifluoroacetic acid (10.0 mL) at r.t. After 30 min at r.t., more triethylsilane (232 mg, 2.0 mmol) was added. The reaction mixture was stirred for 14 h at r.t., and then condensed. The residue was dissolved in AcOEt (100 ml). The resulting solution was washed with 1 N NaOH solution, aqueous NHt$_4$ solution and brine, dried over MgSO$_4$. Removal of solvents gave a crude product, which was purified by silica gel column eluting with NH$_4$OH (1 N)-MeOH—CH$_2$Cl$_2$ (2.5:15:82.5) to provide 4((α-piperidinyl)-benzyl)N,N-diethylbenzamide (245 mg, 70%): m.p.: 160–162° C. (CH$_2$Cl$_2$); $v_{max}$ (KBr) cm$^{-1}$ 3325, 2937, 1613, 1461, 1283, 1095; $\delta_H$ (400 MHz, CDCl$_3$) 1.05 (brs, 3H), 1.07 (m, 2H), 1.19 (brs, 3H), 1.53 (m, 2H), 2.04 (brs, NH), 2.20 (m, 1H), 2.55 (t, J=11.6 Hz, 2H), 3.01 (m, 2H), 3.23 (brs, 2H), 3.51 (d, J=10.4 Hz, 1H), 3.52 (brs, 2H), 7.15 (m, 1H), 7.27 (m, 8H); $\delta_{C-13}$ (100 MHz, CDCl$_3$) 12.8, 14.1, 32.2, 39.0, 39.9, 43.1, 46,5, 59.0, 126.1, 126.5, 127.9, 128.0, 128.3, 134.8, 143.0, 144.7, 171.0.

Example 50

Preparation of N,N-Diethyl-4-(3-methoxybenzyl-1-piperazinyl)-benzamide

Procedure as for N,N-Diethyl-4-[(2,5,5-trimethyl-1-piperazinyl)-3-methoxybenzyl]-benzamide. N,N-Diethyl-4 (chloro-3-methoxybenzyl)-benzamide (1.6 g, 4.8 mmol) was reacted with piperazine (1.6 g, 19 mmol) in acetonitrile (20 mL) for 4 h at 80° C. to give a is total of 1.1 g product (63%) which was converted into the dihydrochloride salt. Mp: 165–82° C. IR (amine, CDCl$_3$ in KBr cell) (cm-1): 3688, 1611, 1458, 1436, 1285. MS(free amine): 381, 336, 296, 224, 196, 165, 152, 112. $^1$H NMR: (amine, CDCl$_3$): δ=1.05, 1.15 (2 br. s, 6H, 2Me), 2.51, 3.02 (2br. s, 8H, piperazine-H), 3.2, 3.45 (2 br. s, 4H, MeCH$_2$) 3.72, 3.73 (2s, 3H, MeO), 4.21 (s, 1H, CHAr$_2$), 4.5 (br. s, 1H, NH), 6.60–7.40 (m, 8H, Ar—H). C$_{23}$H$_{31}$N$_3$O$_2$x2HClx0.80 H$_2$O requires: C, 58.92; H, 7.44; N, 8.96. Found: C, 7.76; N, 8.86.

Example 51

Preparation of N,N-Diethyl-4-[(4-allyl-1-piperazinyl)-3-methoxybenzyl]-benzamide Procedure as for N,N-Diethyl[(4-allyl-2,5,5-trimethyl-1-piperazinyl)-3-methoxybenzyl]-benzamide.

N,N-Diethyl-4-(3-methoxybenzyl-1-piperazinyl)-benzamide (0.16 g, 0.42 mmol) gave 30 mg product (20%) which was converted to dihydrochloride salt Mp: 151–76° C. IR (amine, CDCl$_3$ in KBr cell) (cm-1): 3688,1611, 1457,1435,1288. MS(free amine): 421, 125. $^1$H NMR: (amine, CDCl$_3$): δ=1.1 (2 br. s, 6H, 2Me), 2.3–2.6 (br. s, 8H, piperazine-H), 3.00 (m, 2H, allyl-H), 3.2–3.5 (2 br. s, 4H, MeCH$_2$),3.78 (s, 3H, MeO), 4.20 (s, 1H, CHAr$_2$), 5.14 (m, 2H, allyl-H), 5.85 (m, 1H, allyl-H), 6.70–7.46 (m, 8H, Ar—H). C$_{26}$H$_{35}$N$_3$O$_2$x2HClx1.4 H$_2$O requires: C, 60.09; H, 7.72; N, 8.08. Found C, 60.12; H, 7.59; N, 7.88.

Scheme 16

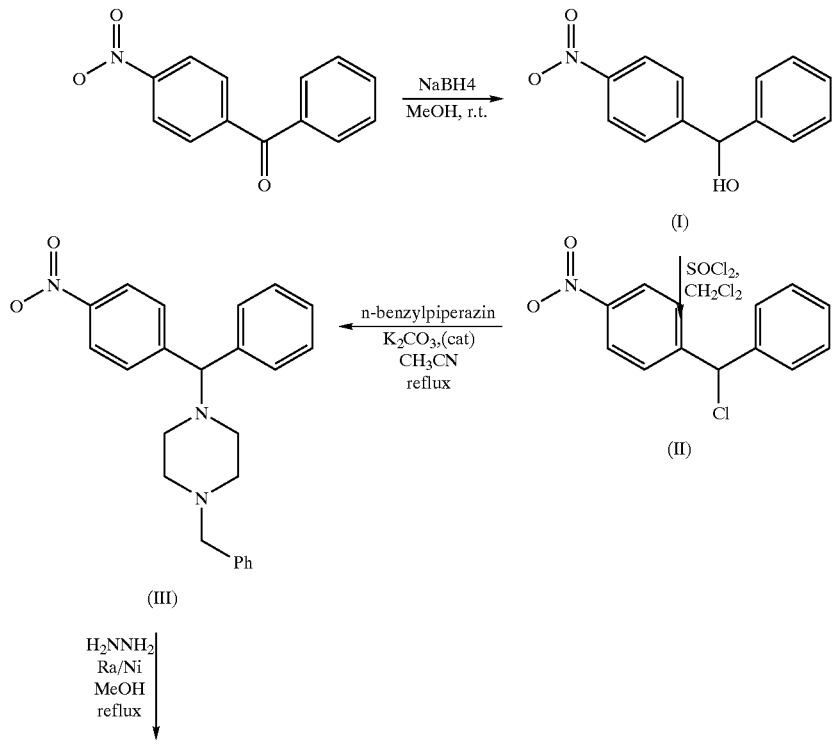

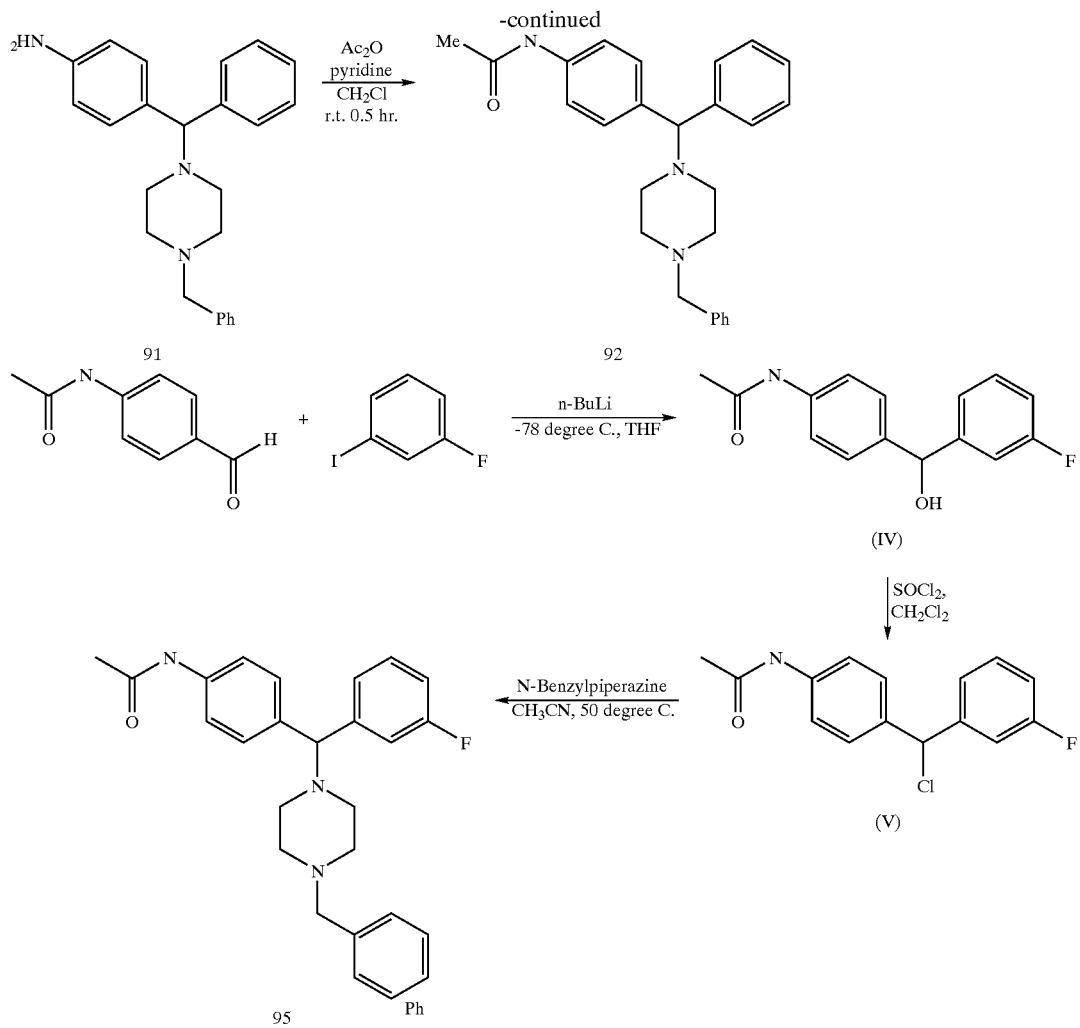

The compounds of Examples 52–55 were synthesized as shown in Scheme 16 above.

U

Compound I: 4-(α-hydroxybenzyl)-nitrobenzene 4-nitrobenzoin (4.55 g, 20.1 mmol) was dissolved in 70 ml of anhydrous methanol cooled down to 0° C. in an ice bath, NaBH₄ (0.915 g, 24.2 mmol) was then added under N₂, the mixture was stirred at r.t., for overnight, quenched with NH₄Cl sat'd aqueous solution, MeOH was evaporated and EtOAc was added, the mixture was washed with water, the organic layer was dried over MgSO₄ and concentrated to give a solid as the desired product(~4.58 g, ~100% yield).

¹H NMR (CDCl₃, TMS): δ(ppm): 2.40 (s, br, 1H, O$\underline{H}$); 5.92 (d, J=3.2 Hz, 1H, Ar—C$\underline{H}$—OH); 7.30–7.40 (m, 5H, Ar); 7.58 (d, J=8.6, 2H, Ar—NO₂); 8.18

Compound II: 4-(α-chlorobenzyl)-nitrobenzene

Compound I (4.58 g, 20 mmol) was dissolved in anhydrous CH₂Cl₂, thionyl chloride (4.68 g, 39.4 mmol) was then added to the mixture under N₂, the reaction mixture was refluxed for 5 hr and was cooled down to r.t., the solvent and excess of thionyl chloride were evaporated under vacuum to give a yellowish solid as the desired product (~100%yield).

¹H NMR (CDCl₃, TMS): δ(ppm): 6.16 (s, 1H, —C$\underline{H}$—Cl); 7.30–7.40 (m, 5H, Ar); 7.59 (d, J=8.6 Hz, 2H, Ar—NO₂); 8.20 (d, J=8.6 Hz, 2H, Ar—NO₂).

Compound III: 4[(N-benzyl-1-piperazinyl)-benzyl]-nitrobenzene

To compound II (1.0 g, 4.1 mmol) and N-benzylpiperazine (1.45 g, 8.2 mmol) dissolved in anhydrous acetonitrile, catalytic amount of potassium carbonate was added and the reaction mixture was then refluxed overnight. After cooling down to r.t., the mixture was washed with brine, the organic layer was concentrated under vacuum to give an oil, it was then purified by MPLC using CH₂Cl₂/MeOH/NH₄OH=95/5/1 as the eluent to give the pure desired product (1.2 g, 76% yield).

¹H NMR(CDCl₃, TMS): δ: 2.41–2.48 (8H, br, piperazin ring), 3.51 (2H, s, Ph—C$\underline{H}$₂), 4.34 (1H, s, Ar—C$\underline{H}$—Ar), 7.20–8.12 (14H, Ar)ppm.

¹³C NMR(CDCl₃, TMS): δ: 51.7, 53.1, 62.9, 75.5, 123.8, 127.0, 128.1, 128.5, 128.7, 129.2, 137.9, 140.9, 146.8, 150.6 ppm.

Example 52

Preparation of 4-[(N-benzyl-1-piperazinyl)-benzyl]-aniline (Compound 91)

To compound III (900 mg, 2.33 mmol) dissolved in 10 ml MeOH, Ra—Ni (150 mg) was added and the temperature was increased to 35° C., hydrazine (380 mg, 11.63 mmol) was then added slowly via a syringe while it was stirring, the temperature of the mixture was increased to 70° C., until the evolution of the gas seized, the reaction mixture was cooled down to r.t., filtered over celite and concentrated to give an oil, which was purified by MPLC using $CH_2Cl_2/MeOH=99/1–99/5$ as the eluent to give a yellowish solid as the desired product (660 mg, ~80%yield).

Elemental Analysis Calcd.for: $C_{24}H_{27}N_3O.2H_2O$: C, 79.64; H, 7.43; N, 11.55. Found: C, 79.83; H, 7.65; N, 11.64.

IR (NaCl Film): ν=2807, 1620, 1513, 1451, 1282, 1137cm$^{-1}$.

$^1$H NMR(CDCl$_3$, TMS): δ: 2.3–2.48 (8H, br, piperazine ring), 3.45 (2H, s, br, —N$\underline{H}_2$), 3.48 (2H, s, Ph—C$\underline{H}_2$), 4.10 (1H, s, Ar—C$\underline{H}_2$), 6.51 (2H, m, Ar), 7.11–7.37 (12H, m, Ar)ppm.

Example 53

Preparation of 4-[(N-benzyl-1-piperazinyl)-benzyl]-acetanilide (Compound 92)

To 4[N-benzyl-1-piperazinyl)-benzyl]-aniline (compound 91) (5(mg, 0.14 mmol) and anhydrous pyridine(excess) were dissolved in anhydrous dichloromethane, followed by the addition of acetic anhydride (4eq.). The reaction mixture was stirred at r.t., for 30 min. and quenched by H$_2$O, then washed with sat'd NaHMCO$_3$ aqueous solution and brine, the organic layer was dried over anhydrous MgSO$_4$, filtered and concentrated to give an oil as the product (44 mg, 80%yield).

$^1$H NMR: (CDCl$_3$, TMS) δ: 2.1(3H, s, —C$\underline{H}_3$), 2.3–2.48 (8H, br, pipyrazin ring), 3.48 (2H, s, Ph—C$\underline{H}_2$), 4.16 (1H, s, Ar—C$\underline{H}$—Ar), 7.20–8.12 (14H, Ar)ppm.

Elemental Analysis Calcd.for: $CH_{29}N_3O$. 2.1HCl. 0.3H$_2$O: C, 64.83; H, 6.64; N, 8.40. Found: C, 64.86; H, 6.64; N, 8.73

Example 54

Preparation of 4-[(N-benzyl-1-piperazinyl)-benzyl]-methanesulfonamide

To 4-[(N-benzyl-1-piperazinyl)-benzyl]-aniline (compound 91) (100 mg, 0.28 mmol) and pyridine (excess) were dissolved in anhydrous dichloromethane (5 ml) followed by the addition of methanesufonic anhydride(97.55 mg, 0.56 mmol), the reaction mixture was stirred at rt. for 20 min. followed by TLC, then it was quenched by adding drop of water, 10 ml of EtOAc was added, the mixture was washed with saturated NH$_4$a aqueous solution and brine, the organic layer was dried over MgSO$_4$, concentrated and purified by MPLC using $CH_2Cl_2/MeOH=99/1–95/5$ as the solvent to give the pure product as a white solid (~90 mg, ~70%yield).

Melting point: 195–200° C.(dcp.)

$^1$H NMR: (CDCl$_3$, TMS) δ: 2.3–2.48 (8H, br, pipyrazin ring), 2.96 (3H, s, C$\underline{H}_3$SO$_2$), 3.51 (2H, s, Ph—C$\underline{H}_2$, 4.21 (1H, s, Ar—C$\underline{H}$—Ar), 6.25 (1H, br, S—N$\underline{H}$—), 7.10–7.41 (14H, m, Ar)ppm.

$^{13}$C NMR:(CDCl$_3$) δ: 142.4, 140.2, 137.9, 135.3, 129.2, 129.1, 128.5, 128.1, 127.9, 127.0, 121.0, 75.5, 63.0, 53.2, 51.8, 39.3 ppm.

Elemental analysis: Calcd.for: $C_{25}H_{29}N_3O_2S$. 0.9H$_2$O: C, 66.46; H, 6.87; N, 9.30. Found: 66.53; H. 6.61; N, 9.23.

Example 55

Preparation of Methyl-N-4-[(N-benzyl-1-piperazinyl)-benzyl]-2-methylacetate

To 4[(N-benzyl-1-piperazinyl)-benzyl]-an-line (compound 91) (100 mg, 0.28 mmol), Lithium hydride (2.5 mg, 0.3 mmol) and l-bromomethylacetate (44.16 mg, 0.28 mmol) were mixed in anhydrous THF, the reaction mixture were refluxed for 2 hr. and cooled down to rt., then quenched with drops of water, washed with brine twice dried over anhydrous MgSO$_4$ and concentrated to an oil, purified by MPLC using $CH:CH_2/MeOH=98/2$ as the solvent to give an oil as the product (~23 mg, 20%).

IR (NaCl Film): HCl salt

ν=3404(br), 2922(br), 1745,1610, 1517, 1439,1207cm$^{-1}$ $^1$H NMR: (CDCl$_3$) δ: 2.40 (8H, br, piperazine ring), 3.50 (2H, s, Ph—C$\underline{H}_2$), 3.75 (3H, s, —O—C$\underline{H}_3$), 3.85 (2H, d, J=5.2 Hz, N—C$\underline{H}_2$), 4.12 (1H, s, Ar—C$\underline{H}$—Ar), 4.18 (1H, t, J=5.2 Hz, Ar—N$\underline{H}$—CH$_2$). 6.49 (2H, d, J=8.4 Hz, —N—Ar), 7.14~7.38 (12H, m, Ar)ppm.

Anal.Calcd.for: $C_{27}H_{31}N_3O_2$.3HCl: C, 60.17; H, 6.36; N, 7.80. Found: C, 59.97; H, 6.61; N, 7.46.

Compound IV: 4-(3-fluoro-α-hydroxybenzyl)-acetonitrile

To 1-Fluoro-3-iodo-benzene (7.53 g, 33.9mmol) was dissolved in anhydrous THF and was cooled down to −78° C., n-Butyllithium (2.5M in THF, 33.9 mmol) was added slowly into the reaction mixture via a syringe, the mixture was stirred for 10 min. followed by the addition of the solution of 4-Acetamidobenzaldehyde (1.84 g, 11.3 mmol) in 5 ml of dry DME, the reaction mixture was then stirred at −78° C. for 30 min. before quenched with NH$_4$Cl aqueous solution. The organic layer was washed with brine and dried over anhydrous MgSO$_4$, filtered and concentrated to an oil, purified by MPLC using 10% heptane in CH$_2$Cl$_2$ and 100%CH$_2$Cl$_2$ to give the pure product (1.65 g, 56% yield).

$^1$H NMR: (CDCl$_3$) δ: 2.14 (3H, s, OCC$\underline{H}_3$), 2.55 (1H, s, br, O$\underline{H}$), 5.76 (1H, d, J=3.2 Hz, Ar—C$\underline{H}$—Ar), 7.35 (1H, s, CON$\underline{H}$), 6.90~7.50 (8H, m, Ar)ppm.

Compound V: 4-(3-fluoro-α-chlorobenzyl)-acetonitrile

This was prepared using the same method as described for the preparation of compound (II) but using compound (IV). It was used directly for the next step reaction without purification.

$^1$H NMR: (CDCl$_3$) δ: 2.15 (3H, s, OCC$\underline{H}_3$), 6.10 (1H, s, Ar—C$\underline{H}$—Ar), 7.84 (1H, s, CON$\underline{H}$), 6.90~7.6 (8H, m, Ar), 7.84 (1H, s, CON$\underline{H}$)ppm.

Example 56

Preparation of 4-[(N-benzyl-1-piperazinyl)-3-fluorobenzyl]-acetanilide (Compound 95)

This was prepared using the same method as described for the preparation of compound (III) but using compound (V).

$^1$H NMR: (CDCl$_3$) δ: 2.14 (3H, s, OCC$\underline{H}_3$), 2.40 (8H, br, piperazine), 3.51 (2H, s, Ph—C$\underline{H}_2$), 4.19 (1H, s, Ar—C$\underline{H}$—Ar), 6.80~7.40 (13H, m, Ar)ppm.

ANALYSIS: Anal.Calcd.for: $C_{26}H_{28}FN_3O.2HCl.1.6CH_2Cl_2.2H_2O$: C, 56.24; H, 6.02; N, 7.13. Found: C, 56.29; H, 6.10; N, 6.88.

Pharmaceutical Compositions

The novel compounds according to the present invention may be administered per orally, intramuscularly, subcutaneously, intraperitoneally, intrathoracially, intravenously, intrathecally and intracerebroventricularly.

The dosage will depend on the route of administration, the severity of the disease, age and weight of the patient and other factors normally considered by the attending physician, when determining the individual regimen and dosage level at the most appropriate for a particular patient.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stilling. The molten homogeneous mixture is then poured into convenient sized molds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Pharmaceutically acceptable salts are acetate, benzenesulfonate, benzoate, bicarbonate. bitartrate, bromide, calcium acetate, camsylate, carbonate, chloride, cetrate, dihydrochloride, edetate, edisylate, estolate, esylate, furnarate, glucaptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannata, tartrate, teoclate, triethiodide, benzathine, chloroprocaine, choline, diethanolamine, ethylenediamine, meglumine, procaine, aluminium, calcium, lithium, magnesium, potassium, sodium, and zinc.

Preferred pharmaceutically acceptable salts are the hydrochlorides and citrates.

The term composition is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid from compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical compositions is in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

Biological Evaluation
In vitro Model
Cell Culture

Human 293S cells expressing cloned human $\mu$, $\delta$, and $\kappa$ receptors and neomycin resistance were grown in suspension at 37° C. and 5% $CO_2$ in shaker flasks containing calcium-free DMEM10% FBS, 5% BCS, 0.1% Pluronic F-68, and 600 $\mu$g/ml geneticin.

Membrane Preparation

Cells were pelleted and resuspended in lysis buffer (50 mM Tris, pH 7.0, 2.5 mM EDTA, with PMSF added just prior to use to 0.1 mM from a 0.1 M stock in ethanol), incubated on ice for 15 min, then homogenized with a polytron for 30 sec. The suspension was spun at 1000 g (max) for 10 min at 4° C. The supernatant was saved on ice and the pellets resuspended and spun as before. The supernatants from both spins were combined and spun at 46,000 g(max) for 30 min. The pellets were resuspended in cold Tris buffer (50 mM Tris/Cl, pH 7.0) and spun again. The final pellets were resuspended in membrane buffer ( 50 mM Tris, 0.32 M sucrose, pH 7.0). Aliquots (1 ml) in polypropylene tubes were frozen in dry ice/ethanol and stored at –70° C. until use. The protein concentrations were determined by a modified Lowry assay with SDS.

Binding Assays

Membranes were thawed at 37° C., cooled on ice, passed 3 times through a 25-gauge needle, and diluted into binding buffer (50 mM Tris, 3 mM $MgCl_2$, 1 mg/ml BSA (Sigma A-7888), pH 7.4, which was stored at 4° C. after filtration through a 0.22 m filter, and to which had been freshly added 5 $\mu$g/ml aprotinin, 10 $\mu$M bestatin, 10 $\mu$M diprotin A, no DTT). Aliquots of 100 $\mu$l (for $\mu$g protein, see Table 1) were added to iced 12×75 mm polypropylene tubes containing 100 $\mu$l of the appropriate radioligand (see Table 1) and 100 $\mu$l of test peptides at various concentrations. Total (TB) and nonspecific (NS) binding were determined in the absence and presence of 10 $\mu$M naloxone respectively. The tubes were vortexed and incubated at 25° C. for 60–75 min, after which time the contents are rapidly vacuum-filtered and washed with about 12 ml/tube iced wash buffer (50 mM Tris, pH 7.0, 3 mM $MgCl_2$) through GF/B filters (Whatman) presoaked for at least 2 h in 0.1% polyethyleneimine. The radioactivity (dpm) retained on the filters was measured with a beta counter after soaking the filters for at least 12 h in minivials containing 6–7 ml scintillation fluid. If the assay is set up in 96-place deep well plates, the filtration is over 96-place PEI-soaked unifilters, which were washed with 3×1 ml wash buffer, and dried in an oven at to 55° C. for 2 h. The filter plates were counted in a TopCount (Packard) after adding 50 $\mu$l MS-20 scintillation fluid/well.

Data Analysis

The specific binding (SB) was calculated as TB-NS, and the SB in the presence of various test peptides was expressed as percentage of control SB. Values of $IC_{50}$ and Hill coefficient ($n_H$) for ligands in displacing specifically bound radioligand were calculated from logit plots or curve fitting programs such as Ligand, GraphPad Prism, SigmaPlot, or ReceptorFit Values of $K_i$ were calculated from the Cheng-Prussoff equation. Mean±S.E.M. values of $IC_{50}$, $K_i$ and $n_H$ were reported for ligands tested in at least three displacement curves.

Receptor Saturation Experiments

Radioligand $K_\delta$ values were determined by performing the binding assays on cell membranes with the appropriate radioligands at concentrations ranging from 0.2 to 5 times the estimated $K_\delta$ (up to 10 times if amounts of radioligand required are sable). The specific radioligand binding was expressed as pmole/mg membrane protein. Values of $K_\delta$ and $B_{max}$ from individual experiments were obtained from non-linear fits of specifically bound (B) vs. nM free (F) radioligand from individual according to a one site model.

Biological Model (In vivo Model)
Freund's Complete Adjuvant (FCA), and Sciatic Nerve Cuff Induced Mechano-Allodynia in Rat Animals Male Sprague-Dawley rats (Charles River, St-Constant, Canada) weighing 175–200 g at the time of surgery were used. They were housed in groups of three in rooms thermostatically maintained at 20° C. with a 12:12 hr light/dark cycle, and with free access to food and water. After arrival, the animals were allowed to acclimatize for at least 2 days before surgery. The experiments were approved by the appropriate Medical Ethical Committee for animal studies.

Experimental Procedure

Freund's Complete Adjuvant

The rats were first anesthetized in a Halothane chamber after which 10 μl of FCA was injected s.c. into the dorsal region of the left foot, between the second and third external digits. The animals were then allowed to recover from anesthesia under observation in their home cage.

Sciatic Nerve Cuff

The animals were prepared according to the method described by Mosconi and Kruger (1996). Rats were anesthetized with a mixture of Ketamine/Xylazi i.p. (2 ml/kg) and placed on their right side and an incision made over, and along the axis of, the lateral aspect of the left femur. The muscles of the upper quadriceps were teased apart to reveal the sciatic nerve on which a plastic cuff (PE60 tubing, 2 mm long) was placed around. The wound was then closed in two layers with 3-0 vicryl and silk sutures Determination of Mechano-Allodynia Using Von Frey Testing Testing was performed between 08:00 and 16:00 h using the method described by Chaplan et al. (1994). Rats were placed in Plexiglas cages on top of a wire mesh bottom which allowed access to the paw, and were left to habituate for 10–15 min. The area tested was the mid-plantar left hind paw, avoiding the less sensitive foot pads. The paw was touched with a series of 8 Von Frey hairs with logarithmically incremental stiffness (0.41, 0.69, 1.20, 2.04, 3.63, 5.50, 8.51, and 15.14 grains; Stoelting, Ill., USA). The von Frey hair was applied from underneath the mesh floor perpendicular to the plantar surface with sufficient force to cause a slight buckling against the paw, and held for approximately 6–8 seconds. A positive response was noted if the paw was sharply withdrawn. Flinching immediately upon removal of the hair was also considered a positive response. Ambulation was considered an ambiguous response, and in such cases the stimulus was repeated.

Testing Protocol

The animals were tested on postoperative day 1 for the FCA-treated group and on post-operative day 7 for the Sciatic Nerve Cuff group. The 50% withdrawal threshold was determined using the up-down method of Dixon (1980). Testing was started with the 2.04 g hair, in the middle of the series. Stimuli were always presented in a consecutive way, whether ascending or descending. In the absence of a paw withdrawal response to the initially selected hair, a stronger stimulus was presented; in the event of paw withdrawal, the next weaker stimulus was chosen. Optimal threshold calculation by this method requires 6 responses in the immediate vicinity of the 50% threshold, and counting of these 6 responses began when the first change in response occurred, e.g. the threshold was first crossed. In cases where thresholds fell outside the range of stimuli, values of 15.14 (normal sensitivity) or 0.41 (maximally allodynic) were respectively assigned. The resulting pattern of positive and negative responses was tabulated using the convention, X=no withdrawal; O=withdrawal, and the 50% withdrawal threshold was interpolated using the formula:

$$50\% \text{ g threshold} = 10^{(Xf+k\delta)}/10{,}000$$

where Xf=value of the last von Frey hair used (log units); k=tabular value (from Chaplan et al. (1994)) for the pattern of positive/negative responses; and δ=mean difference between stimuli (log units). Here δ=0.224.

Von Frey thresholds were converted to percent of maximum possible effect (% MPE), according to Chaplan et al. 1994. The following equation was used to compute % MPE:

$$\% \text{ MPE} = \frac{\text{Drug treated threshold (g)} - \text{allodynia threshold (g)}}{\text{Control threshold (g)} - \text{allodynia threshold (g)}} \times 100$$

Administration of Test Substance

Rats were injected (subcutaneously, intraperitoneally, or orally) with a test substance prior to von frey testing, the time between administration of test compound and the von frey test varied depending upon the nature of the test compound.

What is claimed is:

1. A compound of formula (I)

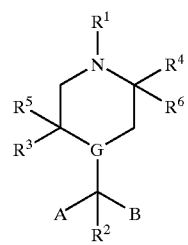

(I)

wherein

G is a nitrogen atom;

A is: 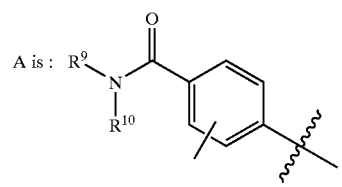

wherein the phenyl ring of each A group may be optionally and independently substituted by one or two substituents selected from the group consisting of $CH_3$, $CF_3$ and halogen;

$R^1$ is selected from the group consisting of: H; a branched or straight $C_1$–$C_6$ alkyl; $C_2$–$C_6$ alkenyl; —CO($C_1$–$C_6$ alkyl); and ($C_1$–$C_6$ alkyl)-B wherein B is a $C_6$, $C_9$ or $C_{10}$ aryl or a 5 or 6 membered heteroaryl having a heteroatom selected from any of S, N and O and wherein the $C_6$, $C_9$ or $C_{10}$ aryl and the 5 or 6 membered heteroaryl may be optionally substituted with 1 or 2 substituents selected from $CH_3$ or halogen;

R² is selected from the group consisting of H and CH₃;

R⁹, R¹⁰, R¹³, R¹⁴, R¹⁷ and R¹⁸ are selected from the group consisting of H, a branched or straight $C_1$–$C_6$ alkyl and $C_2$–$C_6$ alkenyl;

B is a substituted or unsubstituted $C_6$, $C_9$ or $C_{10}$ aromatic; a $C_6$, $C_9$ or $C_{10}$ hydroaromatic; each optionally substituted by one or two substituents selected from the group consisting of: CH₃, halogen, $(CH_2)_p CONR^7 R^8$, $(CH_2)_p COR^7$, and $(CH_2)_p SOR^7$, wherein p is 0, 1, or 2, and wherein R⁷ and R⁸ are selected from: H, or a $C_1$–$C_3$ alkyl;

R³, R⁴, R⁵, and R⁶ are each H;

as well as pharmaceutically acceptable salts of the compounds and isomers, other than positional isomers, thereof; with the proviso that when R¹ is a straight $C_1$–$C_6$ alkyl, B is not a $C_6$ aromatic substituted with a halogen.

2. The compound of claim 1, wherein B is an unsubstituted $C_6$, $C_9$ or $C_{10}$ aromatic.

3. A compound selected from the group consisting of:

(±) 4-((a-(1-piperazinyl))-4-chlorobenzyl)-N,N-diethylbenzamide (compound 33);

(±) 4-((a-((4-allyl)-1-piperazinyl))-4-chlorobenzyl)-N,N-diethylbenzamide.2HCl (compound 34);

(±) 4-((a-(1-piperazinyl))-2-naphthylmethyl)-N,N-diethylbenzamide (compound 37);

(±) 4-((a-((4-allyl)-1-piperazinyl))-2-naphthylmethyl)-N,N-diethylbenzamide (compound 38);

(±) 4-((a-(1-piperazinyl))-4-xylyl)-N,N-diethylbenzamide (compound 41);

(±) 4-((a-((4-allyl)-1-piperazinyl))-4-xylyl)-N,N-diethylbenzamide.2HCl (compound 42);

(±) 4-((a-(1-piperazinyl))-3-xylyl)-N,N-diethylbenzamide.2HCl (compound 45);

(±) 4-((a-(1-piperazinyl))-cyclohexylmethyl-N,N-diethylbenzamide (compound 48);

(±) 4-((a-(1-piperazinyl))-1-naphthylmethyl)-N,N-diethylbenzamide (compound 54);

4-((1-piperazinyl)-benzyl)-N,N-diethylbenzamide dihydrochloride (compound 64);

4-((4-allyl-1-piperazinyl)-benzyl)-N,N-diethylbenzamide dihydrochloride (compound 65);

4-((4-acetyl-1-piperazinyl)-benzyl)-N,N-diethylbenzamide hydrochloride (compound 77);

4-(4-(2-hydroxymethyl-5-methyl)piperazinyl-benzyl)-N,N-diethyl-benzamide dihydrochloride (compound 69);

4-((4-(2-hydroxymethyl-5-methyl)piperazinyl)-3-methoxybenzyl)-N,N-diethylbenzamide dihydrochloride (compound 70);

4-((4-(1-allyl-2-hydroxymethyl-5-methyl)piperazinyl)-3-methoxybenzyl)-N,N-diethylbenzamide dihydrochloride (compound 71);

4-((1-piperazinyl)-benzyl)-N-ethylbenzamide hydrochloride (compound 83).

4. The compound of claim 3, wherein said compound is:

(±) 4-((α-(1-piperazinyl))-2-naphthylmethyl)-N,N-diethylbenzamide.

5. The compound according to any one of claims 1, 2, 3 or 4, wherein said compound is in the form of its hydrochloride salt.

6. A pharmaceutical composition comprising a compound according to any one of claims 1, 2, 3 or 4, as an active ingredient, together with a pharmaceutically acceptable carrier.

7. A method of treating a patient for pain comprising administering the compound of claim 3 or claim 4 to said patient in an amount sufficient to reduce or eliminate said pain.

* * * * *